US008518107B2

(12) United States Patent
Tsukashima et al.

(10) Patent No.: US 8,518,107 B2
(45) Date of Patent: Aug. 27, 2013

(54) PERCUTANEOUS TRANSCATHETER REPAIR OF HEART VALVES

(75) Inventors: Ross Tsukashima, San Diego, CA (US); Samuel M. Shaolian, Newport Beach, CA (US); Maurice Buchbinder, La Jolla, CA (US); Brian C. Gray, Lake Forest, CA (US); Victor S. Packham, Costa Mesa, CA (US); Hung H. Cao, Corona, CA (US)

(73) Assignee: ValCare, Inc., Irvine, CA (US)

( * ) Notice: Subject to any disclaimer, the term of this patent is extended or adjusted under 35 U.S.C. 154(b) by 14 days.

(21) Appl. No.: 13/198,582

(22) Filed: Aug. 4, 2011

(65) Prior Publication Data

US 2012/0123531 A1 May 17, 2012

Related U.S. Application Data

(60) Provisional application No. 61/370,754, filed on Aug. 4, 2010, provisional application No. 61/383,681, filed on Sep. 16, 2010, provisional application No. 61/492,279, filed on Jun. 1, 2011.

(51) Int. Cl.
*A61F 2/24* (2006.01)

(52) U.S. Cl.
USPC ........................................ 623/2.36

(58) Field of Classification Search
None
See application file for complete search history.

(56) References Cited

U.S. PATENT DOCUMENTS

| 5,306,296 A | 4/1994 | Wright et al. |
| 5,716,370 A | 2/1998 | Williamson, IV et al. |
| 5,855,614 A | 1/1999 | Stevens et al. |
| 6,231,602 B1 | 5/2001 | Carpentier et al. |
| 6,619,291 B2 | 9/2003 | Hlavka et al. |
| 6,629,534 B1 | 10/2003 | St. Goar et al. |
| 6,669,687 B1 | 12/2003 | Saadat |
| 6,893,459 B1 | 5/2005 | Macoviak |
| 7,101,395 B2 | 9/2006 | Tremulis et al. |
| 7,175,660 B2 | 2/2007 | Cartledge et al. |
| 7,238,191 B2 | 7/2007 | Bachmann |
| 7,717,954 B2 | 5/2010 | Solem et al. |

(Continued)

FOREIGN PATENT DOCUMENTS

WO 2011097355 A2 8/2011

OTHER PUBLICATIONS

Notification of Transmittal of the International Search Report and the Written Opinion of the International Searching Authority, or the Declaration for Application PCT/US2011/046659, Int'l Filing Date Aug. 4, 2011.

*Primary Examiner* — Thomas J Sweet
*Assistant Examiner* — Rebecca Preston
(74) *Attorney, Agent, or Firm* — Stoel Rives LLP

(57) ABSTRACT

Apparatus, systems, and methods are provided for repairing heart valves through percutaneous transcatheter delivery and fixation of annuloplasty rings to heart valves. An annuloplasty ring includes an outer hollow member including a plurality of segments. Adjacent segments cooperate with one another to change the outer hollow member from an elongate insertion geometry to an annular operable geometry. The annuloplasty ring also includes an internal anchor member located at least partially within the outer hollow member. The internal anchor member includes a plurality of anchors configured to attach the annuloplasty ring to tissue of a heart valve annulus. The internal anchor member is configured to move the plurality of anchors with respect to a plurality of windows in the outer hollow member to selectively deploy the plurality of anchors through the respective windows.

13 Claims, 46 Drawing Sheets

(56) References Cited

U.S. PATENT DOCUMENTS

| | | |
|---|---|---|
| 7,837,729 B2 | 11/2010 | Gordon et al. |
| 7,988,725 B2 | 8/2011 | Gross et al. |
| 8,182,529 B2 | 5/2012 | Gordon et al. |
| 2003/0050693 A1 | 3/2003 | Quijano et al. |
| 2003/0191528 A1 | 10/2003 | Quijano et al. |
| 2004/0138744 A1* | 7/2004 | Lashinski et al. ............ 623/2.36 |
| 2004/0148021 A1 | 7/2004 | Cartledge et al. |
| 2004/0193191 A1 | 9/2004 | Starksen et al. |
| 2004/0243230 A1 | 12/2004 | Navia et al. |
| 2004/0260394 A1 | 12/2004 | Douk et al. |
| 2005/0033325 A1 | 2/2005 | May et al. |
| 2005/0065550 A1 | 3/2005 | Starksen et al. |
| 2005/0096740 A1 | 5/2005 | Langberg et al. |
| 2005/0203549 A1 | 9/2005 | Realyvasquez |
| 2005/0222678 A1 | 10/2005 | Lashinski et al. |
| 2005/0240200 A1 | 10/2005 | Bergheim |
| 2005/0288778 A1 | 12/2005 | Shaoulian et al. |
| 2005/0288781 A1 | 12/2005 | Moaddeb et al. |
| 2006/0009737 A1 | 1/2006 | Whiting et al. |
| 2006/0161169 A1 | 7/2006 | Nieminen et al. |
| 2006/0184240 A1 | 8/2006 | Jimenez et al. |
| 2006/0195134 A1 | 8/2006 | Crittenden |
| 2006/0241748 A1 | 10/2006 | Lee et al. |
| 2006/0282161 A1 | 12/2006 | Huynh et al. |
| 2007/0016287 A1 | 1/2007 | Cartledge et al. |
| 2007/0027533 A1 | 2/2007 | Douk |
| 2007/0051377 A1 | 3/2007 | Douk et al. |
| 2007/0067027 A1 | 3/2007 | Moaddeb et al. |
| 2007/0080188 A1 | 4/2007 | Spence et al. |
| 2007/0135913 A1 | 6/2007 | Moaddeb et al. |
| 2007/0233239 A1* | 10/2007 | Navia et al. ................... 623/2.37 |
| 2007/0244554 A1 | 10/2007 | Rafiee et al. |
| 2007/0244556 A1 | 10/2007 | Rafiee et al. |
| 2008/0177380 A1 | 7/2008 | Starksen et al. |
| 2008/0262609 A1 | 10/2008 | Gross et al. |
| 2008/0306586 A1 | 12/2008 | Cartledge et al. |
| 2009/0149872 A1 | 6/2009 | Gross et al. |
| 2009/0299470 A1* | 12/2009 | Rao et al. ...................... 623/2.36 |
| 2010/0121433 A1 | 5/2010 | Bolling et al. |
| 2010/0161047 A1 | 6/2010 | Cabiri |
| 2010/0211166 A1 | 8/2010 | Miller et al. |
| 2010/0280605 A1 | 11/2010 | Hammer et al. |
| 2010/0286767 A1 | 11/2010 | Zipory et al. |
| 2011/0093062 A1 | 4/2011 | Cartledge et al. |
| 2011/0106245 A1 | 5/2011 | Miller et al. |
| 2011/0106247 A1 | 5/2011 | Miller et al. |
| 2011/0166649 A1 | 7/2011 | Gross et al. |
| 2011/0257728 A1 | 10/2011 | Kuehn |
| 2011/0282361 A1 | 11/2011 | Miller et al. |
| 2011/0301698 A1 | 12/2011 | Miller et al. |
| 2012/0022557 A1 | 1/2012 | Cabiri et al. |
| 2012/0022644 A1 | 1/2012 | Reich et al. |
| 2012/0123531 A1 | 5/2012 | Tsukashima et al. |

\* cited by examiner

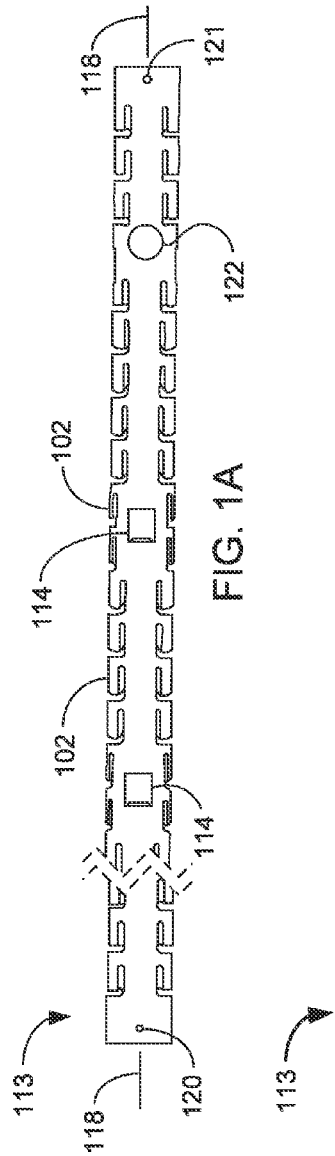
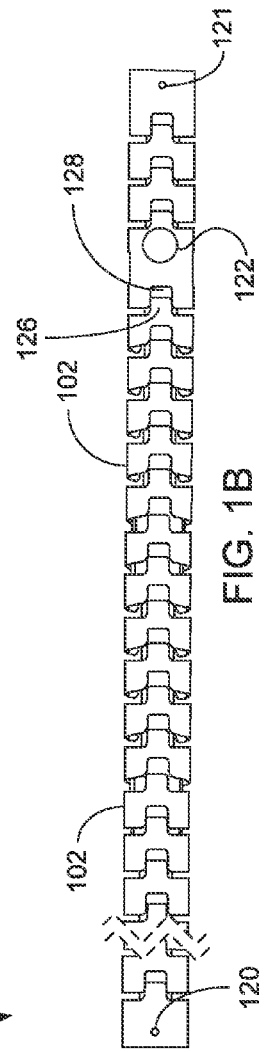
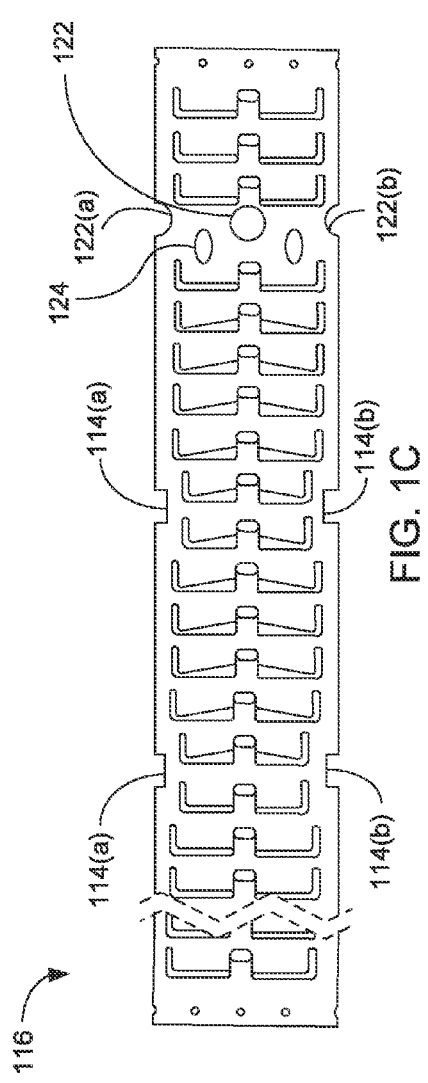

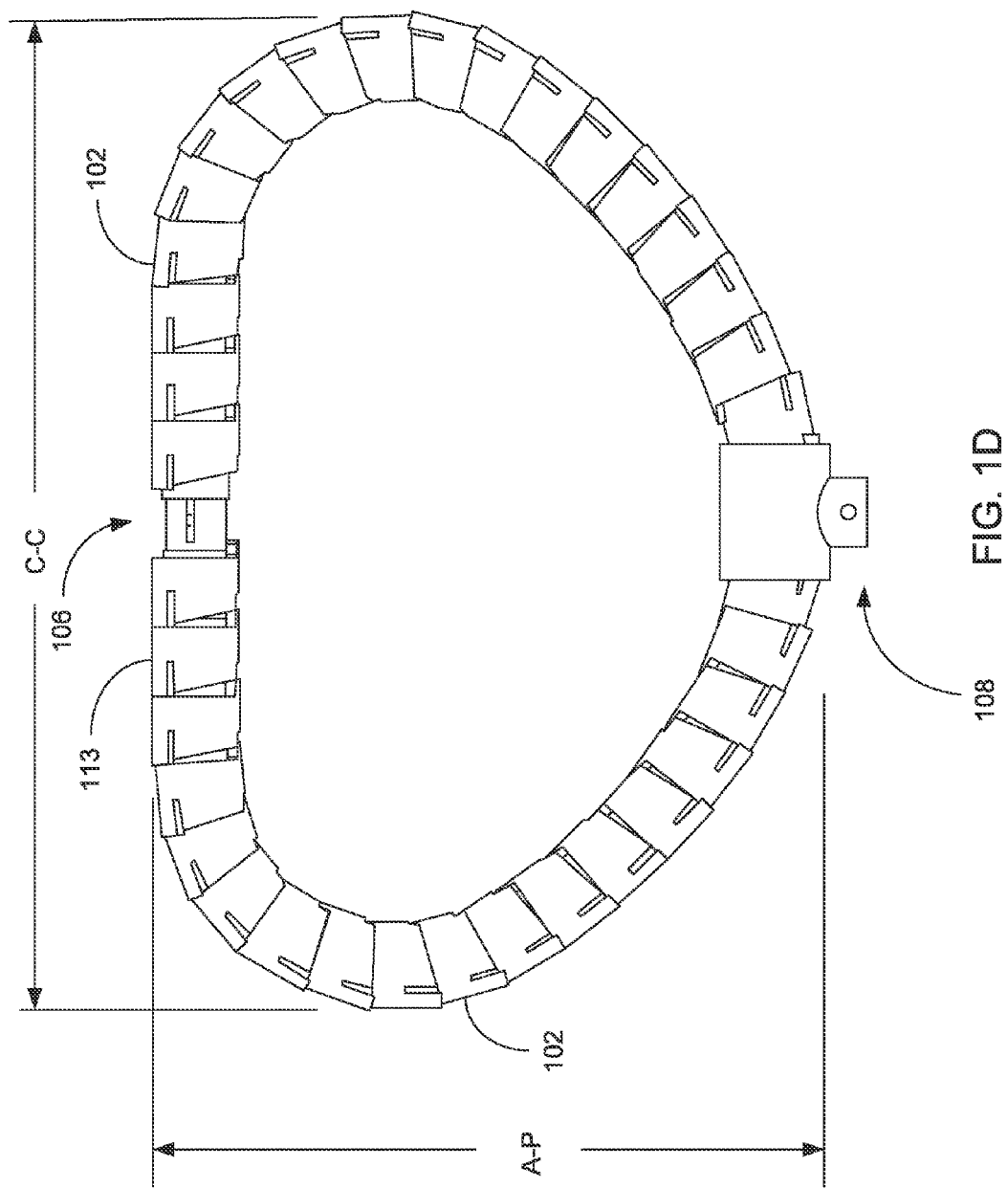

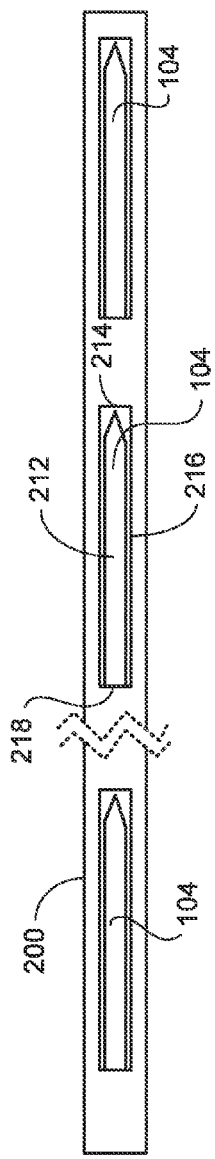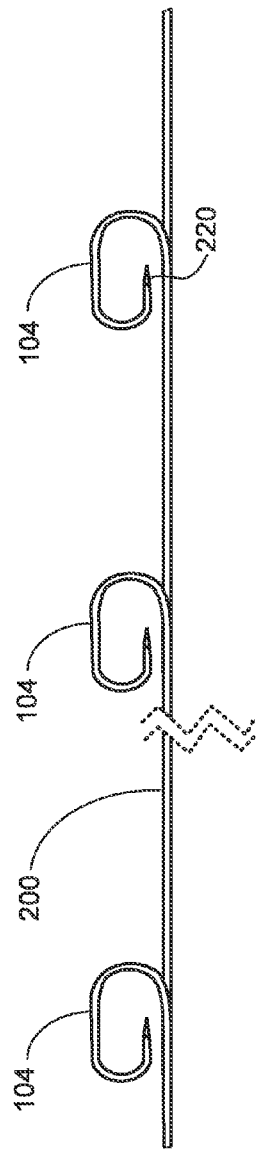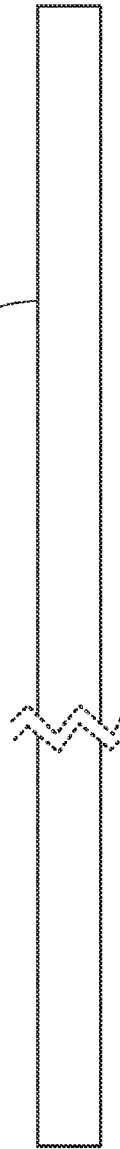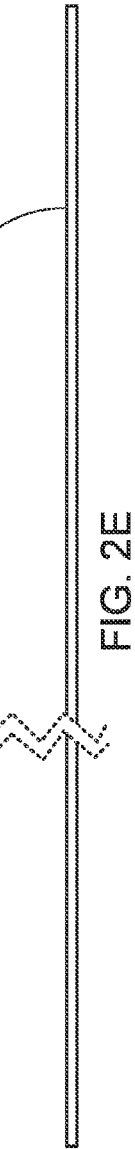

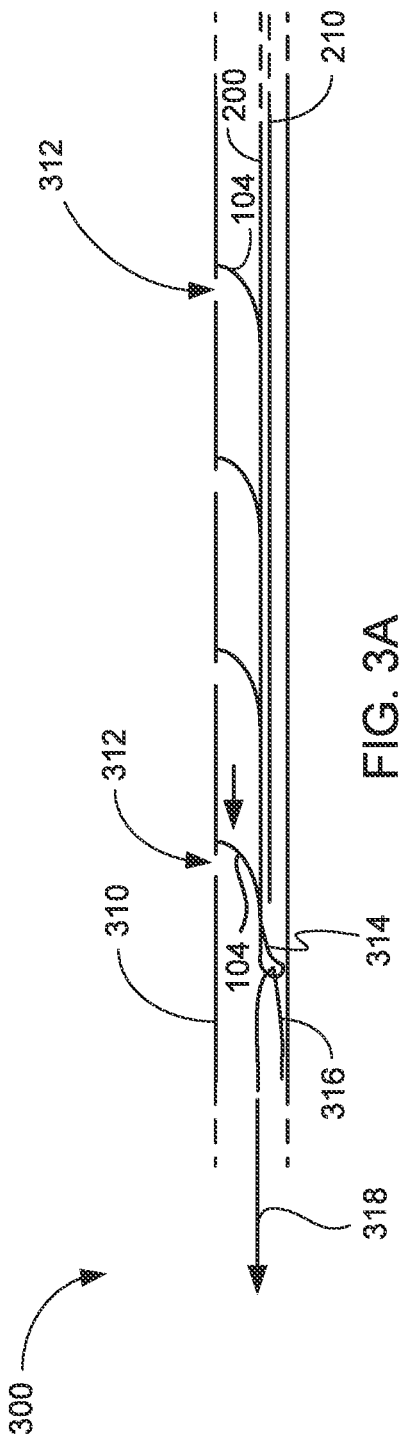
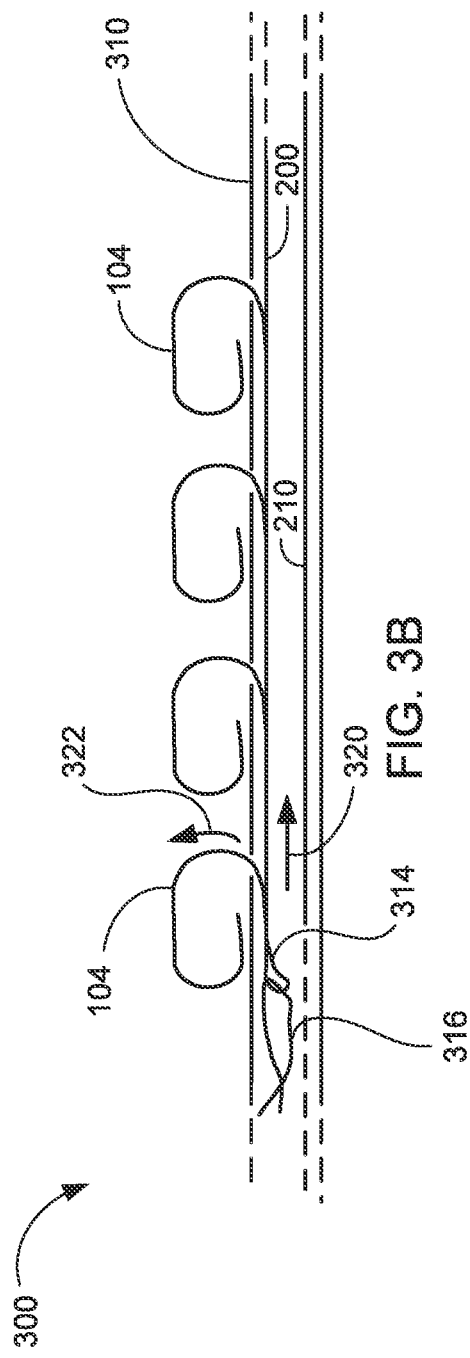

Circuitry in Ring

RF Power Source Circuitry

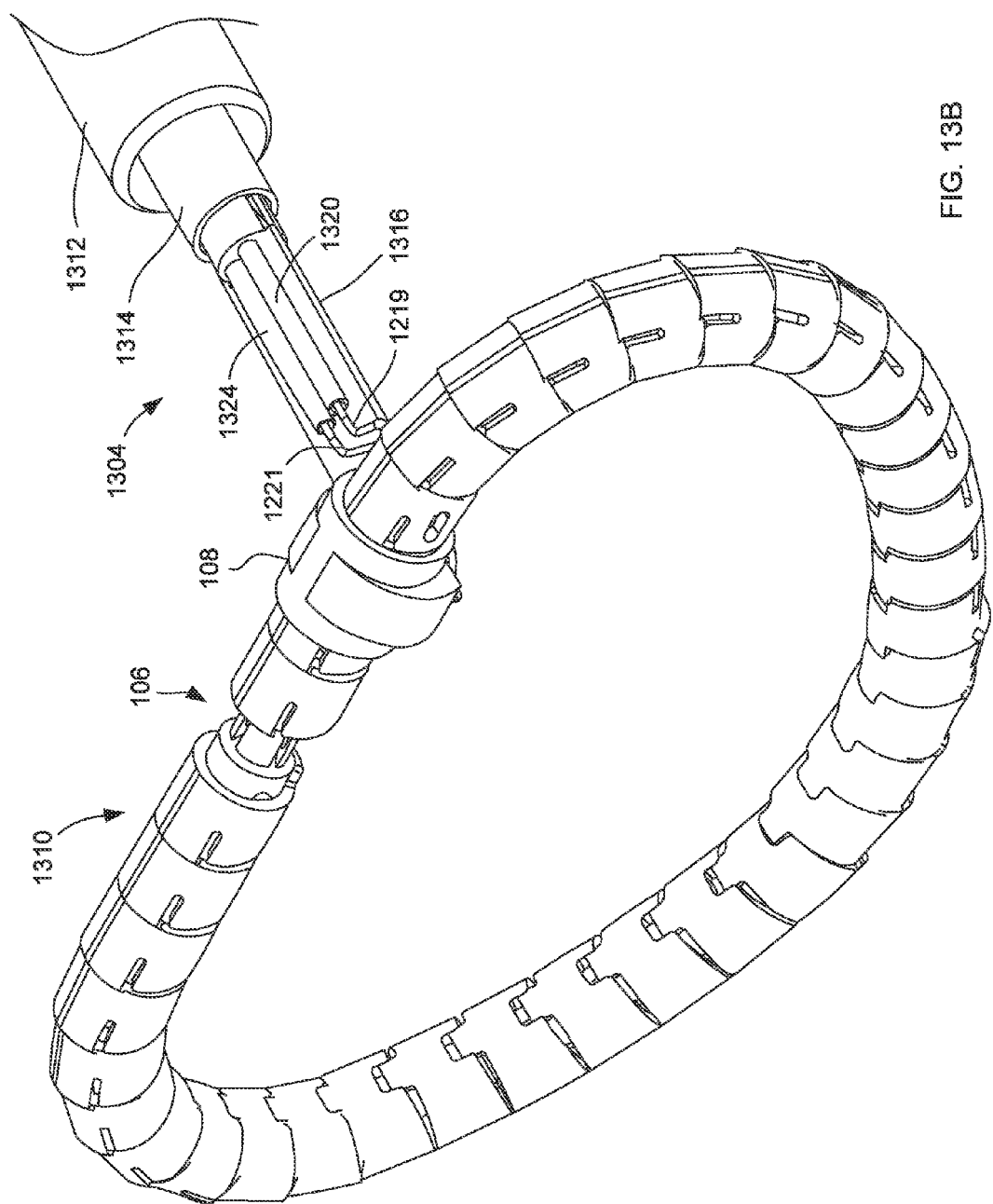

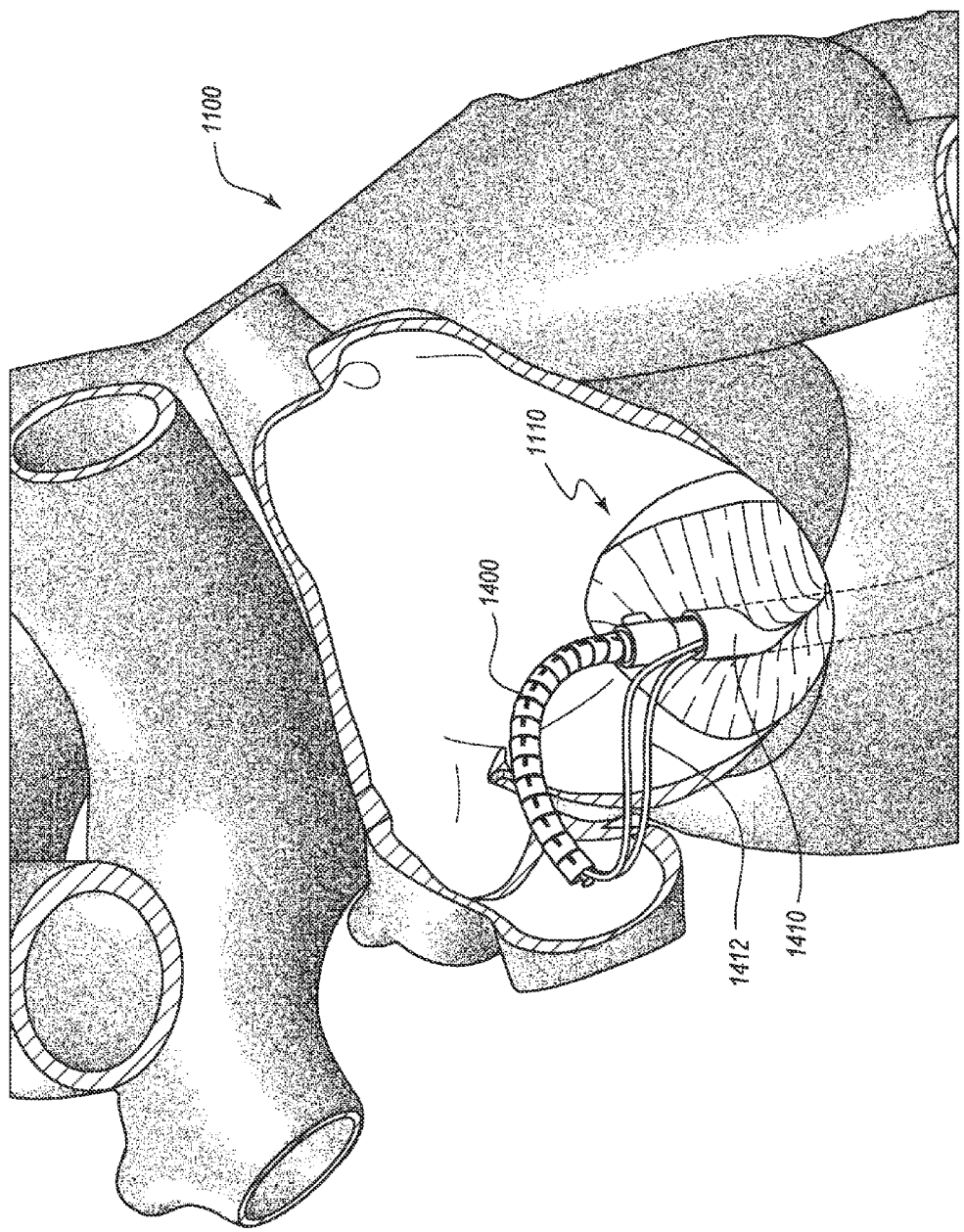

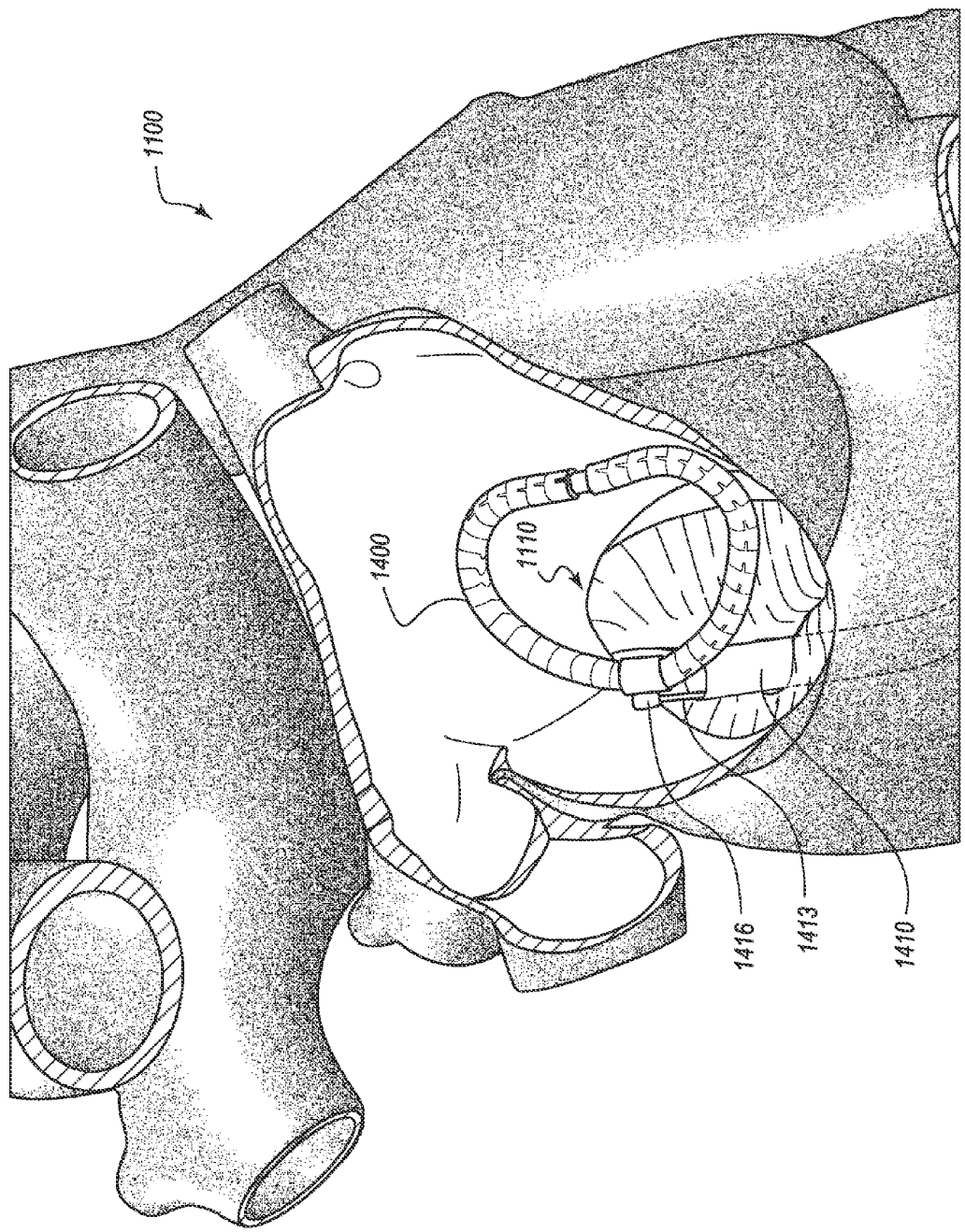

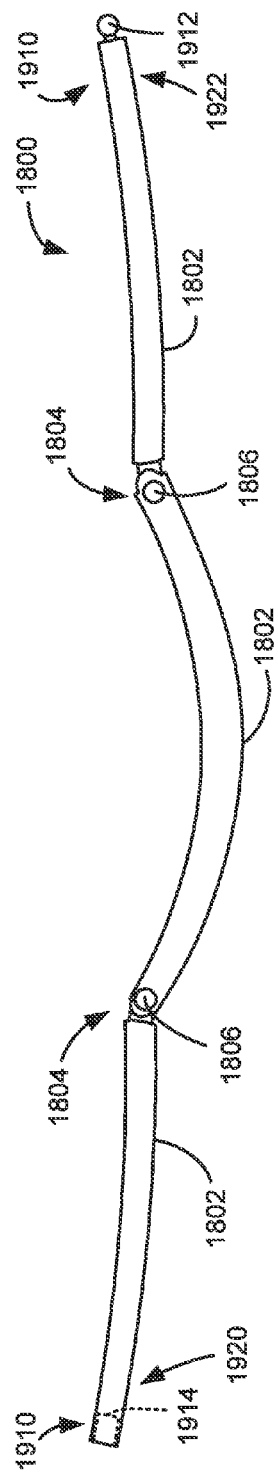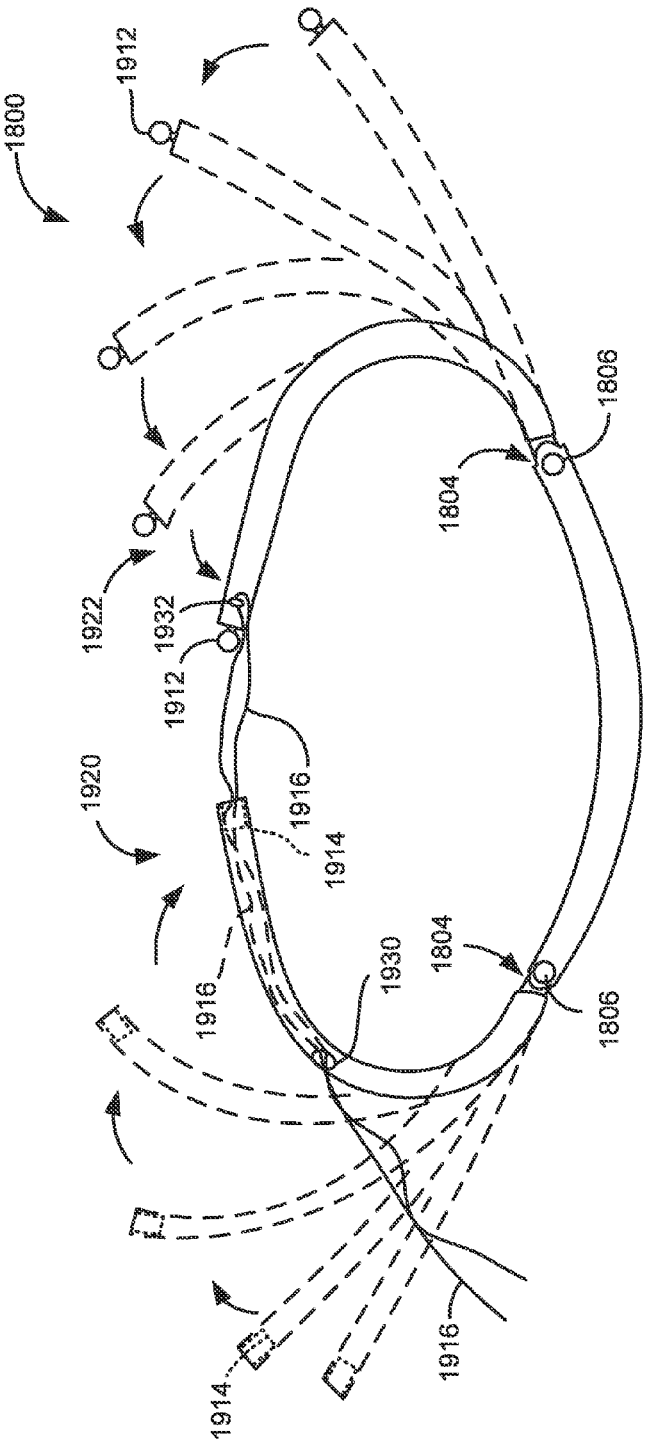

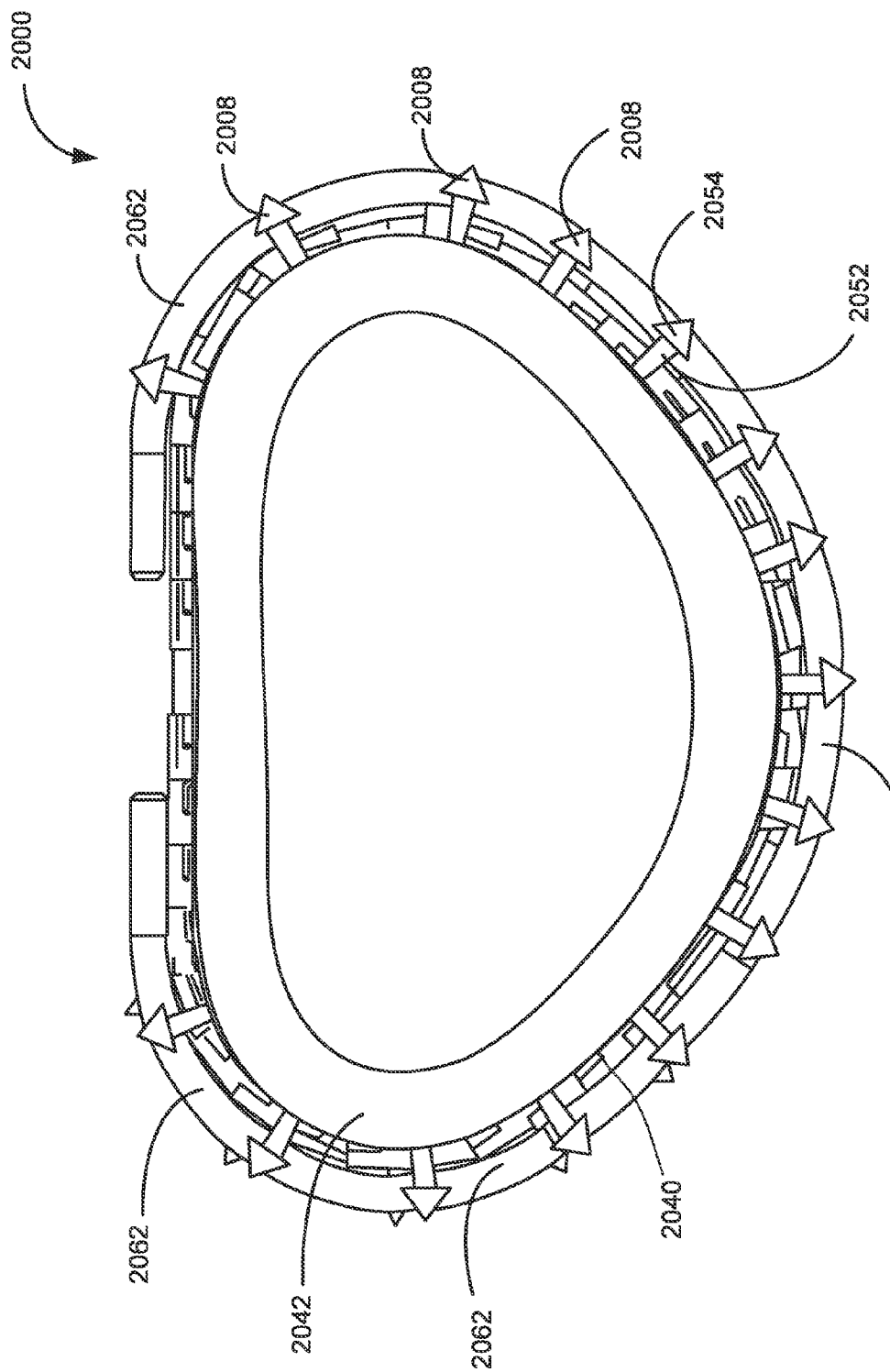

PERCUTANEOUS TRANSCATHETER REPAIR OF HEART VALVES

RELATED APPLICATIONS

This application claims the benefit under 35 U.S.C. §119 (e) of U.S. Provisional Patent Application No. 61/370,754, filed Aug. 4, 2010, and titled "PERCUTANEOUS DELIVERY OF ANNULOPLASTY RINGS TO HEART VALVES," of U.S. Provisional Patent Application No. 61/383,681, filed Sep. 16, 2010, and titled "PERCUTANEOUS DELIVERY OF ANNULOPLASTY RINGS TO HEART VALVES," and of U.S. Provisional Patent Application No. 61/492,279, filed Jun. 1, 2011, and titled "TRANSCATHETER FIXATION OF ANNULOPLASTY RINGS," each of which is hereby incorporated herein by reference in its entirety.

TECHNICAL FIELD

The present disclosure relates to treating and repairing heart valves, and specifically to apparatus, systems, and methods for percutaneous transcatheter delivery and fixation of annuloplasty rings to repair heart valves. Disclosed ring embodiments are configured to be delivered through a catheter using, for example, a trans-septal approach, a retrograde approach, or a trans-apical approach.

BACKGROUND INFORMATION

Heart valve defects, such as regurgitation, may be caused by a relaxation of the tissue surrounding a heart valve (e.g., the mitral valve or tricuspid valve). This causes the valve opening to enlarge, which prevents the valve from sealing properly. Such heart conditions are commonly treated by a procedure during which an annuloplasty ring is fixed or secured around the valve. Cinching or securing the tissue to the ring can restore the valve opening to its approximate original size and operating efficiency.

Typically, annuloplasty rings have been implanted during open heart surgery, so that the annuloplasty ring can be sewn into the valve annulus. Open heart surgery is a highly invasive procedure that requires connecting a heart and lung machine (to pump the patient's blood and breathe for the patient), stopping the patient's heart, and cutting open the thoracic cavity and heart organ. The procedure can expose the patient to high risk of infection and may result in a long and difficult recovery. The recovery can be particularly difficult for patients in less than optimal health due to the effects of suffering from a heart valve defect such as regurgitation.

SUMMARY OF THE DISCLOSURE

Disclosed herein are apparatus, systems, and methods for repairing heart valves through percutaneous transcatheter delivery and fixation of annuloplasty rings to heart valves.

In one embodiment, an annuloplasty ring includes an outer hollow member including a plurality of segments. Adjacent segments cooperate with one another to change the outer hollow member from an elongate insertion geometry to an annular operable geometry. The annuloplasty ring also includes an internal anchor member located at least partially within the outer hollow member. The internal anchor member includes a plurality of anchors configured to attach the annuloplasty ring to tissue of a heart valve annulus. The internal anchor member is configured to move the plurality of anchors with respect to a plurality of windows in the outer hollow member to selectively deploy the plurality of anchors through the respective windows.

In certain embodiments, methods are disclosed for percutaneous transcatheter repair of a heart valve using the segmented annuloplasty ring.

In addition, or in other embodiments, a delivery system is disclosed for percutaneous transcatheter delivery of the segmented annuloplasty ring.

BRIEF DESCRIPTION OF THE DRAWINGS

Understanding that drawings depict only certain embodiments and are not therefore to be considered to be limiting in nature, non-limiting and non-exhaustive embodiments of the disclosure are described and explained with additional specificity and detail through the use of the accompanying drawings.

FIGS. 1A and 1B are schematic diagrams illustrating a shape memory hypotube cut to form a plurality of segments for use as an outer tube of a segmented annuloplasty ring according to one embodiment.

FIG. 1C is a schematic diagram illustrating a cutting pattern used for laser processing the hypotube shown in FIGS. 1A and 1B.

FIG. 1D is a schematic diagram illustrating the shape memory hypotube shown in FIGS. 1A and 1B in an annular (D-shaped) operable geometry.

FIG. 2B is a schematic diagram illustrating a top view of the anchors cut into the internal anchor ribbon shown in FIG. 2A in the elongate insertion geometry according to one embodiment.

FIG. 2C is a schematic diagram illustrating a side view of the internal anchor ribbon in the elongate insertion geometry and the anchors in a curled or curved deployed configuration according to one embodiment.

FIG. 2D is a schematic diagram illustrating a top view of an internal glide ribbon shown in FIG. 2A in an elongate insertion geometry according to one embodiment.

FIG. 2E is a schematic diagram illustrating a side view of the internal glide ribbon shown in FIG. 2D.

FIGS. 3A and 3B are simplified schematics illustrating cross-section side views of an annuloplasty ring before (FIG. 3A) and after (FIG. 3B) deployment of the anchors shown in FIG. 2C according to one embodiment.

FIGS. 13A, 13B, 13C, 13D, 13E, 13F, and 13G are schematic diagrams illustrating the front of the delivery system shown in FIG. 12A according to certain embodiments.

FIGS. 14A, 14B, 14C, 14D, 14E, 14F, and 14G are schematic diagrams illustrating perspective, partially cross-section views of a heart during the introduction and affixation of a segmented annuloplasty ring to the annulus of the mitral valve according to certain embodiments.

FIG. 19A is a schematic diagram illustrating the percutaneous transcatheter annuloplasty ring of FIG. 18 in an insertion geometry according to one embodiment.

FIG. 19B is a schematic diagram of the percutaneous transcatheter annuloplasty ring transitioning from the insertion geometry shown in FIG. 19A to the operable geometry shown in FIG. 18 according to one embodiment.

FIG. 20C is a schematic diagram of the annuloplasty ring of FIG. 20A with the anchors in an affixation configuration protruding away from the annuloplasty ring according to one embodiment.

DETAILED DESCRIPTION OF PREFERRED EMBODIMENTS

While there are flexible rings currently on the market, surgeons generally prefer rigid and semi-rigid rings for valve repair to treat ischemic and functional mitral valve regurgitation. Rigid and semi-rigid rings, unfortunately, do not lend themselves to being delivered into the heart through a catheter. The present disclosure provides systems and methods for repairing heart valves through percutaneous transcatheter delivery and fixation of annuloplasty rings to heart valves. The embodiments of annuloplasty rings can be configured in both an elongate insertion geometry that can be inserted into a catheter tube and an operable geometry providing a curved and rigid or semi-rigid annular shape.

In certain embodiments, an annuloplasty ring is delivered percutaneously to the mitral and/or tricuspid valve annulus of the heart. The disclosed embodiments apply, for example, to trans-septal, retrograde, or trans-apical approaches for delivering annuloplasty rings to an annulus of a heart valve. For delivery of rings into the mitral valve, percutaneous delivery may use a retrograde approach from the femoral artery, an antegrade approach via a trans-septal entry, or a trans-apical approach through the base or apex of the heart through the left ventricle to the left atrium. Delivery of rings to the tricuspid valve may include an approach from the inferior or superior vena cava.

Certain annuloplasty rings disclosed herein are small and flexible enough to be percutaneously delivered, but can be put into a rigid or semi-rigid ring shape and then securely anchored into the heart valve annulus without having to open up the chest. Disclosed embodiments include segmented annuloplasty rings, delivery systems, and methods for anchoring and cinching the annuloplasty ring around the valve annulus.

Example Ring Embodiments with Curved Anchors

Figure 1:
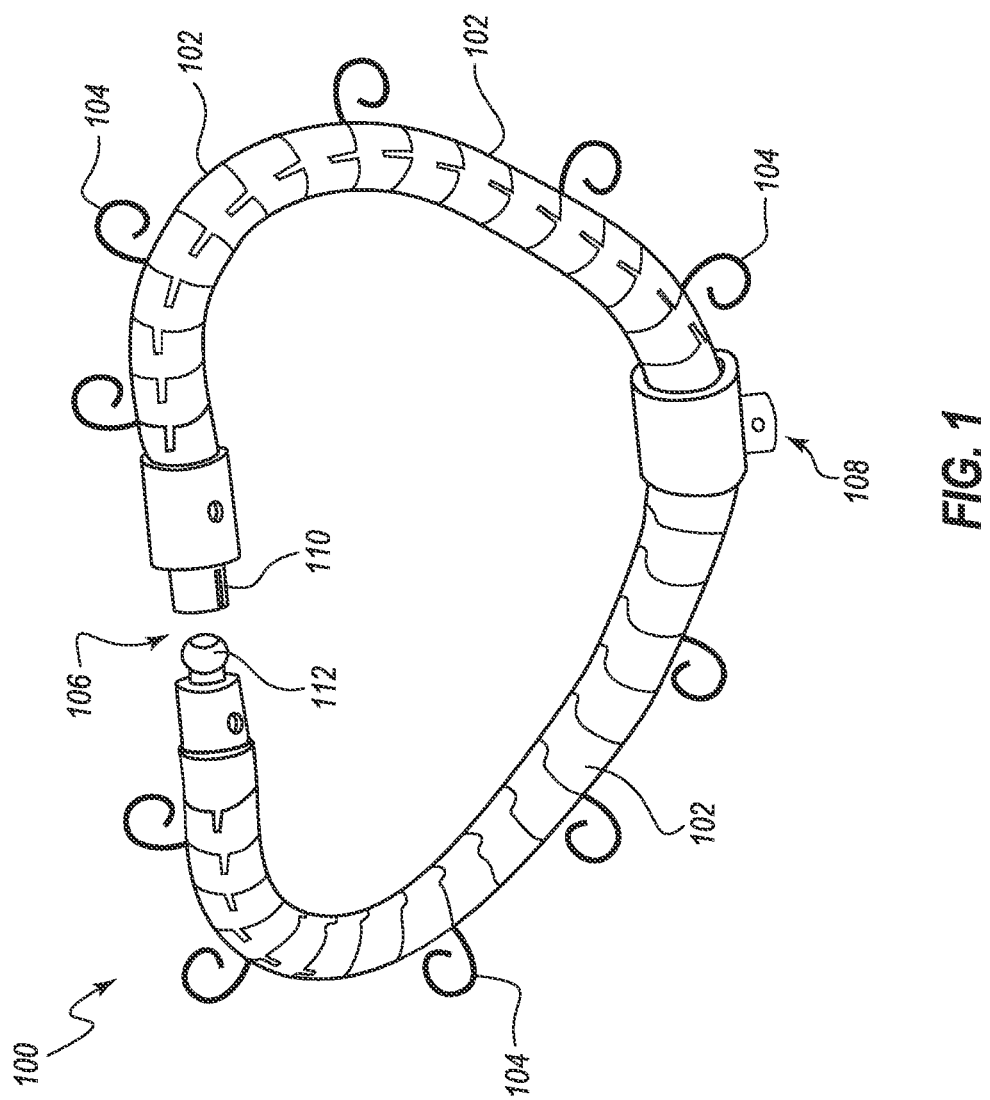
FIG. 1 is a simplified schematic diagram illustrating a perspective view of a segmented annuloplasty ring according to one embodiment.

FIG. 1 is a simplified schematic diagram illustrating a perspective view of a segmented annuloplasty ring 100 according to one embodiment. The segmented annuloplasty ring 100 includes a plurality of segments 102, a plurality of anchors 104, a ring closure lock 106, and a pivot 108. In FIG. 1, as well as in other embodiments disclosed herein, the plurality of segments 102 are arranged in a "D-shape" in the operable geometry (e.g., when implanted around the annulus). The D-shaped ring 100 has a certain geometrical ratio that is in conformance with the anatomical geometry of the human mitral valve annulus. For example, as discussed below with respect to FIG. 1D, the ratio in certain embodiments of the anterior-posterior (A-P) distance to the commissure-commissure (C-C) distance of the ring 100 when implanted is in a range between about 0.60 and about 0.70. In one embodiment, the implanted ratio of the A-P distance to the C-C distance is about 0.62. Artisans will recognize from the disclosure herein, however, that other operable geometries may also be used. For example, circular or oval operable geometries may be used.

In addition to the operable geometry, the plurality of segments 102 allow the ring 100 to be placed in an elongate insertion geometry such that the ring 102 can be inserted through a catheter into the heart. As discussed in detail below, in certain embodiments, the segmented annuloplasty ring 100 includes a shape memory (e.g., Nitinol) hypotube into which the plurality of segments 102 are laser cut. The shape memory hypotube is heat set to a "memorized" annular shape (e.g., the D-shaped operable geometry). The shape memory hypotube is superelastic such that applying sufficient stress places the plurality of segments 102 into the elongate insertion geometry and releasing the stress allows the plurality of segments 102 to resume the D-shaped operable geometry.

The plurality of anchors 104 are configured to secure the segmented annuloplasty ring 100 to the annulus of the heart valve. In certain embodiments, the anchors 104 are sufficient such that additional suturing of the segmented annuloplasty ring 100 to the valve annulus is not needed. In FIG. 1, the anchors 104 are curved in the illustrated deployed configuration. Anchors in other embodiments may include other shapes, such as linear or helical deployed configurations. In certain embodiments, the anchors 104 include a shape memory material (e.g., Nitinol) that is heat set to a deployed configuration (e.g., linear, helical, or curved configuration shown in FIG. 1). Artisans will recognize from the disclosure herein that combinations of different deployed configurations may also be used.

The anchors 104 are superelastic such that applying sufficient stress places the anchors 104 into an introduction configuration and releasing the stress allows the anchors 104 to resume their respective deployed configurations. In certain embodiments, the anchors 104 lay flat against the plurality of segments 102 in the introduction configuration during insertion of the ring 100 through the catheter. As discussed below, in other embodiments, the anchors 104 are retracted inside the segmented ring 100 in the introduction configuration during insertion of the ring 100 through the catheter. In such embodiments, the anchors 104 may be selectively deployed at a desired time (e.g., after the segmented ring 100 is properly positioned against the annulus of the heart valve). In certain embodiments, the superelastic property of the anchors 104 is used to self-propel the anchors 104 into the annulus of the heart valve.

As discussed below, the pivot 108 is used to automatically rotate the segmented annuloplasty ring 100 after it exits the catheter within the heart to align the plane of the ring 100 (in the annular operable geometry) with the plane of the heart valve. The ring 100 is pushed from the catheter in a direction that is substantially perpendicular to the plane of the heart valve (e.g., parallel to the direction of blood flow). Upon exiting the catheter, the pivot 108 rotates the ring 100 to allow the ring 100 to be properly positioned against the annulus. In one embodiment, the anchors 104 are deployed before pressing the ring 100 against the valve annulus (e.g., a balloon may be used to drive the deployed anchors into the tissue). In other embodiments, the ring 100 is pressed against the valve annulus (e.g., using a balloon) before deploying the anchors 104 and the act of deploying the anchors 104 drives the anchors 104 into the tissue. Fluoroscopy, ultrasound, and/or other imaging techniques may be used to assist in proper positioning of the ring 100 against the heart valve annulus.

The ring closure lock 106 is used to secure the two open ends of the segmented annuloplasty ring 100 to form a closed ring. As shown in FIG. 1, in certain embodiments, the ring closure lock 106 includes a female snap 110 and a male snap 112. As discussed below, the segmented annuloplasty ring 100 may be "snap locked" using wires or sutures to pull the male snap 112 into the female snap 110. In certain embodiments, a gap (e.g., between about 3 mm and 5 mm) is left between the female snap 110 and the male snap 112 after the anchors 104 are deployed within the tissue of the valve annulus. Then, the two ends are snapped together to provide cinching of the valve annulus. This cinching is similar to a technique used by surgeons during open heart surgery (e.g., using sutures) to draw the valve annulus into a smaller or improved shape that reduces regurgitation of blood back through the valve.

Although not shown in FIG. 1, certain ring embodiments include a selectively adjustable member (discussed below) for changing the size and/or shape of the segmented annuloplasty ring 100 postoperatively to compensate for changes in the size of the heart and/or the treated heart valve. Also not shown in FIG. 1, certain ring embodiments include a cover disposed about the entire circumference of the segmented ring 100, or selected portions thereof. For example, in certain embodiments, the cover is disposed so as to enclose the plurality of segments 102, while leaving uncovered at least portions of the ring closure lock 106 (to permit snapping the lock together) and the pivot 108 (to allow access thereto during insertion of the ring 100). The cover may include openings aligned with windows (discussed below) in the plurality of segments 102 through which the plurality of anchors 104 are deployed. In other embodiments, the plurality of anchors 104 are configured to puncture through the cover during deployment. The cover may include a biocompatible material such as Dacron®, woven velour, polyurethane, polytetrafluoroethylene (PTFE), heparin-coated fabric, or the like. In other embodiments, the cover includes a biological material such as bovine or equine pericardium, homograft, patient graft, or cell-seeded tissue.

FIGS. 1A and 1B are schematic diagrams illustrating a shape memory hypotube 113 cut to form a plurality of segments 102 for use as an outer tube (also referred to herein as an "outer hollow member") of a segmented annuloplasty ring according to one embodiment. FIG. 1A is a plan view of a first side of the hypotube 113 in which a plurality of anchor deployment windows 114 are cut. FIG. 1B is a plan view of a second side of the hypotube 113 that is opposite the windows 114 shown in FIG. 1A. For illustrative purposes, FIG. 1C is a schematic diagram illustrating a cutting pattern 116 used for laser processing the hypotube 113 shown in FIGS. 1A and 1B. While FIGS. 1A and 1B show respective (opposite) sides of the hypotube 113, the cutting pattern 116 corresponds to the entire hypotube 113 as if the hypotube were cut along an axis 118 of the surface shown in FIG. 1A and unrolled. Thus, for example, each window 114 shown in FIG. 1A is shown in FIG. 1C as being split between a first half of the window 114(*a*) and a second half of the window 114(*b*).

The hypotube 113 includes a through hole 120, 121 at each end (or two perpendicular through holes at each end according to FIG. 1C) to allow one or more pins (not shown) to couple the male and female components of the ring closure lock 106 to respective ends of the hypotube 113. The hypotube 113 also includes a through hole 122 (the opening 122 shown in FIG. 1A being represented in FIG. 1C as 122(*a*) and 122(*b*)) for another pin (not shown) for coupling the pivot 108 to the hypotube 113. As shown in FIG. 1C, the hypotube 113 may also include a window 124 (passing vertically through the hypotube 113 with respect to the views shown in FIGS. 1A and 1B) that allows one or more lines or sutures (not shown) to exit the hypotube 113. As discussed below, the sutures are used to snap lock the ring and/or to deploy the anchors 104.

In FIGS. 1A and 1B, the hypotube 113 is shown in the elongate insertion geometry. FIG. 1D is a schematic diagram illustrating the shape memory hypotube 113 shown in FIGS. 1A and 1B in an annular (D-shaped) operable geometry. In FIG. 1D, the ring closure lock 106 and the pivot 108 are also shown. For reference, the first side shown in FIG. 1A corresponds to the outer circumference of the ring shown in FIG. 1D, and the second side shown in FIG. 1B corresponds to the inner circumference of the ring shown in FIG. 1D. FIG. 1D shows an anterior-posterior (A-P) direction and a commissure-commissure (C-C) direction, corresponding to the anatomical structure of a human mitral-valve annulus. As discussed above, in certain embodiments, the implant size of the D-shaped hypotube 113 in the operable geometry has ratio of A-P distance to C-C distance in range between about 0.60 to about 0.70. By way of example only, and not by limitation, the table below provides some example dimensions.

| Ring Size | Implant Shape (mm) | | |
|---|---|---|---|
| | C-C | A-P | Ratio |
| 28 | 28.00 | 17.36 | 0.62 |
| 30 | 30.00 | 18.60 | 0.62 |
| 32 | 32.22 | 19.84 | 0.62 |
| 34 | 34.00 | 21.08 | 0.62 |
| 36 | 36.00 | 22.32 | 0.62 |

The cutting pattern 116 shown in FIG. 1C defines the configuration of the plurality of segments 102 and how the segments 102 interact with adjacent segments as the hypotube transitions from the elongate insertion geometry shown in FIGS. 1A and 1B to the annular operable geometry shown in FIG. 1C. As shown in FIG. 1B, the hypotube in this example embodiment includes a "tongue and groove" pattern wherein a tongue 126 of one segment interfaces with a groove 128 of an adjacent segment as the inner circumference of the ring is formed. The cutting pattern 116 provides rigidity to the hypotube 113 in the annular operable geometry, allows the hypotube 113 to easily transition from the elongate insertion geometry to the annular operable geometry, and substantially closes gaps between the segments 102 in the annular operable geometry.

Figure 2A:
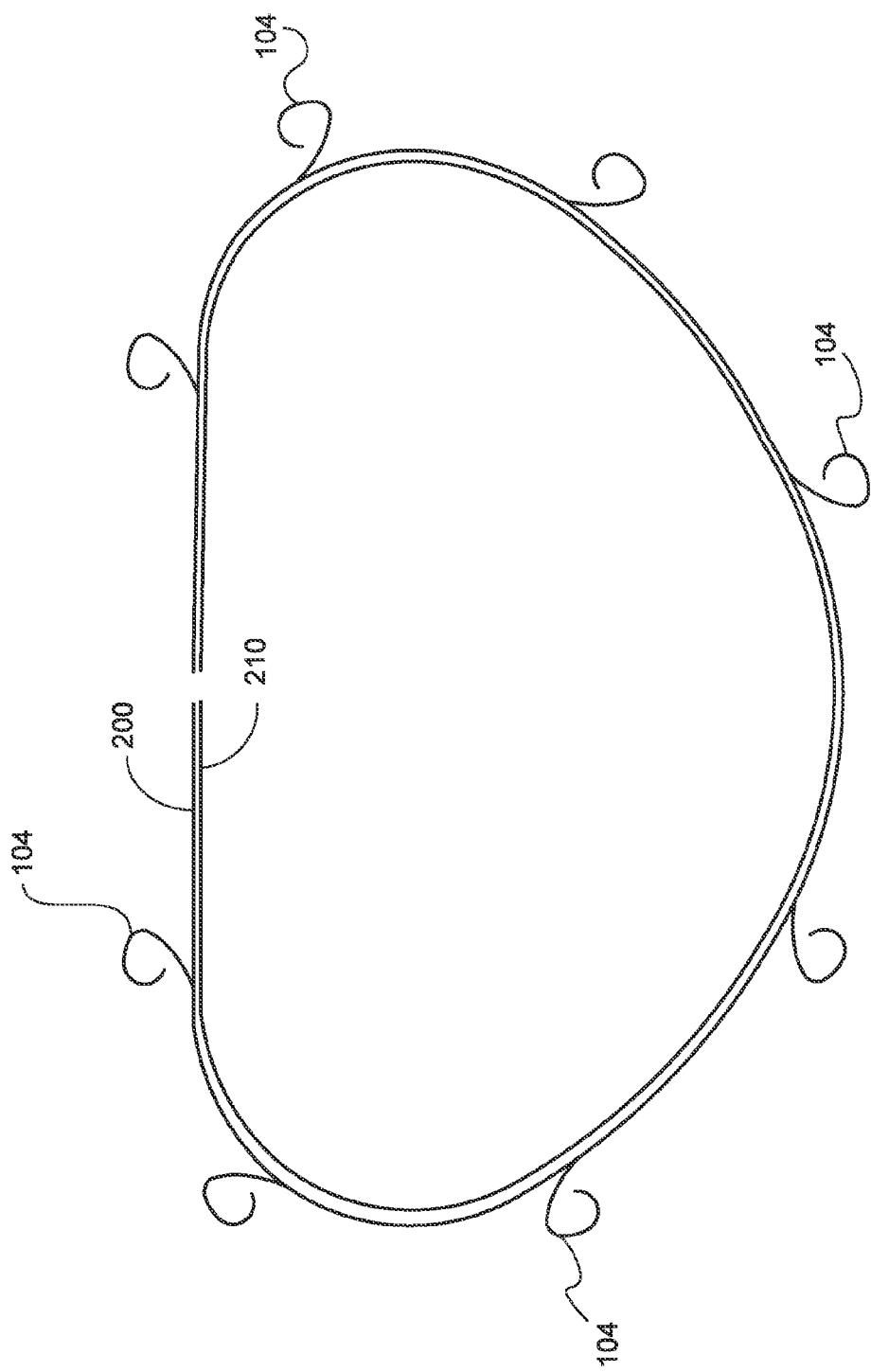
FIG. 2A is a simplified schematic diagram illustrating a side view of an internal anchor ribbon including the curved anchors shown in FIG. 1 according to one embodiment.

In certain embodiments, deployment of the anchors 104 is accomplished using an internal anchor member that is selectively movable within the hollow tube formed by the plurality of segments 102. For example, FIG. 2A is a simplified schematic diagram illustrating a side view of an internal anchor ribbon 200 including the curved anchors 104 shown in FIG. 1 according to one embodiment. The curved anchors 104 may be affixed (e.g., laser welded) to the internal anchor ribbon 200 or directly cut into the internal anchor ribbon 200 (as discussed with respect to FIGS. 2B and 2C). Like the anchors 104, the internal anchor ribbon 104 includes a superelastic shape memory material (e.g., Nitinol) that is heat set to the same memorized annular shape as the plurality of segments 102 (shown in FIGS. 1 and 2A as D-shaped).

The internal anchor ribbon 200 may be slid (e.g., using wires or sutures accessible through the catheter) within the hollow tube formed by the plurality of segments 102 of the ring 100. To reduce friction between the internal anchor ribbon 200 and the plurality of segments 102, certain ring embodiments include an internal glide ribbon 210. The internal glide ribbon 210 may includes a low-friction material (e.g., as a coating or covering) such as PTFE or other polymer. In addition, or in other embodiments, the internal glide ribbon 210 includes a superelastic shape memory material (e.g., Nitinol) that is heat set to the same memorized annular shape as the plurality of segments 102 (shown in FIGS. 1 and 2A as D-shaped). Thus, certain embodiments include three D-shaped superelastic members (the outer tube of segments 102, the internal anchor ribbon 200, and the internal glide ribbon 210), which cooperate to increase the rigidity of the ring 100.

FIG. 2B is a schematic diagram illustrating a top view of the anchors 104 cut into the internal anchor ribbon 200 shown in FIG. 2A in the elongate insertion geometry according to one embodiment. In this example, a laser is used to cut the anchors 104 along a first side 212, a second side 214 (e.g., in a pointed or tip shape), and a third side 216, while leaving a fourth side 218 of the anchor 104 uncut and attached to the internal anchor ribbon 200. After cutting, the anchors 104 are heat set to the desired memorized shape for the deployed configuration. For example, FIG. 2C is a schematic diagram illustrating a side view of the internal anchor ribbon 200 in the elongate insertion geometry and the anchors 104 in a curled or curved deployed configuration according to one embodiment. The amount of curvature in the deployed configuration of the anchors 104 may depend on the particular application. In the example shown in FIG. 2C, the anchors 104 fold back on themselves such that the prong or tip 220 points parallel to or away from the internal anchor ribbon 200. FIG. 2D is a schematic diagram illustrating a top view of the internal glide ribbon 210, and FIG. 2E is a schematic diagram illustrating a side view of the internal glide ribbon 210, in the elongate insertion geometry according to one embodiment.

FIGS. 3A and 3B are simplified schematics illustrating cross-section side views of an annuloplasty ring 300 before (FIG. 3A) and after (FIG. 3B) deployment of the anchors 104 shown in FIG. 2C according to one embodiment. For illustrative purposes, the ring 300 in FIGS. 3A and 3B is shown in an elongate insertion geometry. Artisans will recognize from the disclosure herein, however, that the anchors 104 are generally deployed when the ring 300 is in the annular operable geometry.

The illustrated ring 300 includes an outer tube 310 (e.g., formed by the plurality of segments 102 shown in FIG. 1) including a plurality of anchor deployment windows 312. During the manufacturing of the ring 300, and before the ring 300 is loaded into the catheter, the internal anchor ribbon 200 and the internal glide ribbon 210 are inserted into the outer tube 310 in a position where the anchors 104 are prevented from exiting through the windows 312. As shown in FIG. 3A, inserting the internal anchor ribbon 200 into the outer tube 300 prevents the anchors from assuming their fully curved deployed configuration.

For deploying the anchors 104, the internal anchor ribbon 200 may include (or may be attached to) a hook or loop 314 for engaging a wire or suture 316 that may be pulled by a user through the catheter (e.g., in the direction of arrow 318 in FIG. 3A) to move the tip of each anchor 104 to a corresponding window 312. In certain embodiments, the anchors 104 and windows 312 are arranged such that the tip of each anchor 104 reaches its respective window 312 at substantially the same time as the other anchor/window pairs. As shown in FIG. 3B, once the tips of the anchors 104 reach the respective windows 312, the superelasticity of the anchors 104 propels the internal anchor ribbon 200 in the opposite direction (as indicated by arrow 320) as the anchors 104 spring out the windows 312 (as indicated by arrow 322) to resume their curved configurations, which drives the anchors 104 into surrounding tissue (e.g., the heart valve annulus). Thus, the superelasticity of the anchors 104 allows the anchors 104 to be self-propelled into the tissue adjacent or proximate to the ring 300.

Figure 4A:
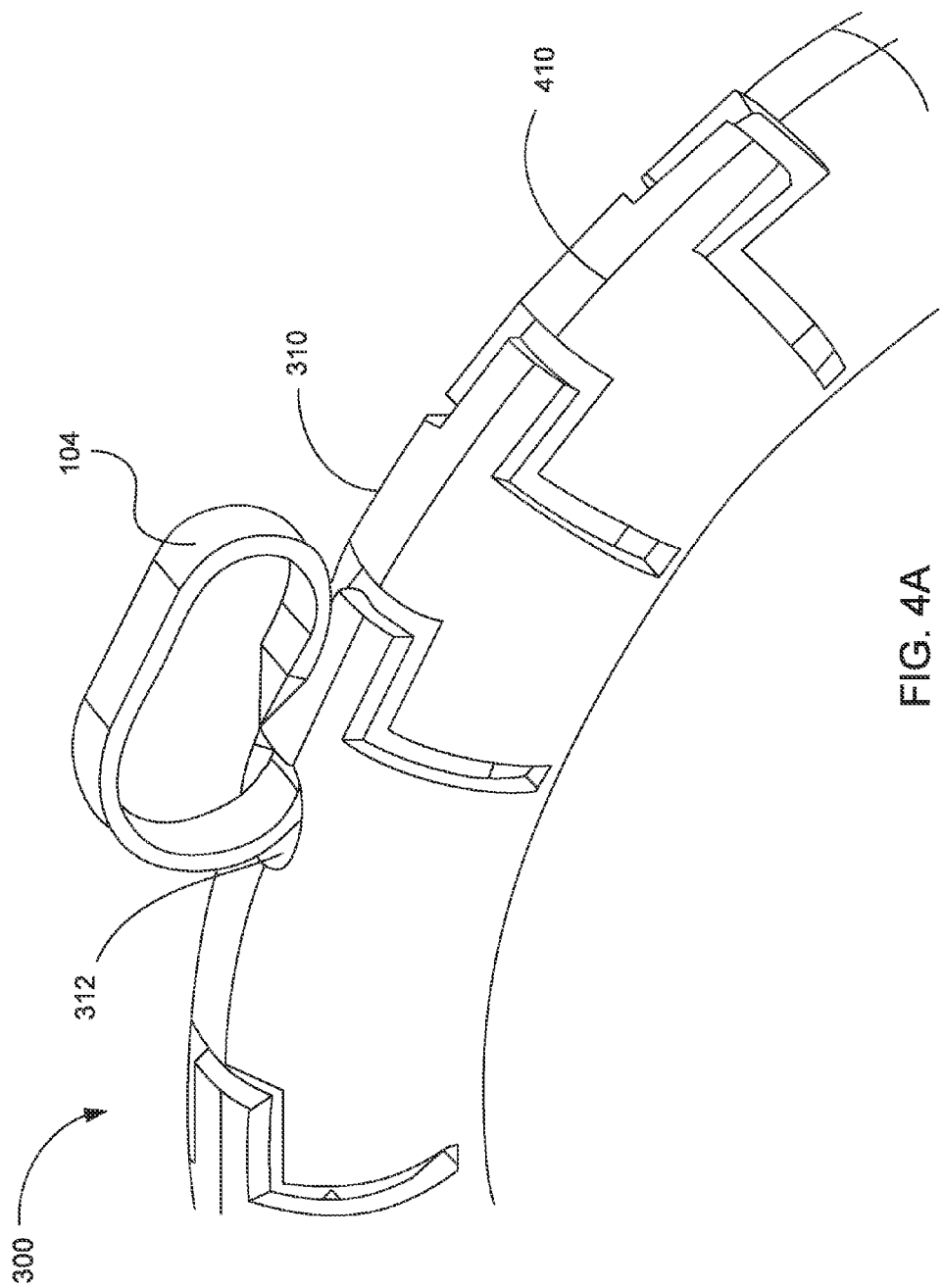
FIG. 4A is a schematic diagram illustrating a perspective view of a portion of the annuloplasty ring shown in FIGS. 3A and 3B with a deployed curved anchor according to one embodiment.

FIG. 4A is a schematic diagram illustrating a perspective view of a portion of the annuloplasty ring 300 shown in FIGS.

Figure 4B:
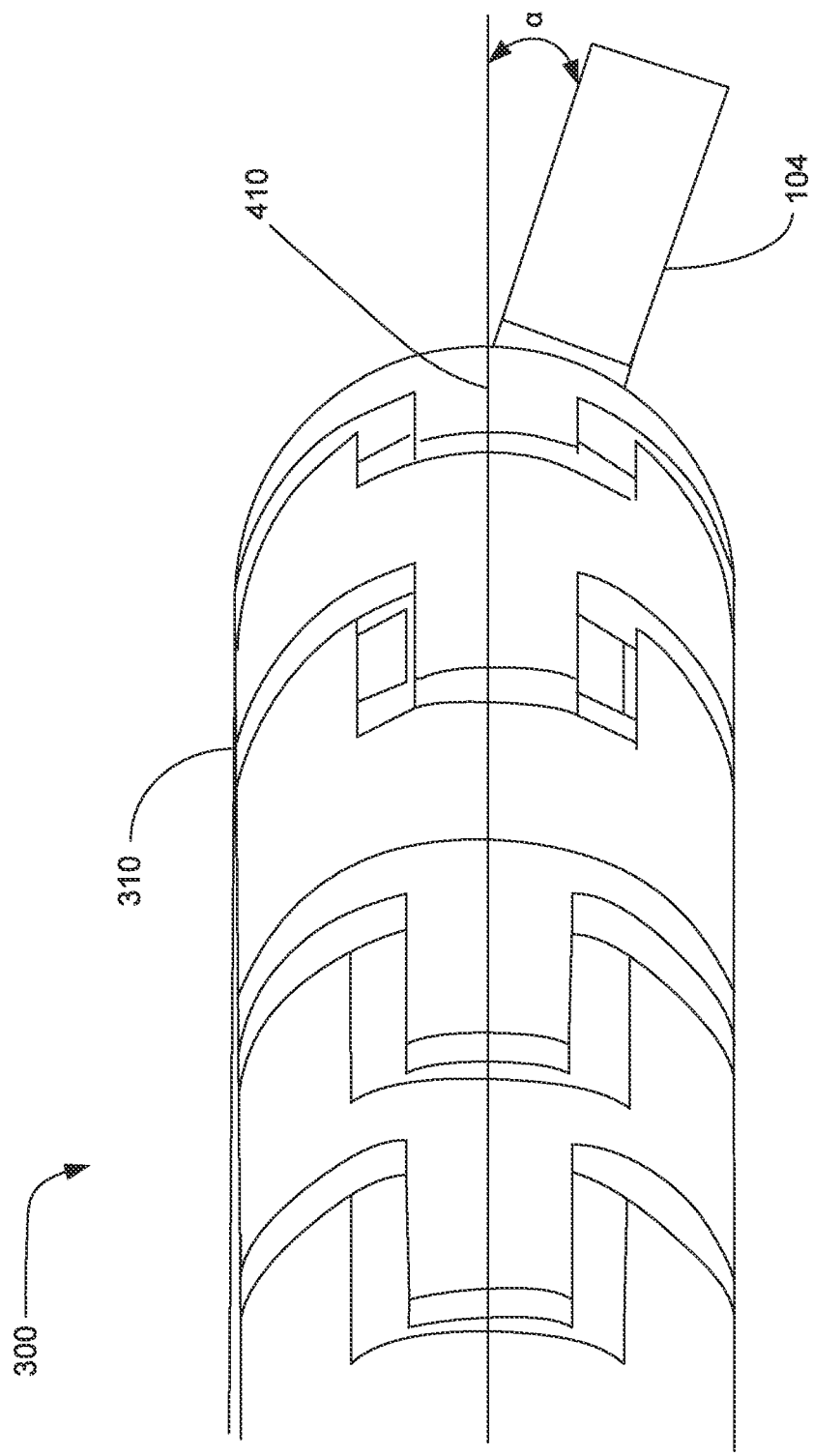
FIG. 4B is a schematic diagram illustrating a side view of a portion of the annuloplasty ring shown in FIG. 4A.

3A and 3B with a deployed curved anchor 104 according to one embodiment. FIG. 4B is a schematic diagram illustrating a side view of a portion of the annuloplasty ring shown in FIG. 4A. As shown in FIGS. 4A and 4B, the outer tube 310 may be cut to define segments (such as the plurality of segments 102 shown in FIG. 1). The outer tube 310 also includes the windows 312 (one window shown in FIG. 4A) described above and schematically represented in FIGS. 3A and 3B. As shown in FIG. 4B, in certain embodiments, the deployed anchors 104 form an angle α (e.g., about 45 degrees) with a plane 410 of the ring 300 to provide the anchors 104 with improved access to the valve annulus when the ring is positioned against the valve annulus. During anchor deployment, the plane 410 of the ring 300 is substantially parallel to the plane of the valve annulus.

Figure 5:
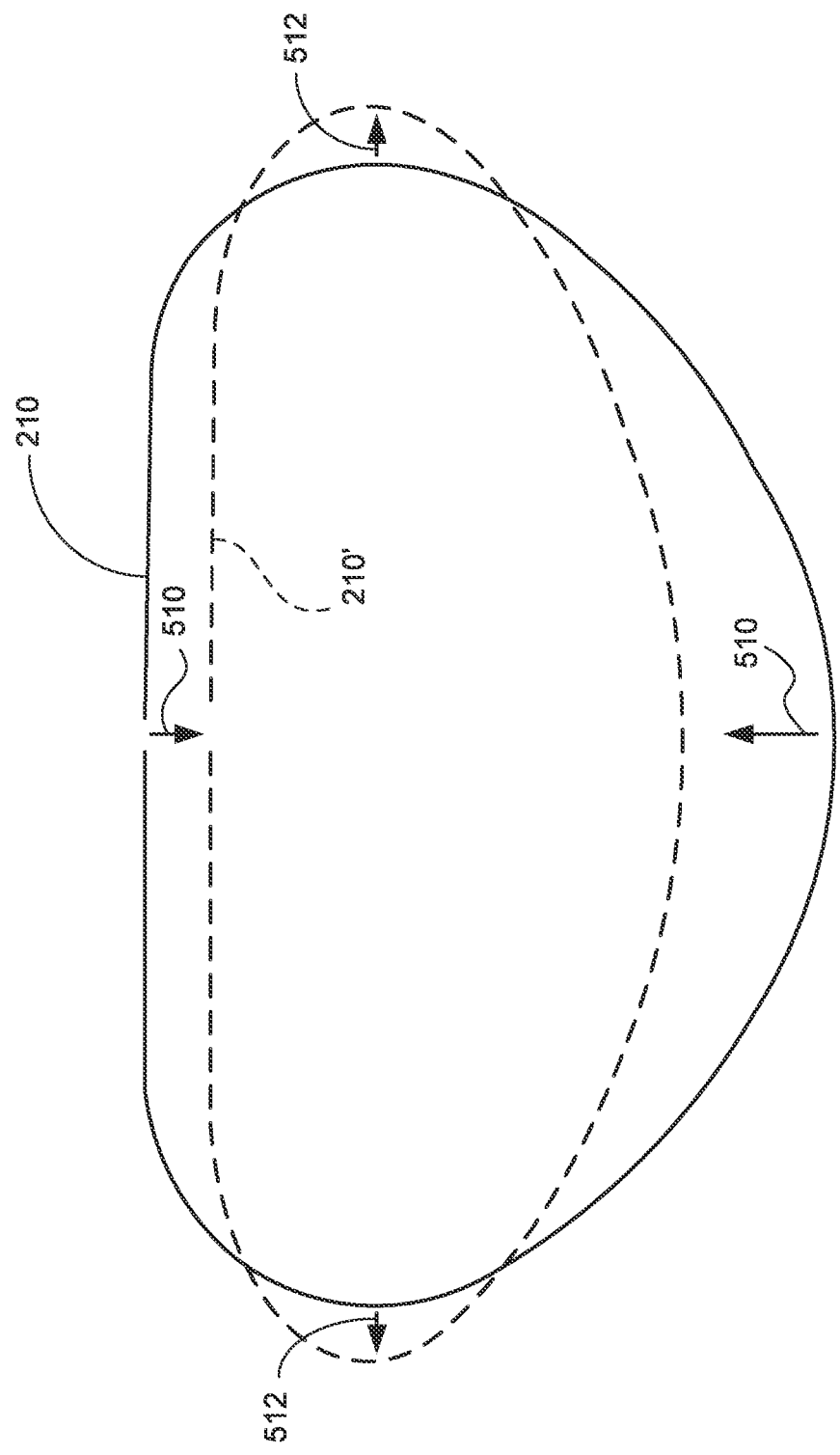
FIG. 5 is a simplified schematic diagram illustrating a side view of the internal glide ribbon shown in FIG. 2A used as a selectively adjustable member according to one embodiment.

FIG. 5 is a simplified schematic diagram illustrating a side view of the internal glide ribbon 210 shown in FIG. 2A used as a selectively adjustable member according to one embodiment. As discussed above, certain ring embodiments include a selectively adjustable member for changing the size and/or shape of the annuloplasty ring 100 (shown in FIG. 1) postoperatively to compensate for changes in the size of the heart and/or the treated heart valve. Thus, FIG. 5 illustrates the internal glide ribbon 210 in the D-shaped geometry used immediately after implanting the ring, as well as an "activated" geometry or shape 210' (shown as dashed lines) that further reduces the size of the mitral valve annulus in the (A-P) direction (as indicated by arrows 510). Such A-P contraction improves the coaptation of the leaflets such that a gap between the leaflets sufficiently closes during left ventricular contraction. In certain embodiments, the activated shape 210' also expands in the direction of arrows 512 (the C-C direction) to pull leaflet commissures away from each other, which draws the leaflets closer together and further improves their coaptation. However, in certain other embodiments, the ring 100 does not expand in the direction of the arrows 512.

As used herein, "postoperatively" refers to a time after implanting an annuloplasty ring, such as the segmented annuloplasty ring 100 shown in FIG. 1 or other rings described in other embodiments, and closing the body opening through which the ring 100 was introduced into the patient's body. For example, the ring 100 may be implanted in a child whose heart grows as the child gets older. Thus, the size of the ring 100 may need to be increased. As another example, the size of an enlarged heart may start to return to its normal size after the ring 100 is implanted. Thus, the size of the ring 100 may need to be decreased postoperatively to continue to reinforce the heart valve annulus.

Thus, in certain embodiments, the ring 100 includes a selectively adjustable member (e.g., the internal glide ribbon 210 shown in FIGS. 2A and 5) with a shape memory material (e.g., NiTi Alloy-B) that is responsive to changes in temperature and/or exposure to a magnetic field. The ring 100 is adjusted in vivo by applying an energy source to activate the selectively adjustable member and cause it to change to a memorized shape. The energy source may include, for example, radio frequency (RF) energy, x-ray energy, microwave energy, ultrasonic energy such as focused ultrasound, high intensity focused ultrasound (HIFU) energy, light energy, electric field energy, magnetic field energy, combinations of the foregoing, or the like. For example, one embodiment of electromagnetic radiation that is useful is infrared energy having a wavelength in a range between approximately 750 nanometers and approximately 1600 nanometers. This type of infrared radiation may be produced efficiently by a solid state diode laser. In certain embodiments, the implanted ring 100 is selectively heated using short pulses of energy having an on and off period between each cycle. The energy pulses provide segmental heating that allows segmental adjustment of portions of the annuloplasty ring without adjusting the entire implant.

In certain embodiments, the ring 100 includes an energy absorbing material to increase heating efficiency and localize heating in the area of the selectively adjustable member. Thus, damage to the surrounding tissue is reduced or minimized. Energy absorbing materials for light or laser activation energy may include nanoshells, nanospheres and the like, particularly where infrared laser energy is used to energize the material. Such nanoparticles may be made from a dielectric, such as silica, coated with an ultra thin layer of a conductor, such as gold, and be selectively tuned to absorb a particular frequency of electromagnetic radiation. In certain such embodiments, the nanoparticles range in size between about 5 nanometers and about 20 nanometers and can be suspended in a suitable material or solution, such as saline solution. Coatings comprising nanotubes or nanoparticles can also be used to absorb energy from, for example, HIFU, MRI, inductive heating, or the like.

In other embodiments, thin film deposition or other coating techniques such as sputtering, reactive sputtering, metal ion implantation, physical vapor deposition, and chemical deposition can be used to cover portions or all of the selectively adjustable member. Such coatings can be either solid or microporous. When HIFU energy is used, for example, a microporous structure traps and directs the HIFU energy toward the shape memory material. The coating improves thermal conduction and heat removal. In certain embodiments, the coating also enhances radio-opacity of the annuloplasty ring implant. Coating materials can be selected from various groups of biocompatible organic or non-organic, metallic or non-metallic materials such as Titanium Nitride (TiN), Iridium Oxide (Irox), Carbon, Platinum black, Titanium Carbide (TiC) and other materials used for pacemaker electrodes or implantable pacemaker leads. Other materials discussed herein or known in the art can also be used to absorb energy.

In addition, or in other embodiments, fine conductive wires such as platinum coated copper, titanium, tantalum, stainless steel, gold, or the like, are wrapped around the selectively adjustable member (see, e.g., FIG. 10) to allow focused and rapid heating of the selectively adjustable member while reducing undesired heating of surrounding ring 100 and/or tissues. In certain such embodiments, the electrically conductive wires are electrically insulated from other components of the ring 100, such as the shape memory material used in the plurality of segments 102 and/or the plurality of anchors 104.

The energy source for activating the shape memory material of the selectively adjustable member may be surgically applied after the ring 100 has been implanted by percutaneously inserting a catheter into the patient's body and applying the energy through the catheter. For example, RF energy, light energy, or thermal energy (e.g., from a heating element using resistance heating) can be transferred to the selectively adjustable member through a catheter positioned on or near the selectively adjustable member. Alternatively, thermal energy can be provided to the shape memory material by injecting a heated fluid through a catheter or circulating the heated fluid in a balloon through the catheter placed in close proximity to the selectively adjustable member. As another example, the shape memory material in the selectively adjustable member can be coated with a photodynamic absorbing material that is activated to heat the selectively adjustable member when illuminated by light from a laser diode or directed to the coating through fiber optic elements in a catheter. In certain such embodiments, the photodynamic absorbing material includes one or more drugs that are released when illuminated by the laser light. In certain embodiments, a subcutaneous electrode or coil couples energy from a dedicated activation unit. In certain such embodiments, the subcutaneous electrode provides telemetry and power transmission between the system and the annuloplasty ring. The subcutaneous electrode allows more efficient coupling of energy to the implant with minimum or reduced power loss. In certain embodiments, the subcutaneous energy is delivered to the selectively adjustable member via inductive coupling.

In other embodiments, the energy source is applied in a non-invasive manner from outside the patient's body. In certain such embodiments, the external energy source is focused to provide directional heating to the shape memory material of the selectively adjustable member so as to reduce or minimize damage to the surrounding tissue. For example, in certain embodiments, a handheld or portable device including an electrically conductive coil generates an electromagnetic field that non-invasively penetrates the patient's body and induces a current in the selectively adjustable member. The current heats the selectively adjustable member and causes the shape memory material therein to transform to a memorized shape. In certain such embodiments, the selectively adjustable member also includes an electrically conductive coil wrapped around or embedded in the memory shape material. The externally generated electromagnetic field induces a current in the selectively adjustable member's coil, causing it to heat and transfer thermal energy to the shape memory material therein.

Figure 5A:
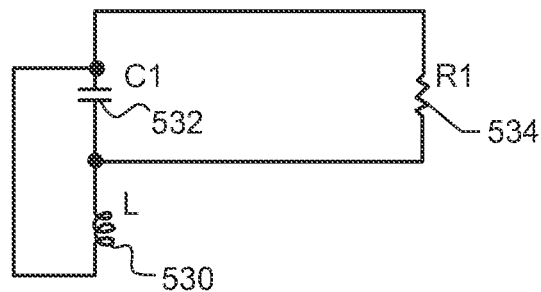
FIGS. 5A, 5B, and 5C are schematic diagrams of circuitry for using RF induction to activate the shape memory material of the internal glide ribbon according to one embodiment.
Figure 5B:
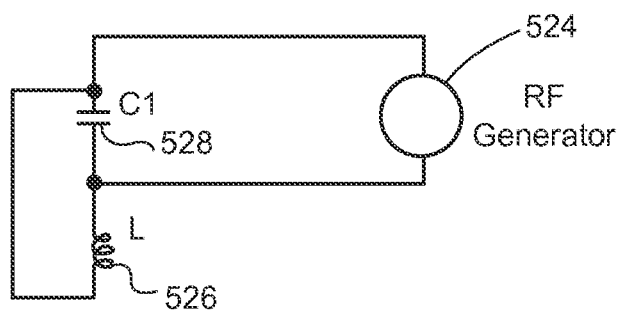
Figure 5C:
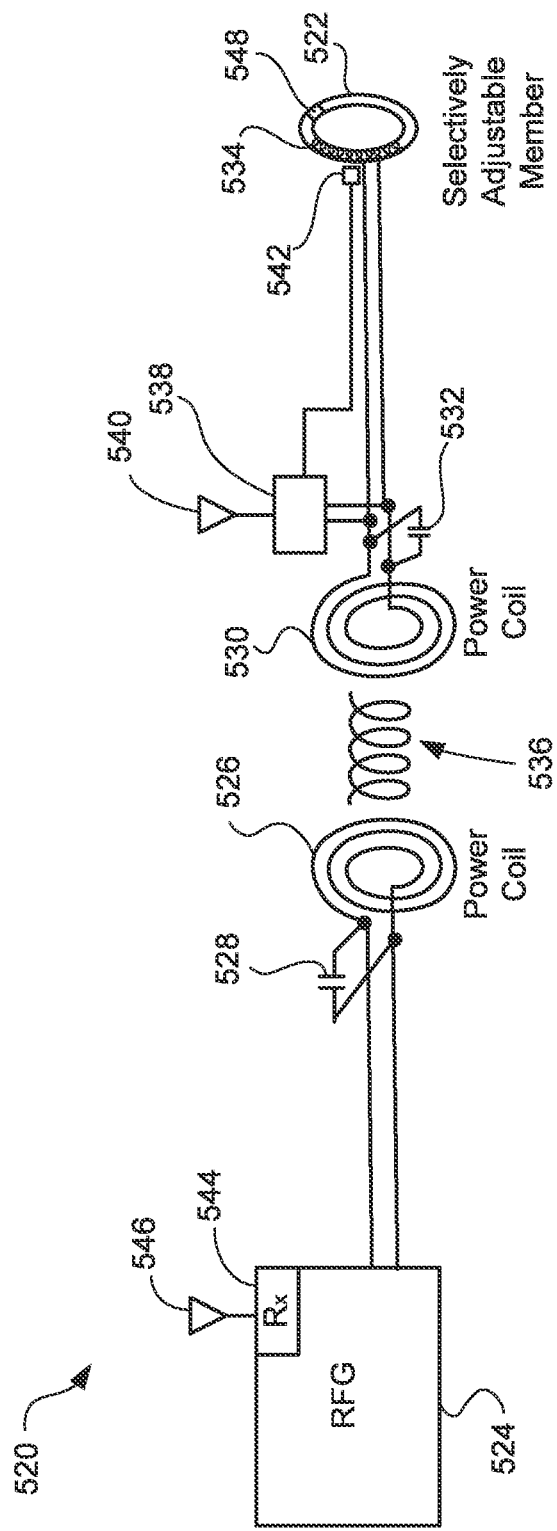

By way of example, FIGS. 5A, 5B, and 5C are schematic diagrams of circuitry for using RF induction to activate the shape memory material of the internal glide ribbon 210 according to one embodiment. FIG. 5A illustrates circuitry located in a selectively adjustable annuloplasty ring and FIG. 5B illustrates circuitry of an external (i.e., external to the patient) RF induction activation system according to one embodiment. FIG. 5C is a block diagram of a system 520 for inductively activating a selectively adjustable member 522 (e.g., the internal glide ribbon 210) of a ring according to certain embodiments.

Referring to FIGS. 5A, 5B, and 5C, the RF induction activation system 520 includes a power source 524 (also referred to herein as an RF generator or RFG) capable of creating an alternating electrical signal of suitable power. The power source 524 is connected to a delivery coil 526 tuned to resonate at the same frequency as the output of the power source 524. A capacitor 528 is used to tune the delivery coil 526 to resonate at the desired frequency. The implantable dynamically adjustable annuloplasty ring assembly includes a second (receiving) coil 530 positioned within the patient that is designed to resonate at substantially the same frequency as that of the delivery coil 526 connected to the power source 524. A capacitor 532 is used to tune the receiving coil 530 to resonate at the desired frequency. The receiving coil 530 is connected to a heating element 534 (represented by a resistance R1 in FIG. 5A) wrapped around the selectively adjustable member 522 (as shown in FIG. 5C). To activate the annuloplasty ring, the delivery coil 526 is placed near the receiving coil 530 of the selectively adjustable member 522 (e.g., near the patient's chest) and switched on. Power from the resonating magnetic field 536 (shown in FIG. 5C) is then inductively transferred across the skin barrier to the receiving coil 530 and converted to electrical current that is subsequently used to heat the selectively adjustable member 522. In an example embodiment, the inductance frequency is above about 100 kHz so that any leakage current that may come in contact with the patient would not cause uncomfortable sensations during activation.

In certain embodiments, embedded computing and/or remote temperature sensing is used. For example, FIG. 5C shows that additional circuitry 538 may be implanted in the patient. The additional circuitry 538 may include transmitter circuitry (including an antenna 540), a microprocessor, power circuitry, and temperature measuring circuitry (e.g., one or more thermocouple (TC) devices 542, coupled to the additional circuitry 538). Similarly, the RFG 524 may include receiver circuitry 544 (including an antenna 546) for receiving temperature and other data from the additional circuitry 538 implanted in the patient. Although not shown, the RFG 524 may also include a processor for processing and displaying the information received from the additional circuitry 538 implanted within the patient.

The information received from the additional circuitry 538 may include, for example, the power induced in the selectively adjustable member 522. In one embodiment, the power transferred to the selectively adjustable member 522 is measured by reading the voltage across the selectively adjustable member 522 and/or heating element 534 and, because the resistance of the selectively adjustable member 522 and/or heating element 534 is known, the power can be calculated and communicated to the RFG 524 by the telemetry link. In another example, the temperature and size of the selectively adjustable member 522 may be sensed and sent by transmitter circuitry in the additional circuitry 538 to the receiving circuitry 544 via radiotelemetry. Temperature may be sensed using the thermocouple device 542, and the size of the ring may be deduced via built in strain gauges 548 (e.g., different resistance values equal a proportional change in size).

In one embodiment, the RFG 524 automatically finds a resonant point. The RFG 524 may be programmed to analyze wattage delivered during operation (e.g., as discussed above) and may adjust the output frequency to increase or maximize the greatest power transfer. This may be accomplished in certain embodiments by directly monitoring the current output on the delivery coil 526, or the peak voltage induced in the receiving coil 530 via telemetry.

In one embodiment, the system 520 is capable of multiple resonant frequencies. For example, the heating element 534 (coupled to the selectively adjustable member 522) may be electrically connected to more than one coil—each coil having a different natural resonance. In another embodiment, different coils may be attached to different heating elements or devices in the ring that can be operated separately. The transmitting power source 524 may have a set of coils (e.g., including the delivery coil 526) that can be selectively used to couple to its respective sister coil (e.g., including the receiving coil 530) coupled to the selectively adjustable member 522.

By using this wireless technique of power transmission, the patient may be electrically isolated from the system 520 during activation of an implanted device. Thus, the possibility of electrocution due to a ground fault is eliminated or reduced.

In some embodiments, centering of coils is used. Such embodiments use techniques of aligning the coils, such as through the use of physical landmarks molded into a housing of the implanted receiving coil, magnets, and/or infrared lighting. For example, an infrared light emitting diode (LED) may be installed on the implanted receiving coil 530 and may light during activation. An infrared detector located on the delivery coil 526 may be configured to give a user feedback on how much light it receives. A set of magnets may also be strategically placed in the delivery coil 526 and receiving coil 530. As the magnets are brought close together, the magnetic attraction may be utilized to align the coils 526, 530.

Example Ring Embodiments with Linear Anchors

Figure 6A:
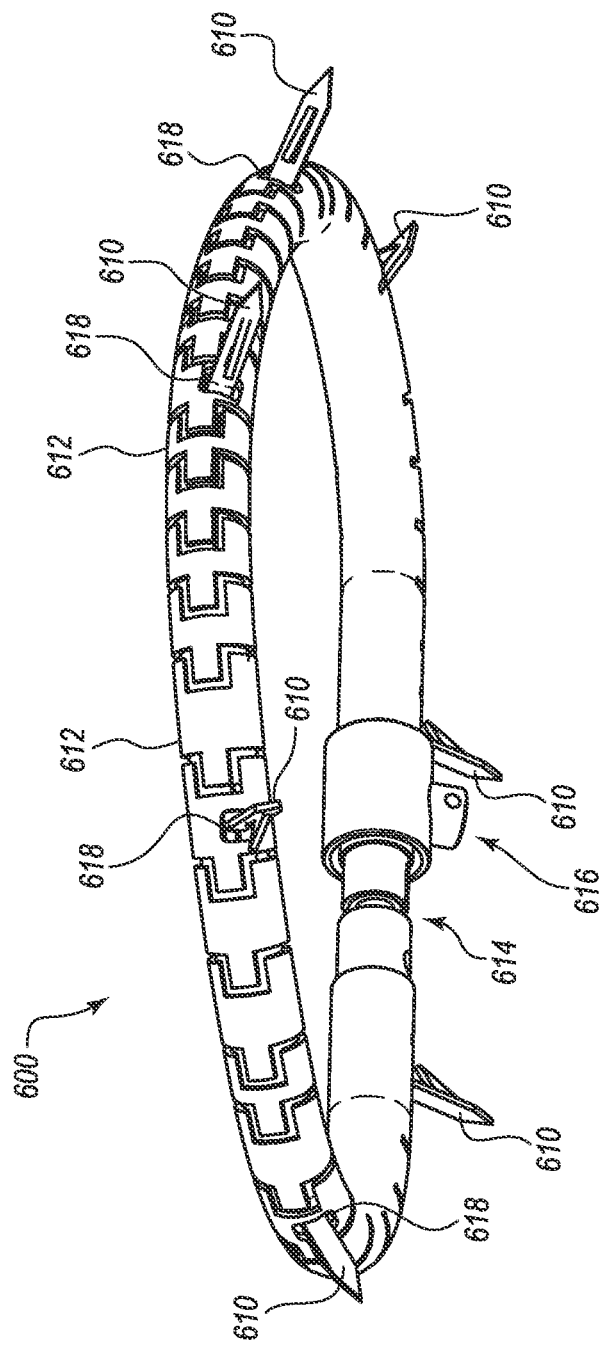
FIG. 6A is a schematic diagram illustrating a perspective view of a segmented annuloplasty ring including a plurality of linear anchors according to one embodiment.

FIG. 6A is a schematic diagram illustrating a perspective view of a segmented annuloplasty ring 600 including a plurality of linear anchors 610 according to one embodiment. Seven linear anchors 610 are shown. However, artisans will understand from the disclosure herein that more linear anchors 610 or fewer linear anchors may be used. For example, certain embodiments may use ten or more linear anchors 610.

The segmented annuloplasty ring 600 includes a plurality of segments 612 at least partially cut into a shape memory hypotube that forms a "D-shape" in the annular operable geometry (e.g., when implanted around the annulus) and may be straightened into an elongate insertion geometry for implanting the ring 600 within a patient's heart through a catheter. As discussed above with respect to FIG. 1, the ring 600 may also include a ring closure lock 614 (shown in a connected or locked position) for snap locking the two ends of the ring together, and a pivot 616. In the example embodiment shown in FIG. 6A, the ring closure lock 614 is connected directly to the pivot 616 along the straight portion of the D-shaped ring.

As discussed above with respect to other embodiments, the ring 600 includes a plurality of anchor deployment windows 618 cut into the shape memory hypotube. The plurality of linear anchors 610 may be selectively deployed through the windows 618 in a manner similar to that described above for curved anchors 104.

Figure 6B:
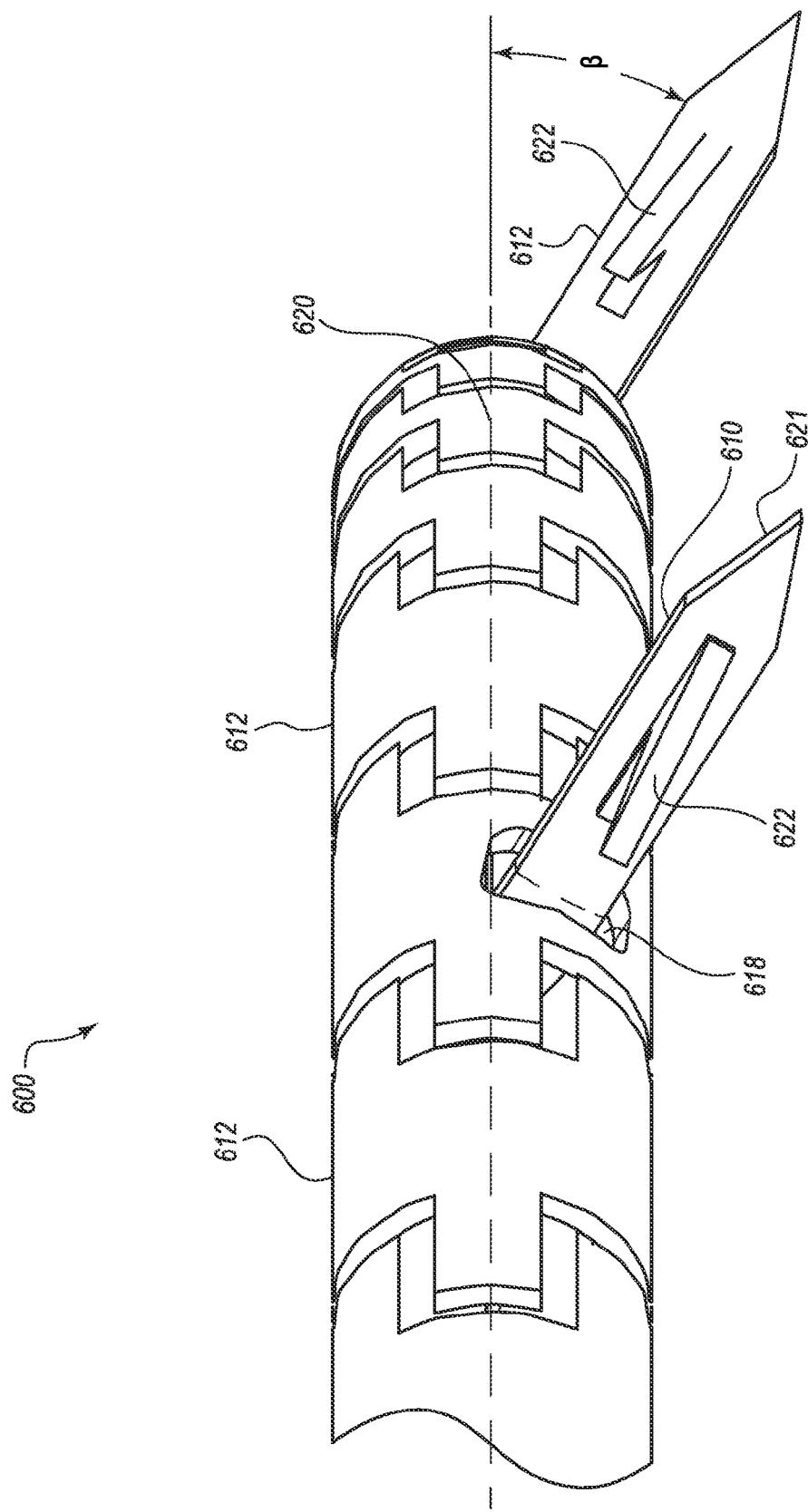
FIG. 6B is a schematic diagram illustrating a side view of a portion of the annuloplasty ring shown in FIG. 6A.

FIG. 6B is a schematic diagram illustrating a side view of a portion of the annuloplasty ring shown in FIG. 6A. As shown in FIG. 6B, in certain embodiments, the deployed linear anchors 610 form an angle β (e.g., about 45 degrees) with a plane 620 of the ring 600 to provide the linear anchors 610 with improved access to the valve annulus when the ring is positioned against the valve annulus. During anchor deployment, the plane 620 of the ring 600 is substantially parallel to the plane of the valve annulus. As shown in FIG. 6B, the linear anchors 610 may include a pointed prong 621 for penetrating tissue and a barb 622 that secures the anchor to the tissue.

Figure 7:
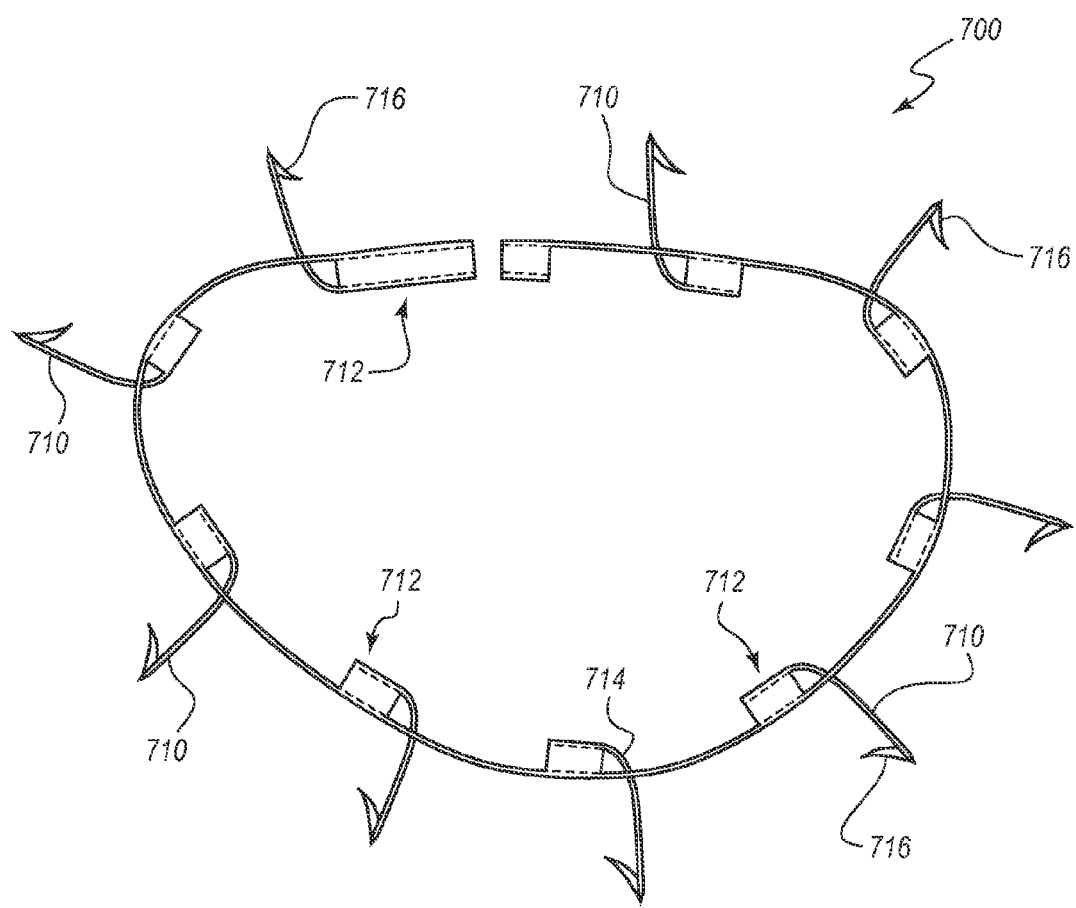
FIG. 7 is a simplified schematic diagram illustrating a side view of an internal anchor member including linear anchors according to one embodiment.

FIG. 7 is a simplified schematic diagram illustrating a side view of an internal anchor member 700 including linear anchors 710 according to one embodiment. The linear anchors 710 may be affixed (e.g., laser welded) to the internal anchor member 700. In the embodiment shown in FIG. 7, however, the internal anchor member 700 and linear anchors 710 are cut from a single superelastic shape memory (e.g., Nitinol) hypotube. FIG. 7, for example, shows remaining tubular portions 712 after the hypotube is cut to form prongs 714 of the linear anchors 710. The remaining tubular portions 712 facilitate sliding (e.g., using wires or sutures accessible through the catheter) the internal anchor member 700 coaxially within the hollow tube of the ring (e.g., within the segmented annuloplasty ring 600 shown in FIG. 6).

The internal anchor member 700 is heat set to the same memorized annular shape as the ring. The anchors prongs 714 can be heat set to protrude outward through windows cut in the segmented annuloplasty ring 600. Barbs 716 may be laser welded to the prongs 714 to form the linear anchors 710. The linear anchors 710 are retracted/deployed by sliding the internal anchor member 700 within the segmented annuloplasty ring 600.

Figure 8A:
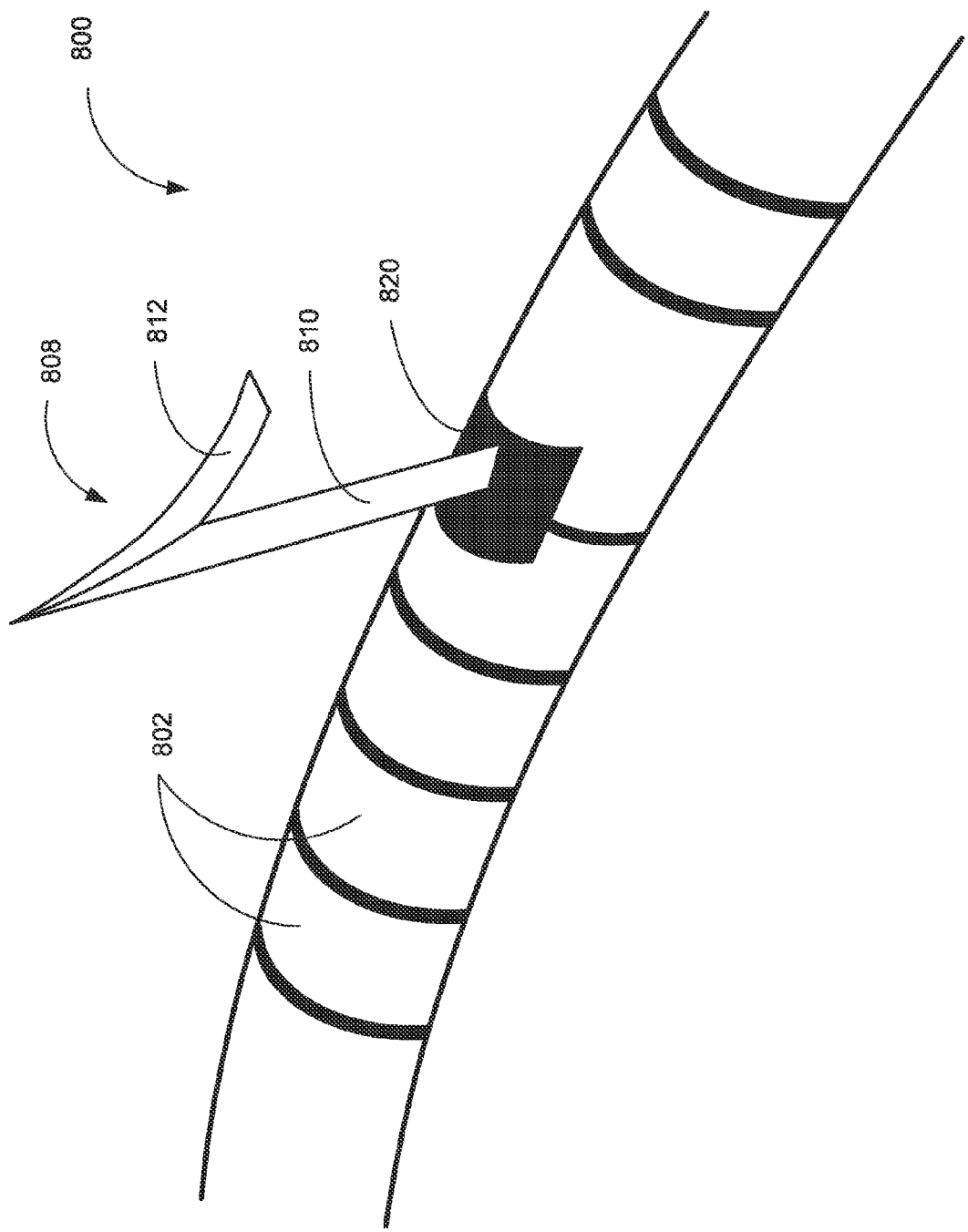
FIG. 8A is a schematic diagram illustrating an enlarged perspective view of a single-barbed anchor of a percutaneous transcatheter annuloplasty ring in an affixation configuration according to one embodiment.

FIG. 8A is a schematic diagram illustrating an enlarged perspective view of a single-barbed anchor 808 of a percutaneous transcatheter annuloplasty ring 800 in an affixation configuration according to one embodiment. The anchor 808 includes a prong 810 and a single barb 812 welded to the prong 810. The prong 810 is integrated with or connected to an inner tube member (not shown, but see FIG. 7) and protrudes through a window 820 cut in an outer tube member formed by a plurality of segments 802.

Figure 8B:
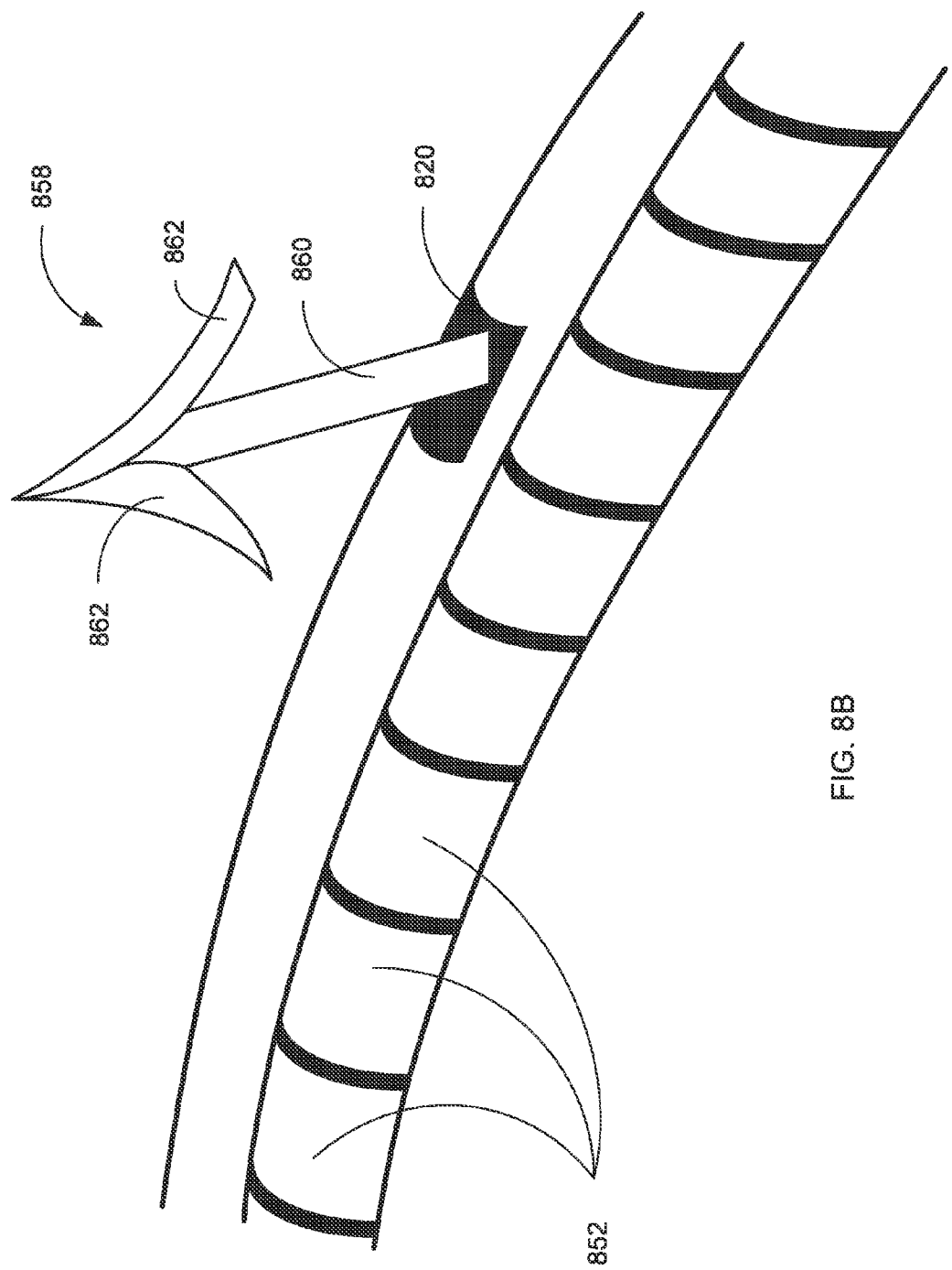
FIG. 8B is a schematic diagram of an enlarged perspective view of a dual-barbed anchor of a percutaneous transcatheter annuloplasty ring in an affixation configuration according to one embodiment.

FIG. 8B is a schematic diagram of an enlarged perspective view of a dual-barbed anchor 858 of a percutaneous transcatheter annuloplasty ring in an affixation configuration according to one embodiment. The anchor 858 includes a prong 860 and two barbs 862 welded to the prong 860. The prong 860 is integrated with or connected to an inner tube member (not shown) and protrudes through a window 820 cut in an outer tube member formed by a plurality of segments 852.

Figure 9:
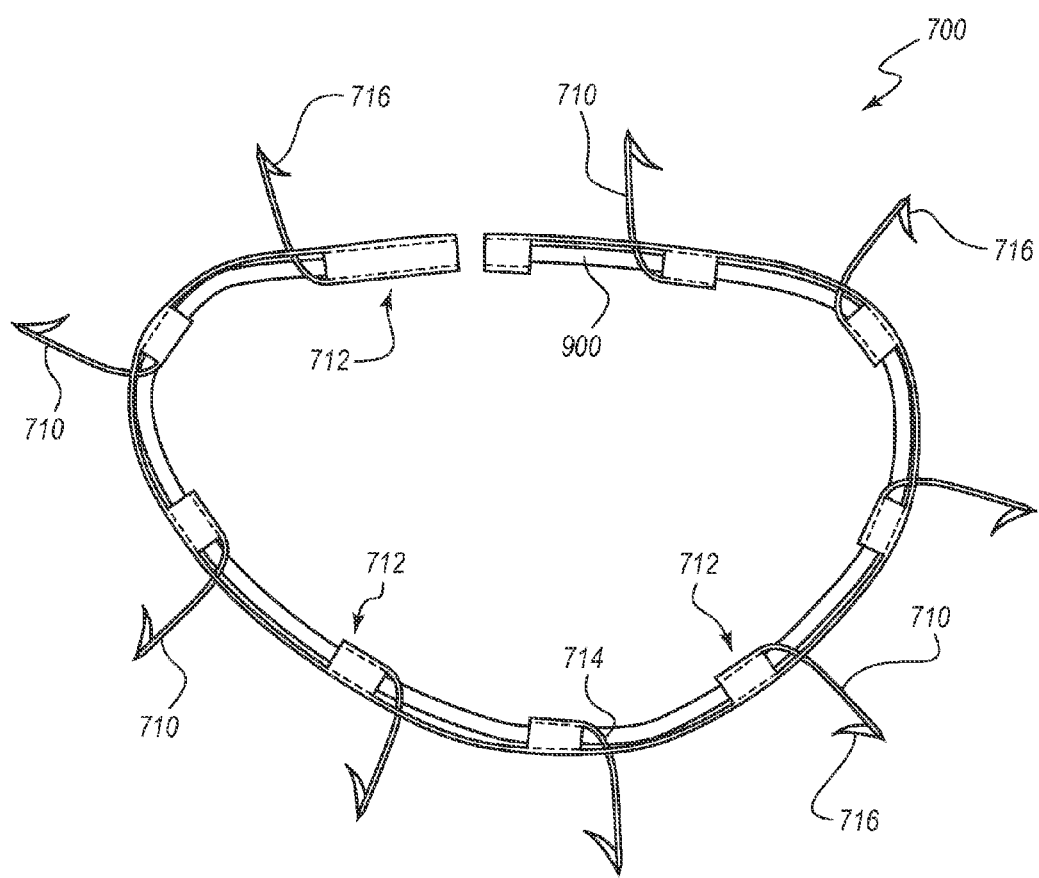
FIG. 9 is a simplified schematic diagram illustrating a side view of the internal anchor member shown in FIG. 7 and a selectively adjustable member according to one embodiment.

FIG. 9 is a simplified schematic diagram illustrating a side view of the internal anchor member 700 shown in FIG. 7 and a selectively adjustable member 900 according to one embodiment. As discussed above, the selectively adjustable member 900 is configured to change the size and/or shape of the annuloplasty ring 600 postoperatively to compensate for changes in the size of the heart and/or the treated heart valve. In FIG. 9, the selectively adjustable member 900 is shown passing through the remaining tubular portions 712 of the cut hypotube of the internal anchor member 700. In such embodiments, the selectively adjustable member 900 may be rod shaped and may have an outer diameter of about 40 microns. In other embodiments, the selectively adjustable member 900 may be located adjacent to the internal anchor member 700 (e.g., around the external circumference, the internal circumference, or lateral to the internal anchor member 700).

The selectively adjustable member 900 includes a shape memory material (e.g., NiTi Alloy-B) that is responsive to changes in temperature and/or exposure to a magnetic field. The selectively adjustable member 900 may be activated, for example, using any of the energy sources or methods described above with respect to FIGS. 5, 5A, 5B, and 5C. The activated geometry of the selectively adjustable member 900, according to certain embodiments, reduces the size of the mitral valve annulus in the AP direction.

Figure 10:
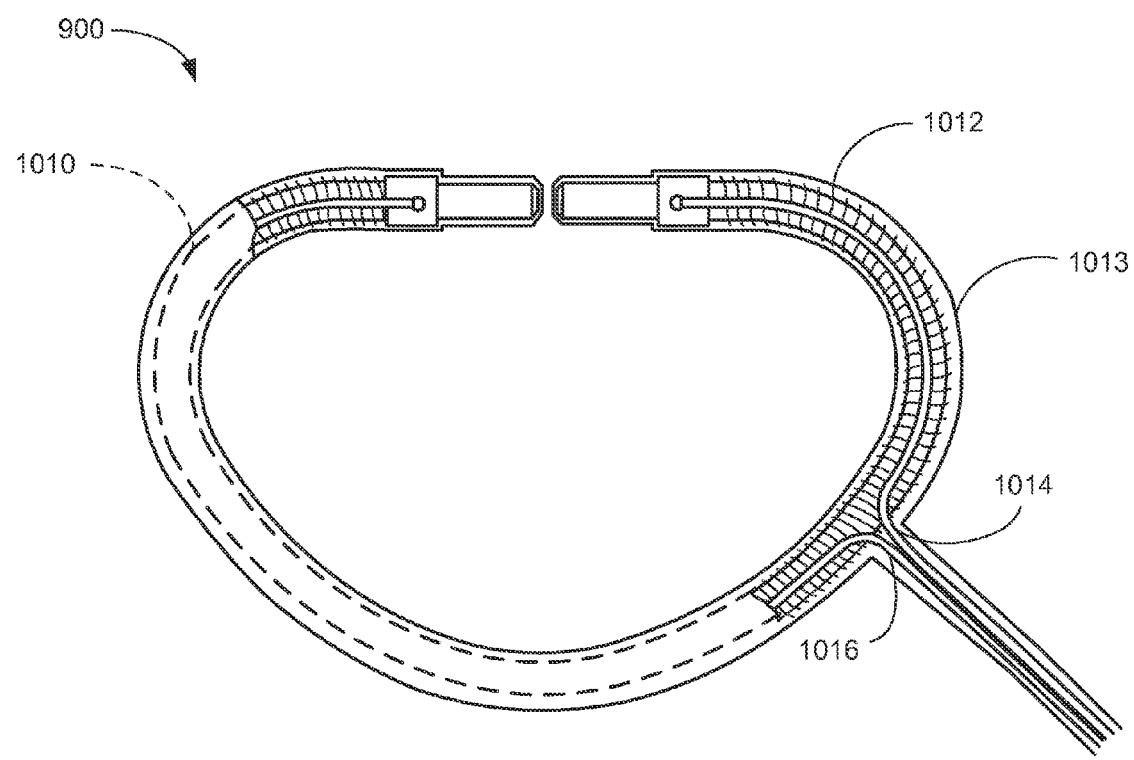
FIG. 10 is a schematic diagram illustrating a partial cross-sectional view of the selectively adjustable member shown in FIG. 9 according to one embodiment.

FIG. 10 is a schematic diagram illustrating a partial cross-sectional view of the selectively adjustable member 900 shown in FIG. 9 according to one embodiment. The selectively adjustable member 900 in this example includes a shape memory rod 1010, a heating element 1012 (e.g., electrically conductive wire) coiled around the shape memory rod 1010, and an electrically insulating cover 1013 surrounding the shape memory rod 1010 and heating element 1012. The electrically insulating cover 1013 prevents current passing through the heating element 1012 from flowing to nearby metals or other shape memory alloys in the ring (e.g., the outer segmented annuloplasty ring 600 and/or the internal anchor member 700), or to surrounding tissue. The electrically insulating cover 1013 may also provide thermal insulation to protect the surrounding tissue from excessive heat.

As shown in FIG. 10, the selectively adjustable member 900 may include leads 1014, 1016 for providing induced current through the heating element 1012. The leads 1014, 1016 may exit through the septal wall, the right atrium subclavian vein, or both leads may follow the ring contour and exit at $P_1/P_2$ leaflet junction or $P_3/P_2$ leaflet junction.

In certain embodiments, the receiving coil 530 (shown in FIGS. 5A and 5C) and any associated internal circuitry may be placed anywhere within the patient and outside the heart of the patient. For example, the receiving coil 530 and/or additional circuitry 538 may be implanted immediately below the surface of the skin and coupled to the heating element 1012

(coupled to the selectively adjustable member 900) via one or more wires extending into the heart. In another embodiment, the receiving coil 530 and associated internal circuitry may be integrated with the annuloplasty ring and/or the selectively adjustable member 900. For example, the receiving coil 530 and additional circuitry 538 may be incorporated internal to the annuloplasty ring. In still another embodiment, the receiving coil 530 may be implanted adjacent the lead wire and/or the receiving coil, in close proximity to the selectively adjustable member 900.

Example Deployment Embodiments

Figure 11A:
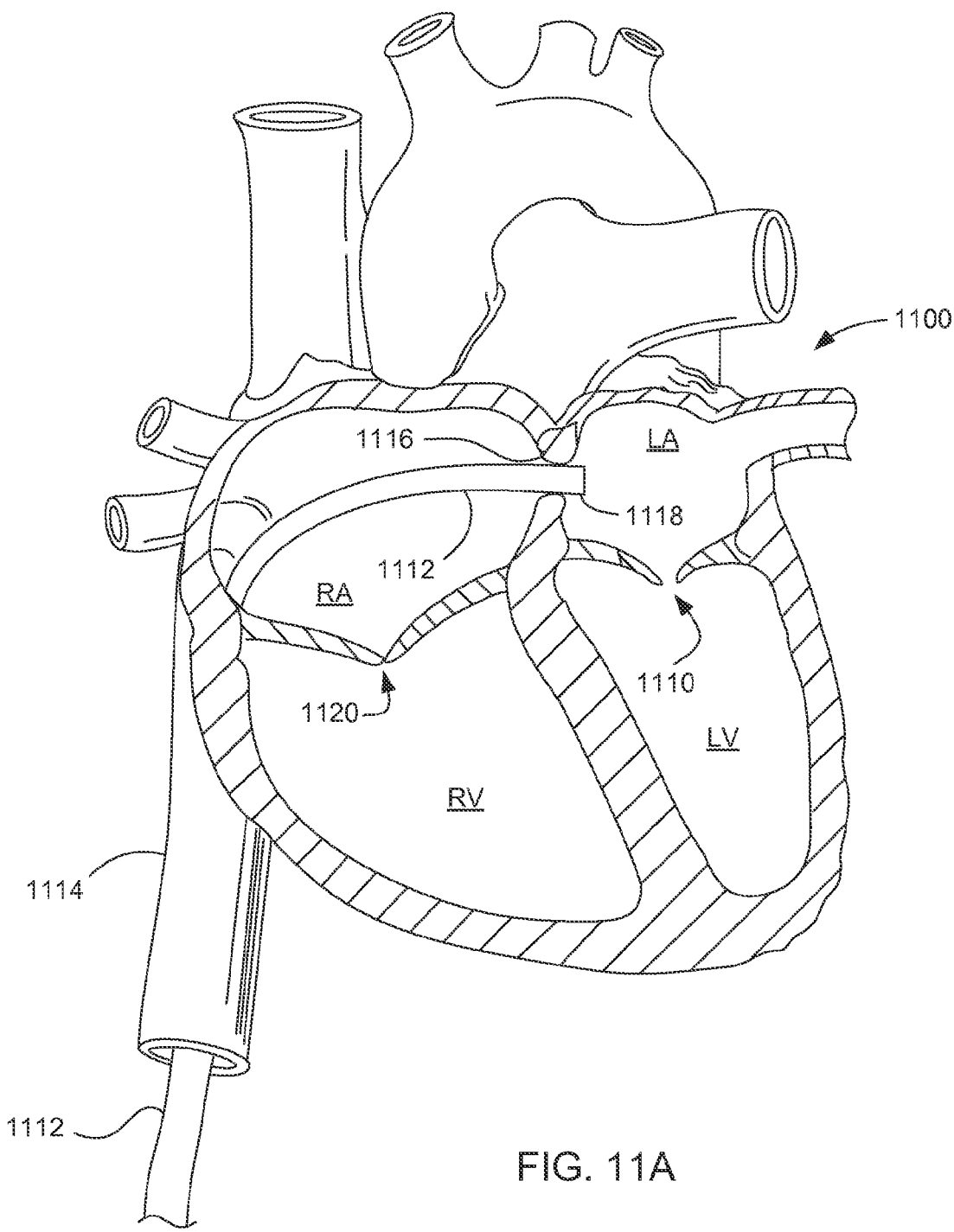
FIG. 11A is a schematic diagram illustrating a trans-septal approach for endovascular delivery of an annuloplasty ring to the mitral valve of a heart according to one embodiment.

As discussed above, the annuloplasty ring embodiments disclosed herein are configured for percutaneous transcatheter delivery and fixation to heart valves. The rings may be delivered through a catheter to the mitral valve, for example, using a trans-septal approach, a retrograde approach, or a trans-apical approach. For example, FIG. 11A is a schematic diagram illustrating a trans-septal approach for endovascular delivery of an annuloplasty ring (not shown) to the mitral valve 1110 of a heart 1100 according to one embodiment. For illustrative purposes, a partial cross-section of the heart 1100 is illustrated to show the right atrium RA, right ventricle RV, left atrium LA, and left ventricle LV. For clarity, certain features (e.g., papillary muscles and chordae tendineae) are not shown. In the trans-septal approach shown in FIG. 11A, the left atrium LA is approached by advancement of a catheter 1112 through the inferior vena cava 1114, into the right atrium RA, across the interatrial septum 1116, and into the left atrium LA. The annuloplasty ring may then be delivered through the catheter 1112 into the atrium and anchored to the annulus of the mitral valve 1110.

As shown in FIG. 11A, the catheter 1112 is delivered percutaneously into the heart 1100. A guiding sheath (not shown) may be placed in the vasculature system of the patient and used to guide the catheter 1112 and its distal end 1118 to a desired deployment site. In some embodiments, a guide wire (not shown) is used to gain access through the superior or inferior vena cava 1114, for example, through groin access for delivery through the inferior vena cava 1114. The guiding sheath may be advanced over the guide wire and into the inferior vena cava 1114 shown in FIG. 11A. The catheter 1112 may be passed through the right atrium RA and towards the interatrial septum 1116. Once the distal end 1118 of the catheter 1112 is positioned proximate to the interatrial septum 1116, a needle or piercing member (not shown) is advanced through the catheter 1112 and used to puncture the fossa ovalis or other portion of the interatrial septum 1116. In some embodiments, the catheter 1112 is dimensioned and sized to pass through the fossa ovalis without requiring a puncturing device. That is, the catheter 1112 may pass through the natural anatomical structure of the fossa ovalis into the left atrium LA.

Similarly, any chamber (LV, RV, LA, RA) of the heart 1100 may be approached through the inferior vena cava 1114. For example, the right ventricle RV may be approached through the inferior vena cava 1114, into the right atrium RA, and through the tricuspid valve 1120. A variety of other endovascular approaches may also be used.

Figure 11B:
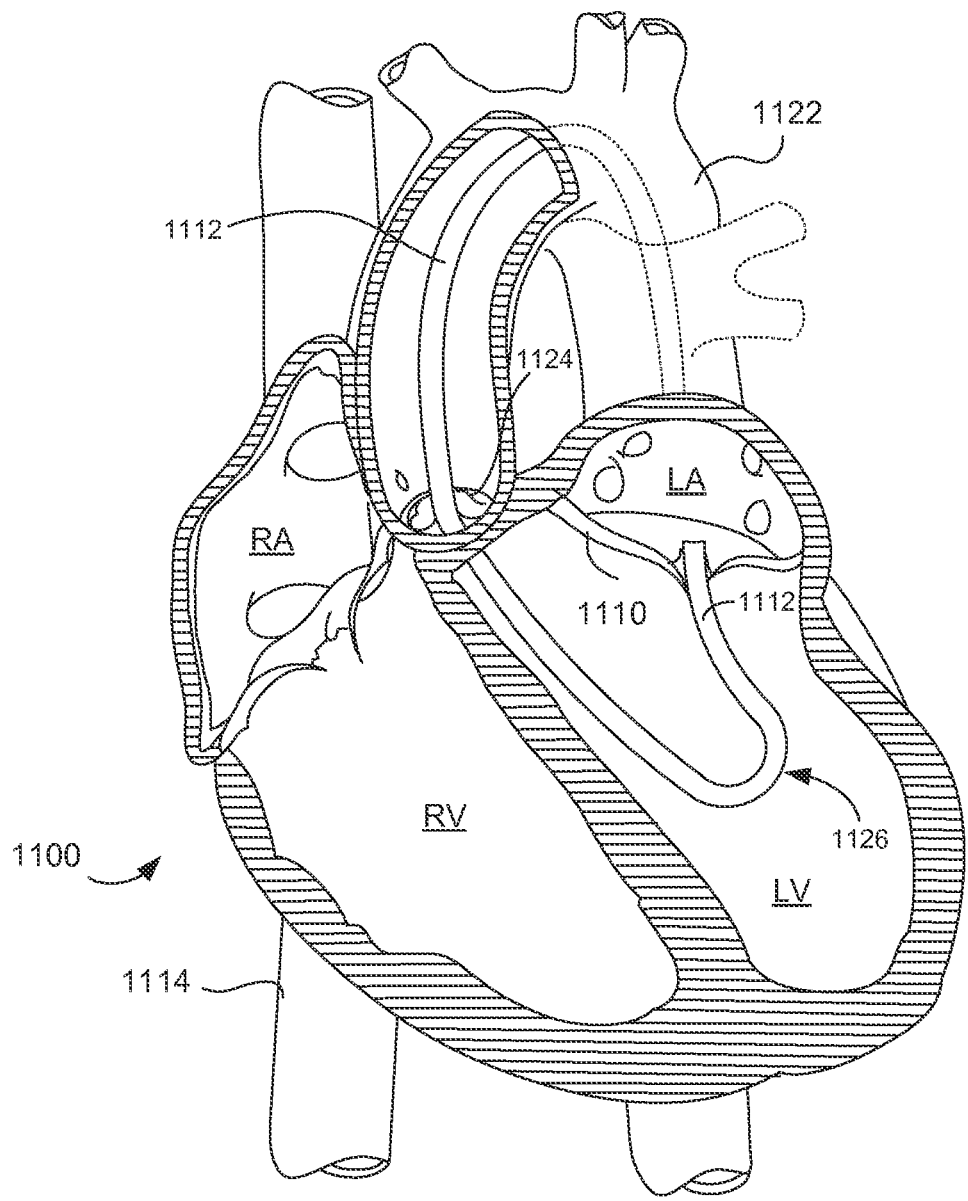
FIG. 11B is a schematic diagram illustrating an example retrograde approach of an annuloplasty ring to the mitral valve of a heart according to another embodiment.

FIG. 11B is a schematic diagram illustrating an example retrograde approach of an annuloplasty ring (not shown) to the mitral valve 1110 of a heart 1100 according to another embodiment. In FIG. 11B, a femoral approach is shown wherein the delivery catheter 1112 is advanced through the aorta 1122 and the aortic valve 1124. Typically, the catheter 1112 is advanced through a sheath positioned within the femoral artery (not shown). Under fluoroscopy or other methods of guidance, the distal end of the catheter 1112 is guided within the left ventricle LV and turned (e.g., as shown with a "U-turn" 1126) within the left ventricle LV so as to pass through the leaflets of the mitral valve 1110 and into the left atrium LA. After verification of the appropriate positioning of the catheter 1112, a guide wire (not shown) may be inserted through the catheter 1112 into the left atrium LA, which may then be used to guide one or more other catheters into the left atrium LA for delivering and anchoring the annuloplasty ring to the annulus of the mitral valve 1110.

Figure 11C:
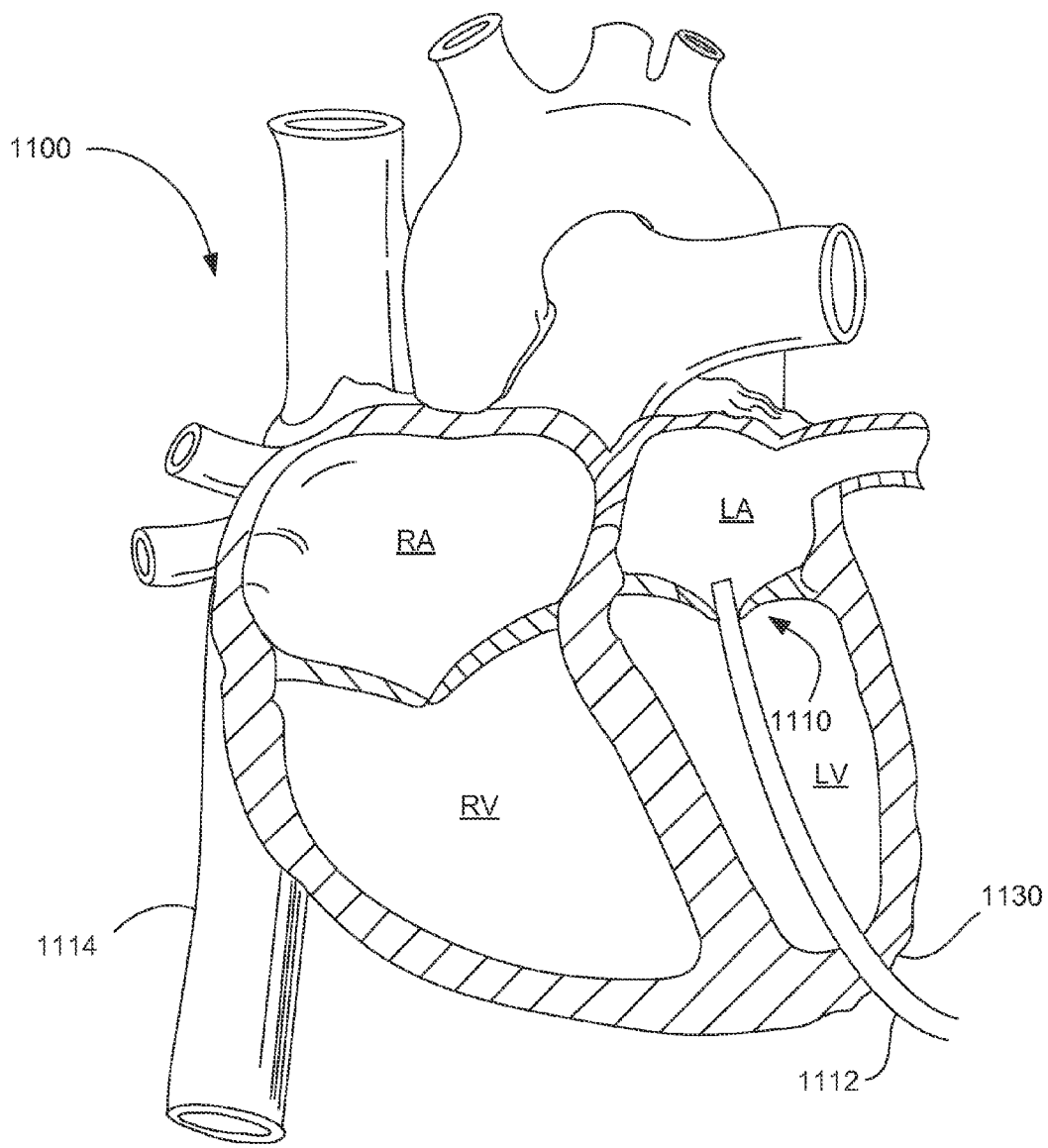
FIG. 11C is a schematic diagram illustrating an example trans-apical approach of an annuloplasty ring to the mitral valve of a heart according to another embodiment.

FIG. 11C is a schematic diagram illustrating an example trans-apical approach of an annuloplasty ring (not shown) to the mitral valve 1110 of a heart 1100 according to another embodiment. In this example, the catheter 1112 is shown passing through the apex 1130 of the heart 1100, through the left ventricle LV, through the leaflets of the mitral valve 1110, and into the left atrium. The annuloplasty ring, may be delivered through the catheter 1112 into the left atrium LA and anchored to the annulus of the mitral valve 1110. In one embodiment, a needle or trocar may be used to puncture through the apex 1130 to create a small opening through which a guide wire (not shown) can be inserted through the left ventricle LV into the left atrium LA. Then, the guide wire may be used to guide successively larger and stiffer catheters so as to gradually increase the size of the opening in the apex 1130 of the heart 1100.

Figure 12A:
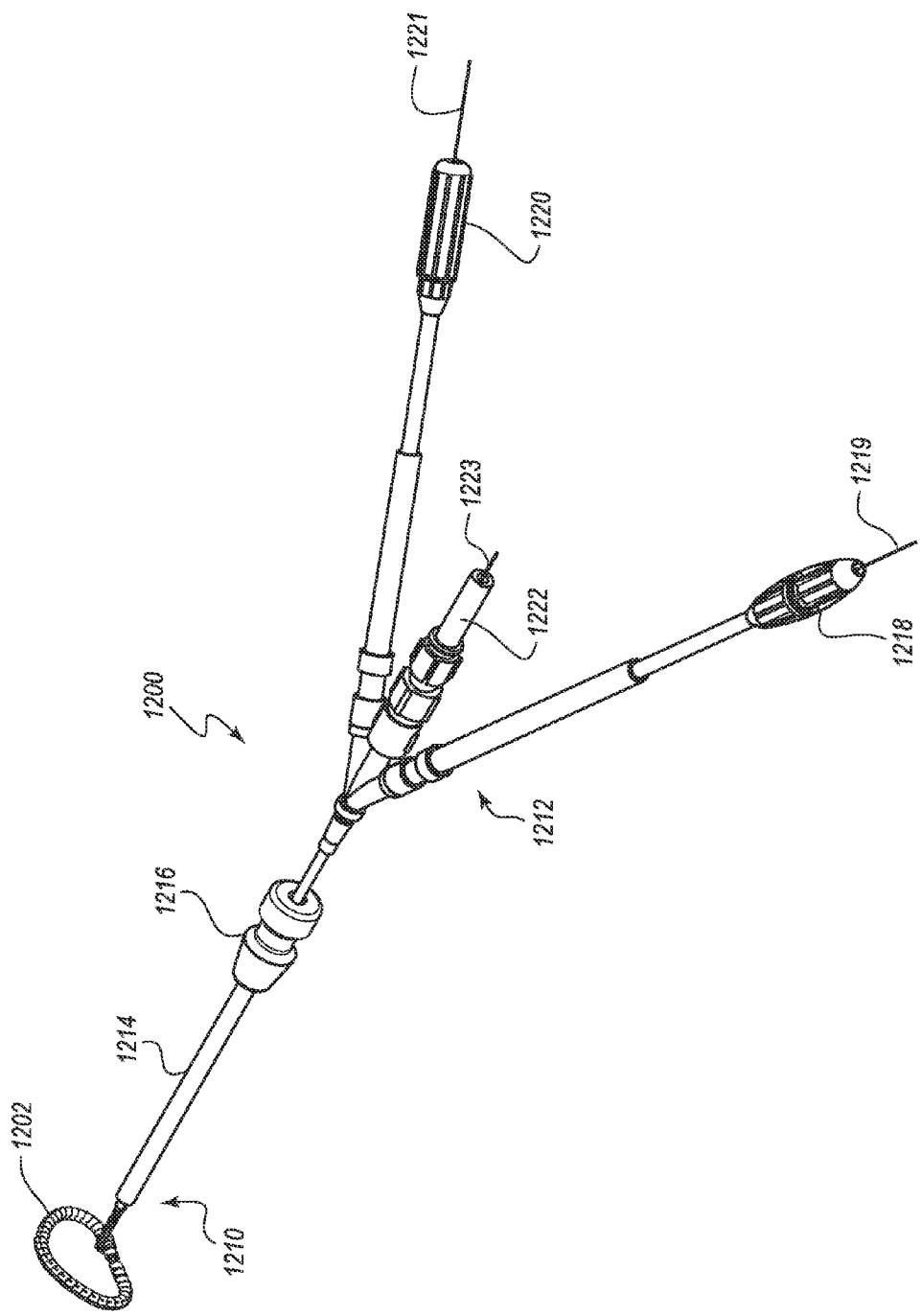
FIGS. 12A and 12B are schematic diagrams illustrating a delivery system for implanting a segmented annuloplasty ring within a heart according to certain embodiments.
Figure 12B:
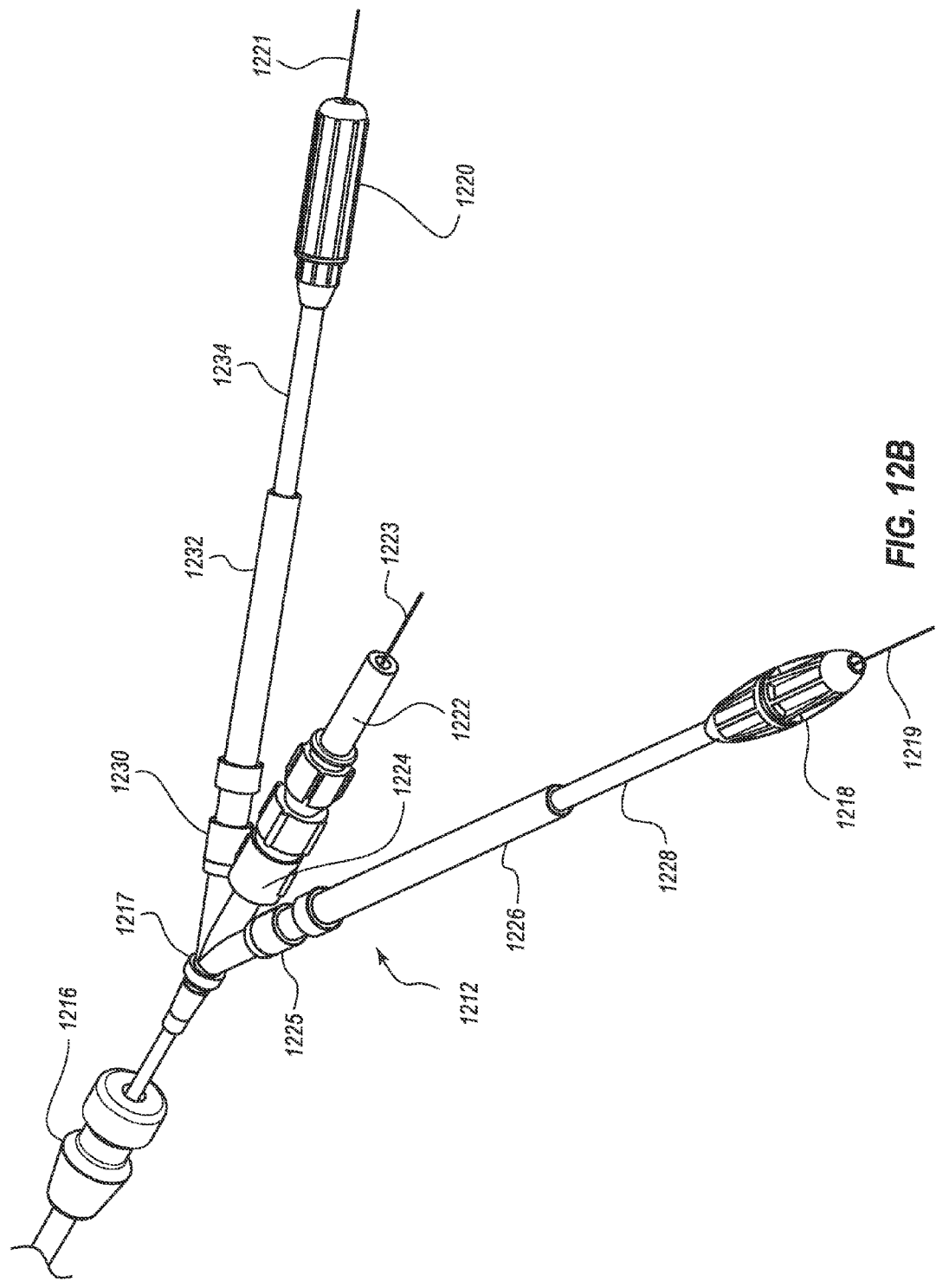

FIGS. 12A and 12B are schematic diagrams illustrating a delivery system 1200 for implanting a segmented annuloplasty ring 1202 within a heart according to certain embodiments. FIG. 12A illustrates a perspective view of the delivery system 1200, including a distal end 1210 and a proximal end 1212. FIG. 12B illustrates an enlarged view of the proximal end 1212 shown in FIG. 12A. The distal end 1210 is discussed below in more detail with respect to FIGS. 13A and 13B. The delivery system 1200 includes an outer jacket delivery catheter 1214 having a proximal end attached to a hemostatic connector 1216.

The proximal end 1212 of the system 1200 includes a first torque controller 1218 for controlling a first suture 1219 used for snapping together the ends of the ring 1202, a second torque controller 1220 for controlling a second suture 1221 for deploying anchors (not shown) from the ring 1202, and a third torque controller 1222 for controlling a ring deployment wire 1223 for orienting the ring 1202 within the heart and releasing the ring 1202 from the delivery system 1200. The first suture 1219 and/or the second suture 1221 may include a resilient material capable of providing a pulling force to elements within the ring 1202, as discussed below. Thus, the first suture 1219 and/or the second suture 1221 may include, for example, Teflon, steel, or Nitinol. In one embodiment, the ring deployment wire 1223 includes a superelastic shape memory material (e.g., Nitinol) for orienting the ring 1202, as discussed below. In some embodiments, the first suture 1219, the second suture 1221, and/or the ring deployment wire 1223 are Teflon-coated.

The first torque controller 1218, the second torque controller 1220, and the third torque controller 1222 are connected to the hemostatic connector 1216 through a four-port connector 1217. In one embodiment, the four-port connector 1217 comprises a luer port. The first torque controller 1218 is connected to the four-port connector 1217 through a spring tension luer 1225, a spring tension assembly 1226 and a spring tension plunger 1228. The spring tension assembly 1226 includes an internal spring (not shown) against which the plunger 1228 is biased to provide a desired amount of tension to the first suture 1219 under the control of the torque controller 1218, and to pull the first suture 1219 to snap-lock the ends of the ring 1202 together. Similarly, the second torque controller 1220 is connected to the four-port connector 1217 through a spring tension luer 1230, a spring tension assembly 1232 and a spring tension plunger 1234 to provide a desired amount of tension to the second suture 1221 under the control of the second torque controller 1220, and to pull the second suture 1221 to deploy the anchors. In one embodiment, the first suture 1219 and/or the second suture 1221 may include a notch (not shown) within or near the ring 1202 that is configured to break the respective suture 1219, 1221 by applying additional tension after the suture 1219, 1221 has performed its respective function (e.g., after the suture 1219 snaps the ends of the ring 1202 together or after the suture 1221 deploys the anchors). The third torque controller 1222 is connected to the four-port connector 1217 through an adapter 1224, such as a Touhy borst adapter.

Figure 13A:
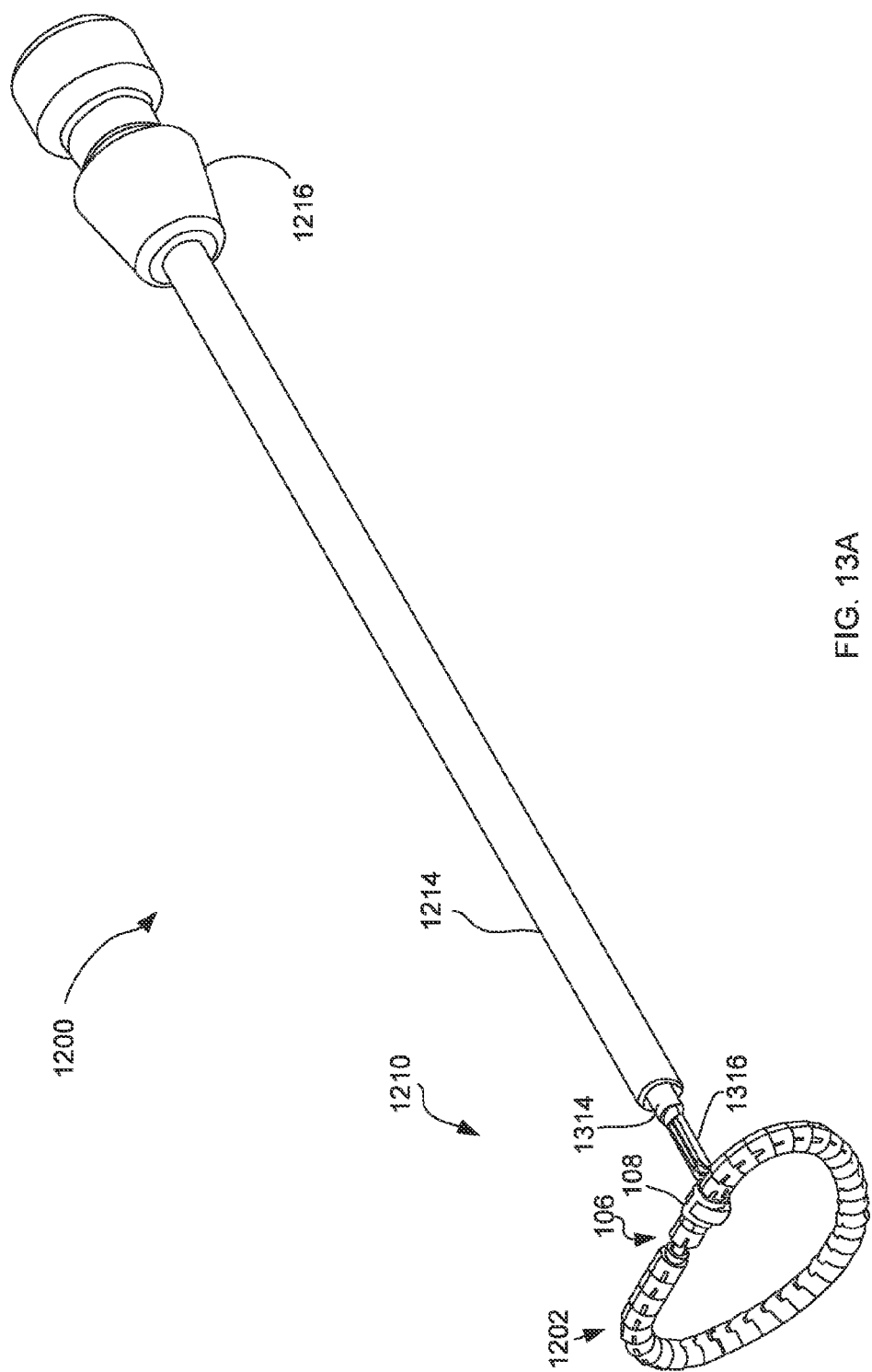

FIGS. 13A, 13B, 13C, 13D, 13E, 13F, and 13G are schematic diagrams illustrating the front of the delivery system 1200 shown in FIG. 12A according to certain embodiments. FIG. 13A illustrates a perspective view of the distal end 1210 of the delivery system 1200 up to the hemostatic connector 1216 of the proximal end. FIG. 13B illustrates an enlarged view of a portion of the distal end 1210 shown in FIG. 13A. The distal end 1210 includes a catheter shaft 1314 sized and configured to pass through the outer jacket delivery catheter 1214, a ring shuttle 1316 configured to be removably coupled to the pivot 108 of the segmented annuloplasty ring 1202, a first deployment lumen 1320 through which the first suture 1219 passes for snapping together the ends of the ring closure lock 106, a second deployment lumen 1324 through which the second suture 1221 passes for deploying anchors (not shown) as discussed above, and a third deployment lumen 1328 (FIG. 13C) through which the ring deployment wire 1223 passes for orienting the ring 1202 within the heart and releasing the ring 1202 from the ring shuttle 1316.

Figure 13C:
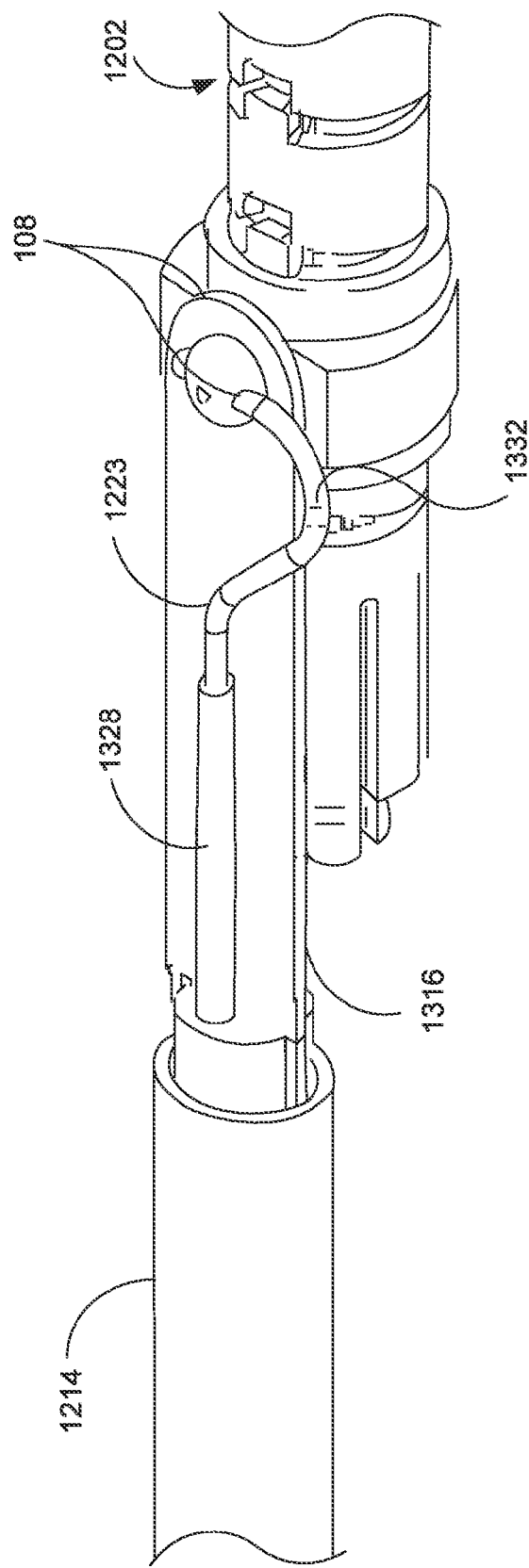

FIGS. 13A and 13B show a first side of the distal end of the ring shuttle 1316 including the first deployment lumen 1320 (for snap locking the ring 1202) and the second deployment lumen 1324 (for deploying anchors), with the ring 1202 in the annular operable geometry having its plane perpendicular to the longitudinal axis of the outer jacket delivery catheter 1214 and the catheter shaft 1314 (e.g., as it would be oriented inside the heart and aligned with the valve annulus). In FIG. 13C, a second side of the distal end of the ring shuttle 1316 is shown including the third deployment lumen 1328, with the ring 1202 in the elongate insertion geometry aligned with the longitudinal axis of the catheter shaft 1314 and ready to be loaded into the outer jacket delivery catheter shown in FIGS. 13A and 13B. In the configuration shown in FIG. 13C, the distal end of the ring deployment wire 1223 includes a bend or hook 1332 as it passes through a hole in the pivot 108. The ring deployment wire 1223 includes a superelastic shape memory material (e.g., Nitinol). As discussed below, bending the distal end of the ring deployment wire 1223 into the hook 1332 shape spring loads the ring 1202 within the outer jacket delivery catheter 1214 such that the ring 1202 automatically rotates about the pivot 108 upon exiting the outer jacket delivery catheter 1214.

Figure 13D:
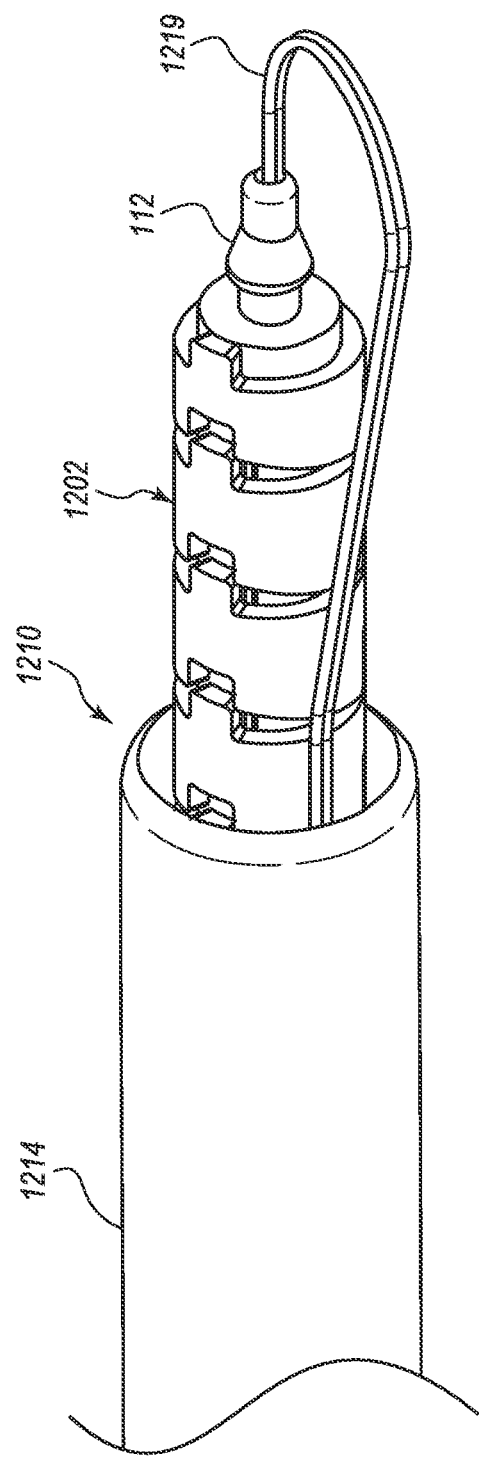

FIG. 13D is a perspective view of the ring 1202 partially deployed from the distal end 1210 of the outer jacket delivery catheter 1214 in a first deployment stage. In the first stage, the ring 1202 is still substantially in the elongate insertion geometry. As shown in FIG. 13D, the first suture 1219 for snapping together the ends of the ring 1202 passes through the male snap 112 of the ring closure lock 106.

Figure 13E:
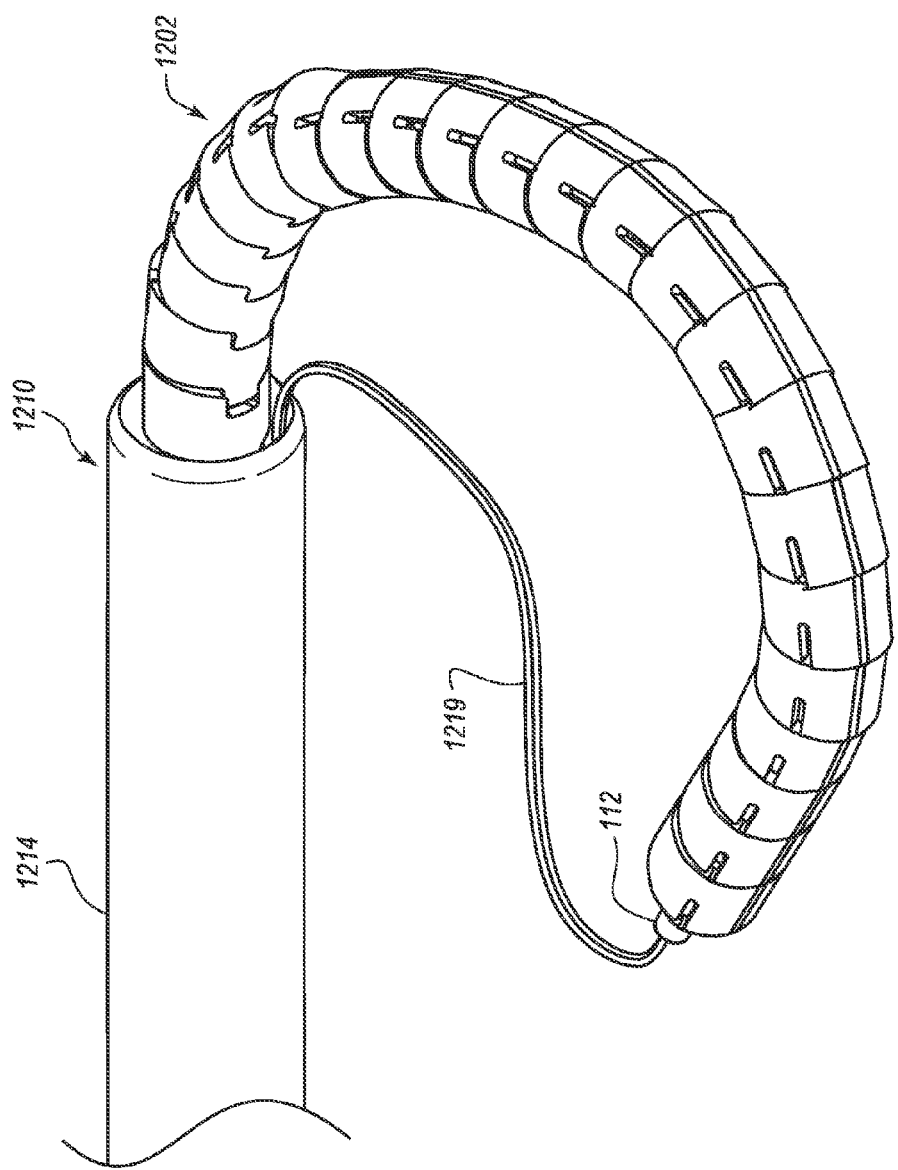

FIG. 13E is a perspective view of the ring 1202 in a second stage of partial deployment from the outer jacket delivery catheter 1214. In the second stage, the portion of the ring 1202 that has exited the outer jacket delivery catheter 1214 has begun to transition (due to the shape memory materials used in the ring 1202) from the elongate insertion geometry to the annular operable geometry. The ring 1202 may include a window (not shown), e.g., laser cut through the outer hypotube along with the plurality of segments, that allows the first suture 1219 to exit the ring 1202.

Figure 13F:
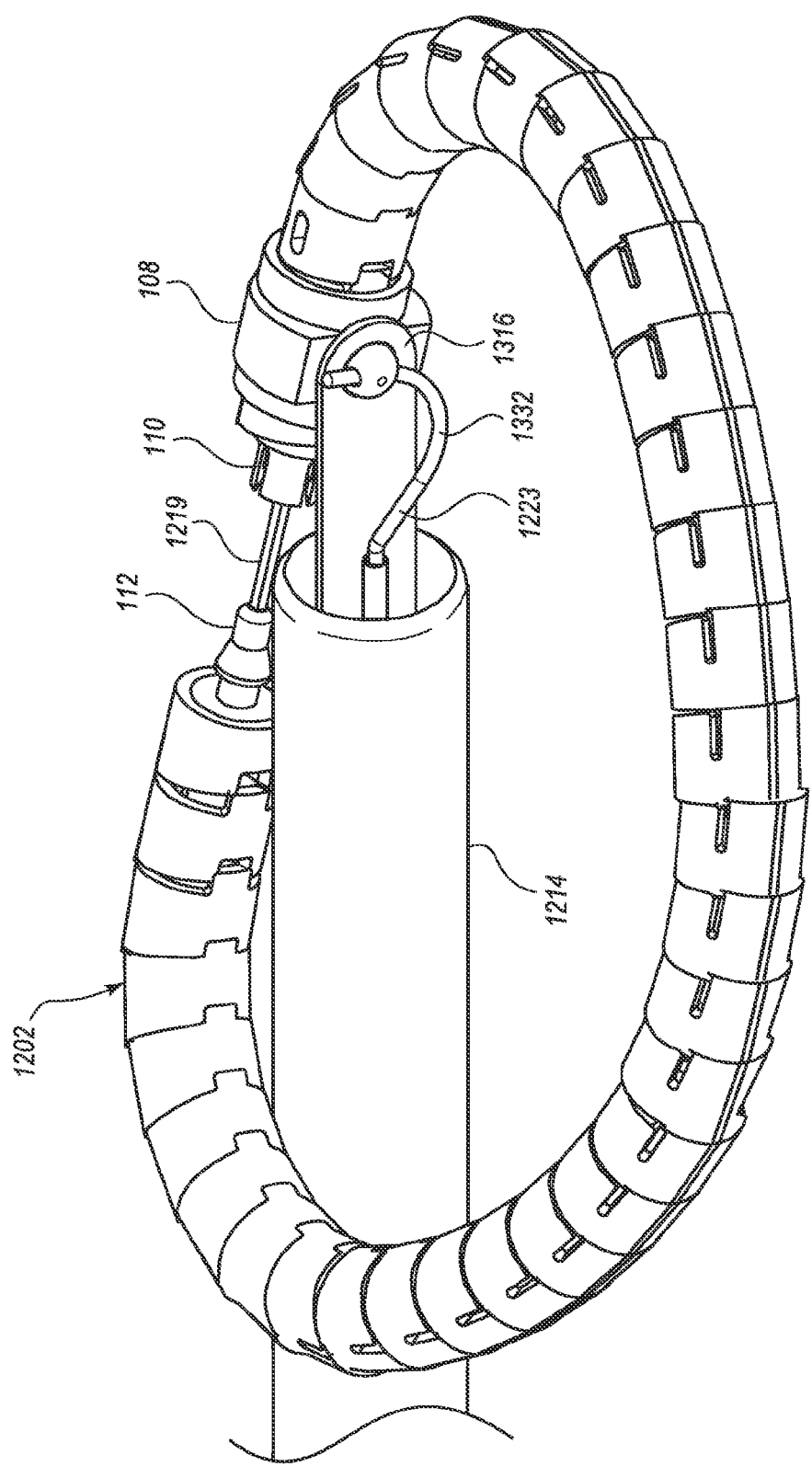

FIG. 13F is a perspective view of the ring 1202 in a third stage of deployment in which the ring shuttle 1316 has substantially pushed the ring 1202 out of the outer jacket delivery catheter 1214, but the plane of the ring 1202 is still aligned with (e.g., approximately parallel to) the longitudinal axis of the outer jacket delivery catheter 1214. This example shows the configuration immediately before the ring deployment wire 1223 cooperates with the pivot 108 to rotate the ring 1202 (see FIG. 13G). At this stage, the hook 1332 shape in the superelastic ring deployment wire 1223 is ready to unload (return to its straight configuration) as soon as the outer jacket delivery catheter 1214 no longer prevents it from doing so.

Figure 13G:
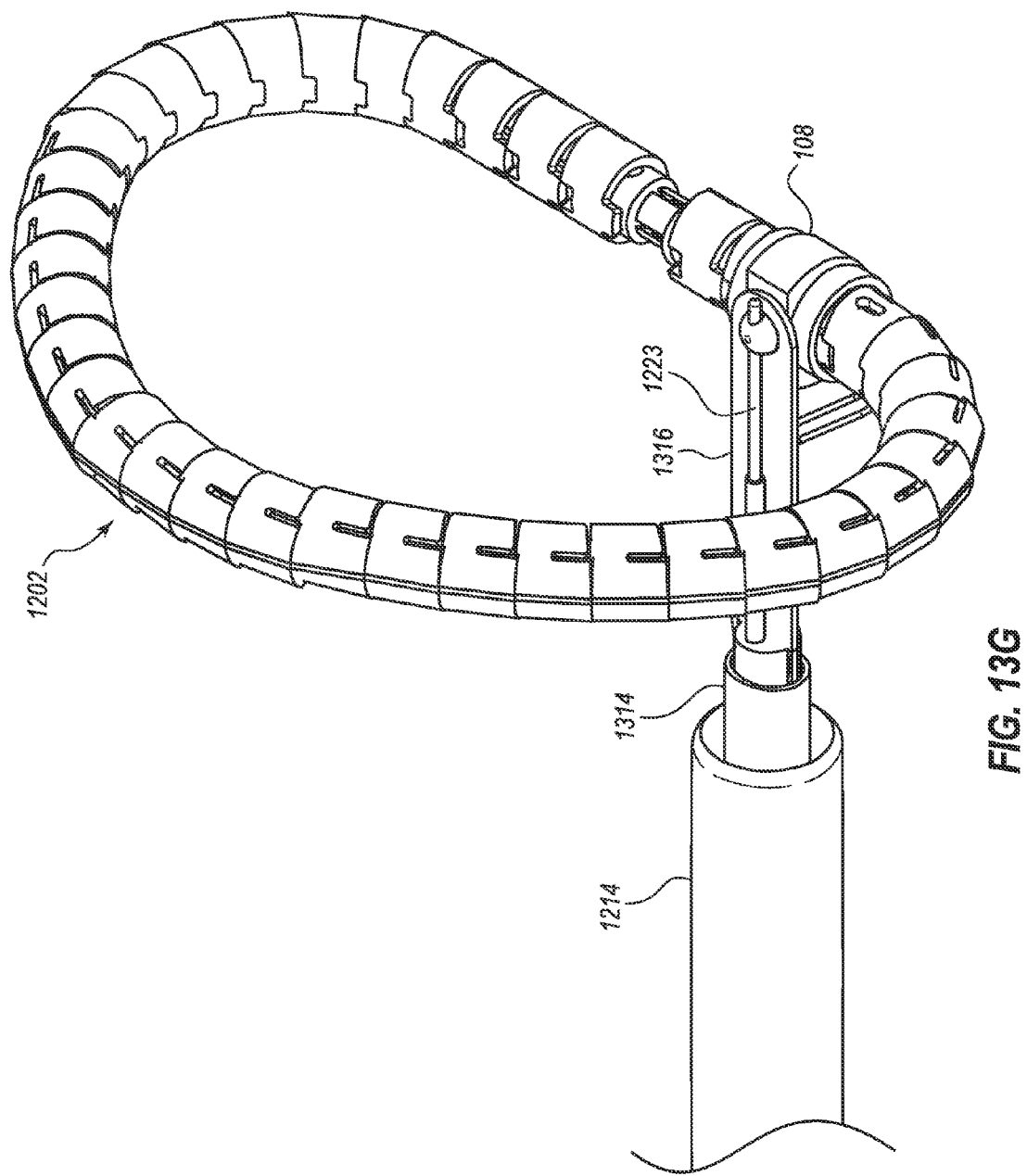

FIG. 13G is a perspective view of the ring 1202 in a fourth stage of deployment in which the plane of the ring 1202 (in its annular operable geometry) has been changed to be perpendicular to the longitudinal axis of the outer jacket delivery catheter 1214. As shown in FIG. 13G, the superelastic ring deployment wire 1223 has returned to its heat set (memorized) straight configuration. At this stage, the axis of the ring 1202 is parallel to the plane of the heart valve annulus.

In further stages of deployment, the ring 1202 may be pressed against (e.g., using a balloon) the heart valve annulus before deploying the anchors (such as the curved anchors 104 shown in FIGS. 4A and 4B) by pulling the second suture 1221 toward the proximal end of the second deployment lumen 1324. As discussed above, certain anchor embodiments propel themselves into the tissue of the heart valve annulus upon being deployed. In other embodiments, the anchors (such as the linear anchors 710 shown in FIG. 7) may be deployed before pressing the ring 1202 against the annulus. After the ring 1202 is anchored to the heart valve annulus (or after a balloon is holding the ring against the annulus), the ring deployment wire 1223 may be pulled from the hole in the pivot 108 to release the ring 1202 from the ring shuttle 1316. The first suture 1219 and the second suture 1221 may also be cut and/or pulled from the ring 1202 before the catheters 1214, 1314 are removed from the heart.

FIGS. 14A, 14B, 14C, 14D, 14E, 14F, and 14G are schematic diagrams illustrating perspective, partially cross-section views of a heart 1100 during the introduction and affixation of a segmented annuloplasty ring 1400 to the annulus of the mitral valve 1110 according to certain embodiments. As shown, an outer jacket delivery catheter 1410 extends from the left ventricle into the left atrium through the leaflets of the mitral valve 1110. Thus, this illustrated embodiment may correspond to, for example, a trans-apical approach or a retrograde approach, as discussed above. Artisans will recognize from the disclosure herein, however, that similar principles as those illustrated may be used for trans-septal approaches.

Figure 14A:
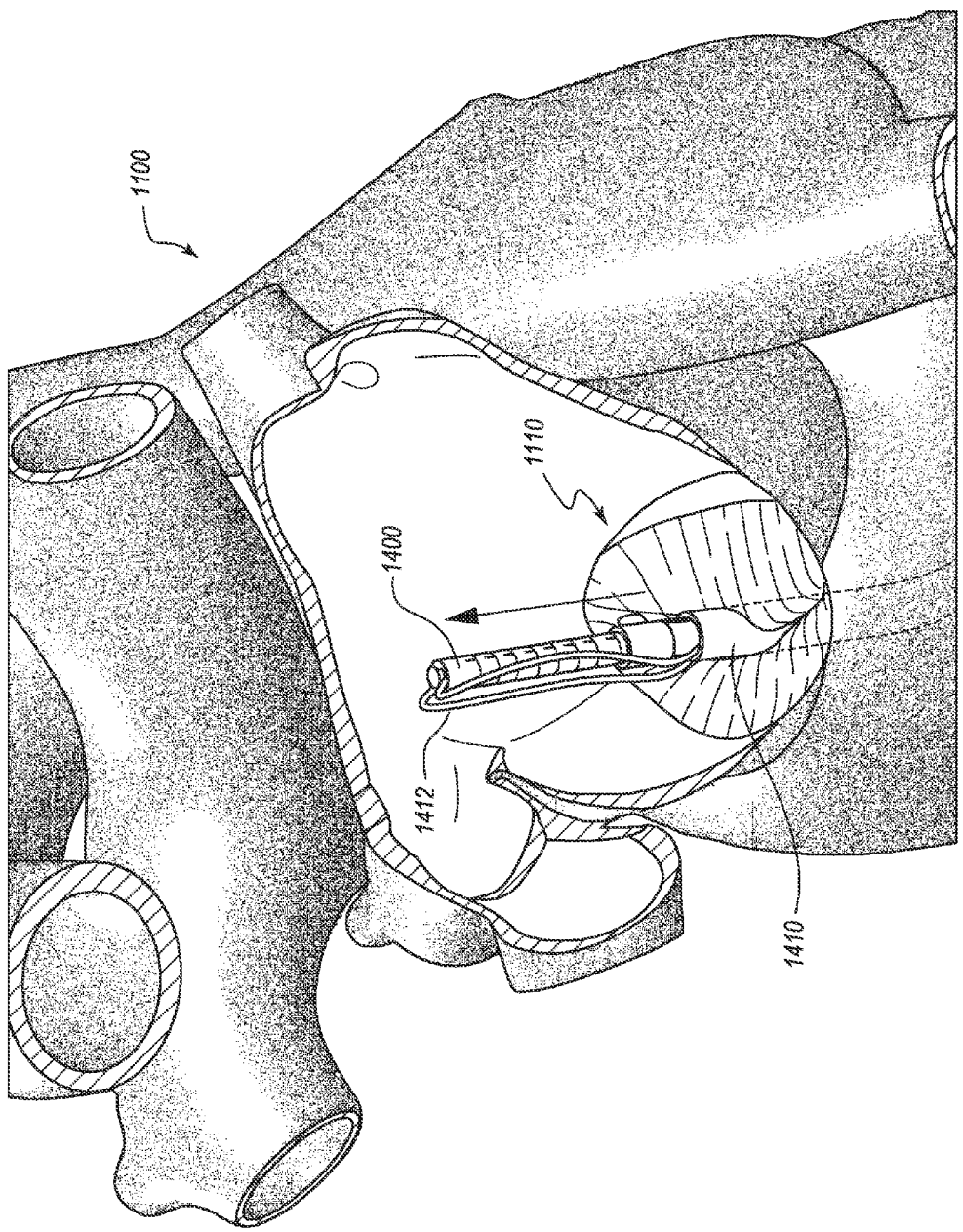

In FIG. 14A, the ring 1400 is in an elongate insertion geometry as it is pushed into the left atrium from a distal end of the catheter tube 1410. As discussed herein, a wire or suture 1412 used for snapping together the ends of the ring 1400 is shown extending from a first end of the ring 1410. FIG. 14B shows the ring 1400 partially deployed from the catheter 1410. As discussed above, the superelastic shape memory components of the ring 1400 cause the exposed end of the ring 1400 to return to its annular shape (D-shape) as it exits the catheter 1410.

Figure 14C:
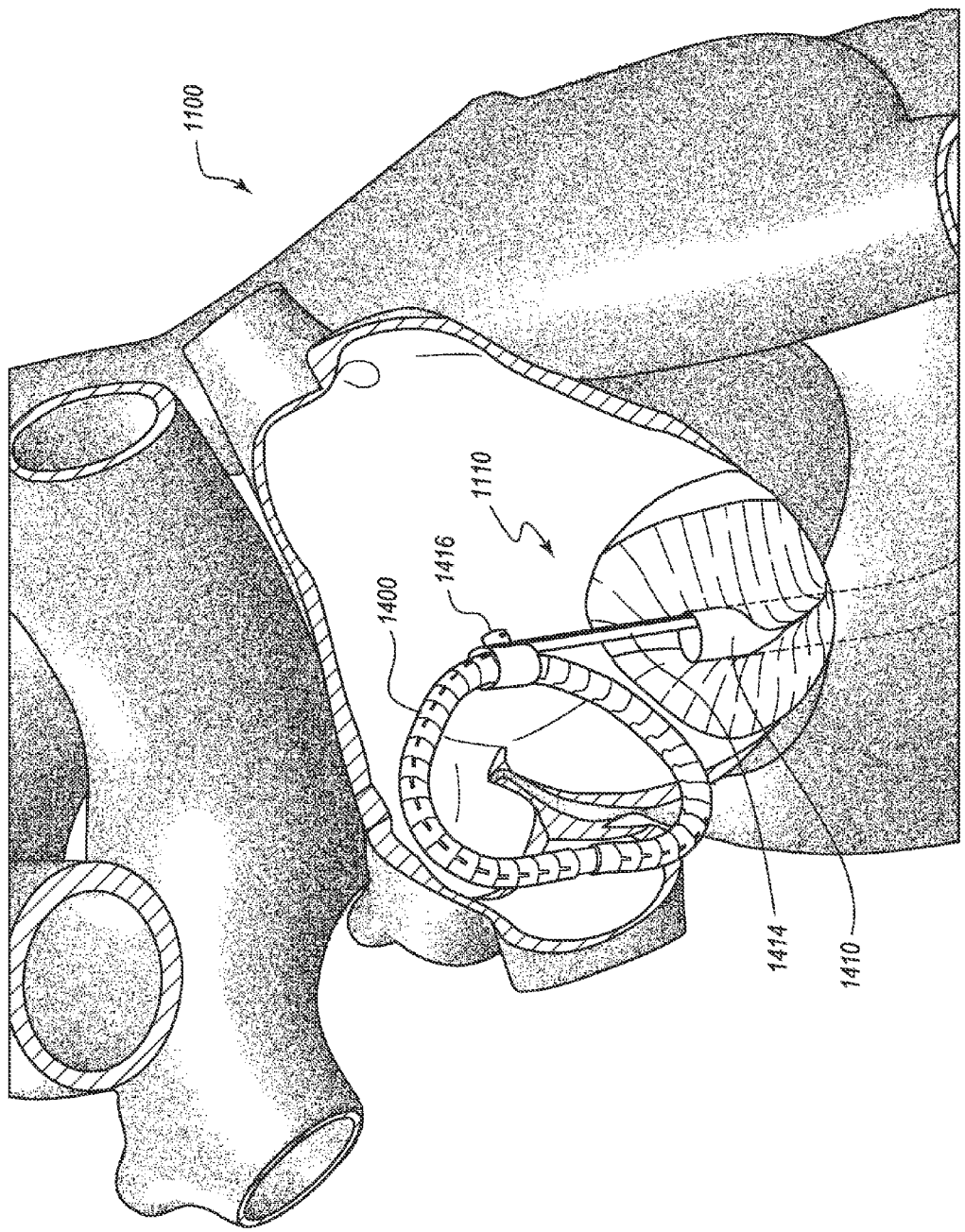

FIG. 14C illustrates the ring 1400 fully deployed from the catheter 1410 and transitioned from the elongate insertion geometry to the D-shape operable geometry. In this embodiment, the suture 1412 (shown in FIGS. 14A and 14B) has been pulled so as to snap together the two ends of the ring 1400. In other embodiments, however, the ends of the ring 1400 are not snapped together until the ring 1400 has been anchored in place to the valve annulus. See, for example, FIGS. 16B and 17.

For illustrative purposes, the plane of the ring 1400 in FIG. 14C is shown as parallel to the longitudinal axis of the catheter 1410 and an inner catheter shaft 1414. In this position, the plane of the ring 1400 may be considered as perpendicular or substantially perpendicular to the valve annulus. In other words, the plane of the ring 1400 as shown in FIG. 14C is substantially perpendicular to the direction of blood flow through the mitral valve 1110. As discussed above, the inner catheter shaft 1414 (e.g., via a ring shuttle) is coupled to and cooperates with the 1416 to automatically rotate the ring 1400 as it exits the outer catheter 1410 so that the plane of the ring 1400 is parallel to the plane of the valve annulus, as shown in FIG. 14D. In other words, in FIG. 14D, the plane of the ring 1400 is substantially parallel to the blood flow through the mitral valve 1110. In FIG. 14D, a ring deployment wire 1413 is shown, such as the ring deployment wire 1223 discussed above. For clarity, the ring deployment wire 1413 is not shown in FIG. 14C.

Figure 14E:
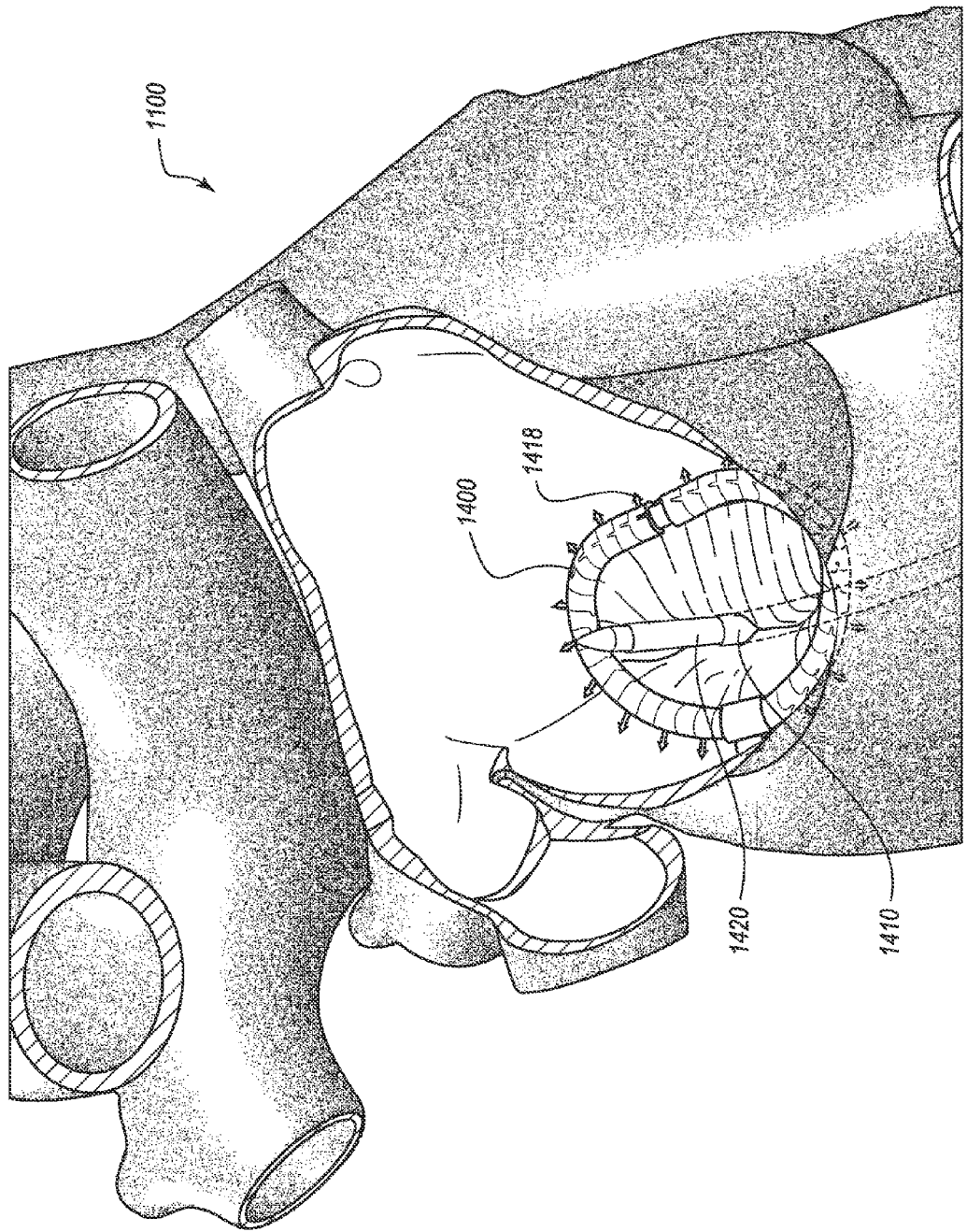

FIG. 14E illustrates the ring 1400 positioned on or next to the annulus of the valve 1110 with the anchors 1418 deployed. At this stage, in this embodiment, the anchors 1418 are either not embedded within the annulus tissue or are only partially inserted within the annulus tissue. In other embodiments, however, the anchors 1418 self-propel themselves into the annulus tissue when deployed. See, e.g., FIGS. 16B and 17. FIG. 14E shows a balloon catheter 1420 extending through the distal end of the outer catheter 1410.

Figure 14F:
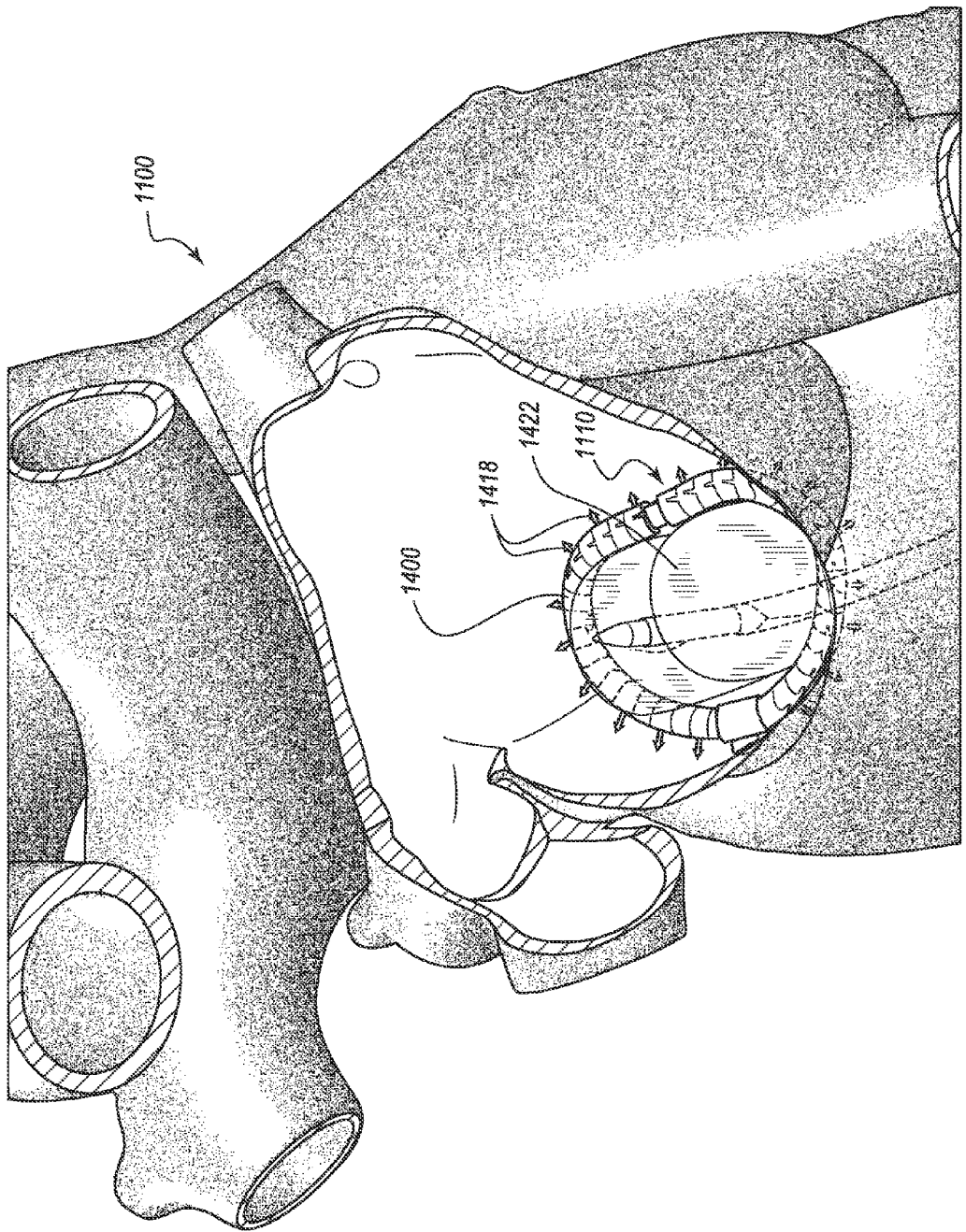
Figure 14G:
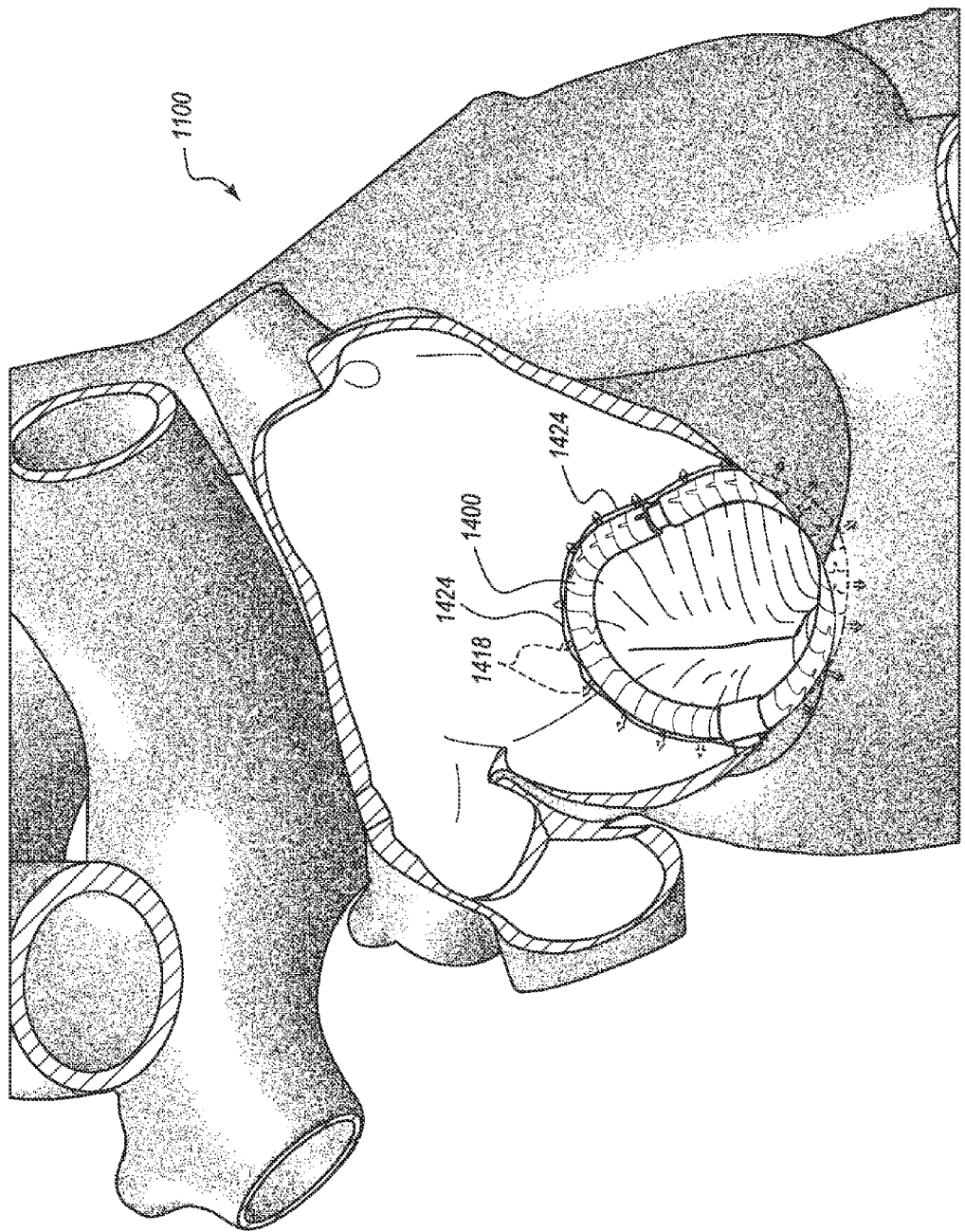

FIG. 14F shows a balloon 1422 of the balloon catheter 1420 in the process of being inflated and driving the anchors 1418 into the annulus tissue around the valve 1110. FIG. 14G graphically illustrates the anchors 1418 embedded within the tissue 1424 (see FIG. 14G) of the valve annulus. In FIG. 14G, the catheters have been removed and the ring 1400 is securely attached to the annulus of the mitral valve 1110 to restore the valve opening to its approximate original size and operating efficiency.

Figure 15:
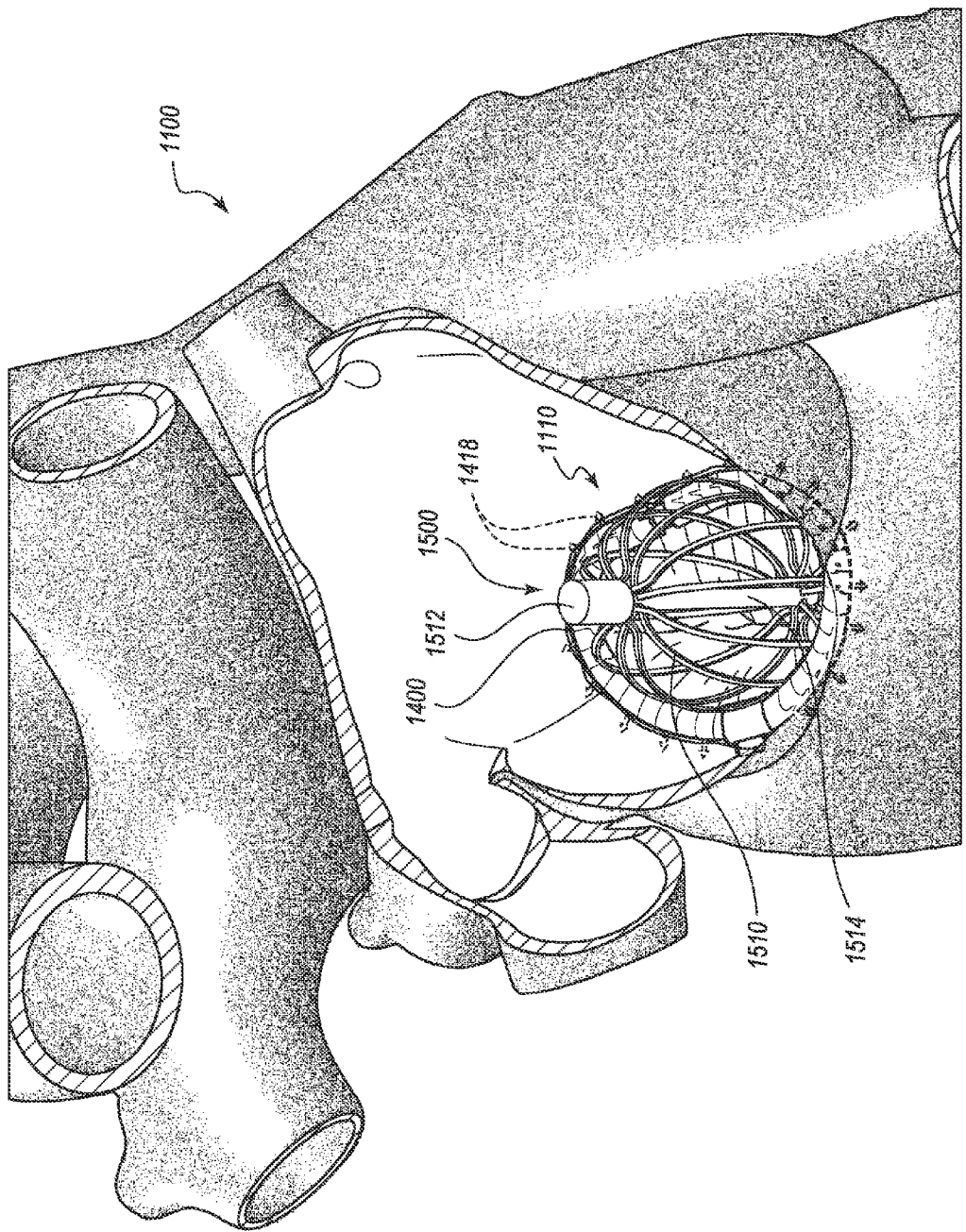
FIG. 15 is a schematic diagram illustrating a perspective, partially cross-section view of the heart during the introduction and affixation of the segmented annuloplasty ring using an expandable cage or basket, instead of the balloon shown in FIG. 14F, according to one embodiment.

The balloon shown in FIG. 14F includes two sections and may be considered a "multi-chamber" balloon with two chambers. In other embodiments, a balloon with a single chamber or a balloon with more than two chambers may be used to position the ring 1400 against the valve annulus and/or to drive the anchors 1418 into the surrounding tissue. In the embodiment shown in FIG. 14F, the inflated balloon 1422 may reduce or prevent the flow of blood through the mitral valve during at least part of the implantation procedure. In such embodiments, inflation of the balloon 1422 may last 20 seconds or less to prevent adverse consequences of occluding the mitral valve. In other embodiments, blood is allowed to flow through the mitral valve during the entire procedure. For example, FIG. 15 is a schematic diagram illustrating a perspective, partially cross-section view of the heart 1100 during the introduction and affixation of the segmented annuloplasty ring 1400 using an expandable cage or basket 1500, instead of the balloon shown in FIG. 14F, according to one embodiment. The basket 1500 includes a plurality of flexible members 1510 that lay flat against a central rod 1514 during insertion of the basket 1500 through the catheter 1410 (shown in FIG. 14A) and may be forced into an expanded configuration (shown in FIG. 15) when the central rod 1514 is pushed into an end cap 1512. In another embodiment, the plurality of flexible members 1510 comprise a superelastic material so as to spring from the catheter 1410 into the expanded configuration shown in FIG. 15.

Figure 16A:
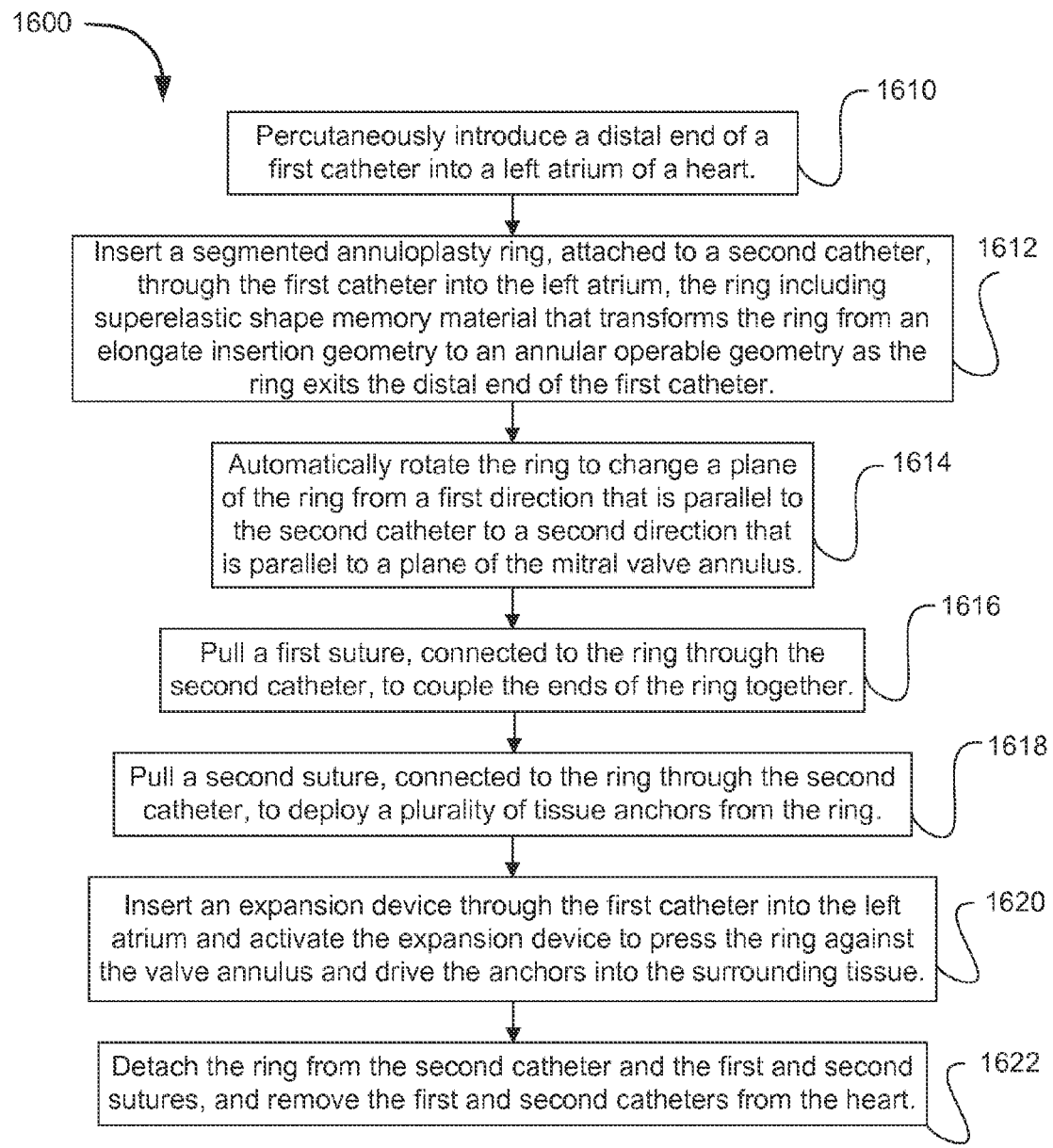
FIG. 16A is a flowchart of a method for repairing a defective heart valve according to one embodiment.

FIG. 16A is a flowchart of a method 1600 for repairing a defective heart valve according to one embodiment. The method 1600 includes percutaneously introducing 1610 a distal end of a first catheter into a left atrium of a heart and inserting 1612 a segmented annuloplasty ring, attached to a second catheter, through the first catheter into the left atrium. The ring includes a superelastic shape memory material that transforms the ring from an elongate insertion geometry to an annular operable geometry as the ring exits the distal end of the first catheter. The method 1600 further includes automatically rotating 1614 the ring to change a plane of the ring from a first direction that is parallel to the second catheter to a second direction that is parallel to a plane of the mitral valve annulus, and pulling 1616 a first suture, connected to the ring through the second catheter, to couple the ends of the ring together. The method 1600 includes pulling 1618 a second suture, connected to the ring through the second catheter, to deploy a plurality of tissue anchors from the ring. Then, inserting 1620 an expansion device through the first catheter into the left atrium and activating the expansion device to press the ring against the valve annulus and drive the anchors into the surrounding tissue. The method 1600 further includes detaching 1622 the ring from the second catheter and the first and second sutures, and remove the first and second catheters from the heart.

Figure 16B:
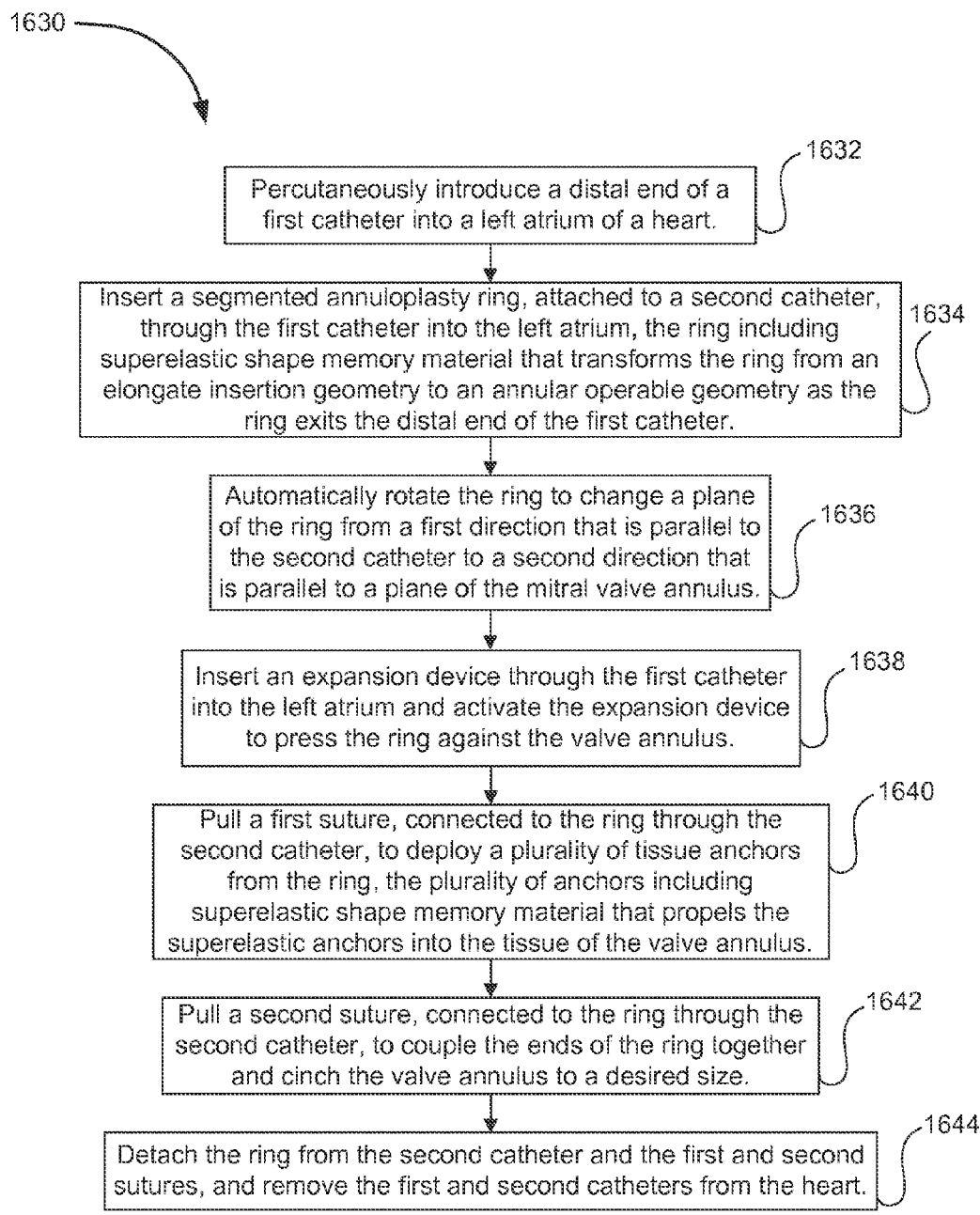
FIG. 16B is a flowchart of a method for repairing a defective heart valve according to another embodiment.

FIG. 16B is a flowchart of a method 1630 for repairing a defective heart valve according to another embodiment. The method 1630 includes percutaneously introducing 1632 a distal end of a first catheter into a left atrium of a heart, and inserting 1634 a segmented annuloplasty ring, attached to a second catheter, through the first catheter into the left atrium. The ring includes superelastic shape memory material that transforms the ring from an elongate insertion geometry to an annular operable geometry as the ring exits the distal end of the first catheter. The method 1630 further includes automatically rotating 1636 the ring to change a plane of the ring from a first direction that is parallel to the second catheter to a second direction that is parallel to a plane of the mitral valve annulus, and inserting 1638 an expansion device through the first catheter into the left atrium and activating the expansion device to press the ring against the valve annulus. Pressing the ring against the annulus at this stage allows the subsequent deployment of the anchors to propel the anchors into the annulus tissue. Thus, the method 1630 further includes pulling 1640 a first suture, connected to the ring through the second catheter, to deploy a plurality of tissue anchors from the ring. Each of the plurality of anchors includes a superelastic shape memory material that propels the superelastic anchors into the tissue of the valve annulus. The method 1630 further includes pulling 1642 a second suture, connected to the ring through the second catheter, to couple the ends of the ring together and cinch the valve annulus to a desired size. The method 1630 also includes detaching 1644 the ring from the second catheter and the first and second sutures, and removing the first and second catheters from the heart.

Figure 17:
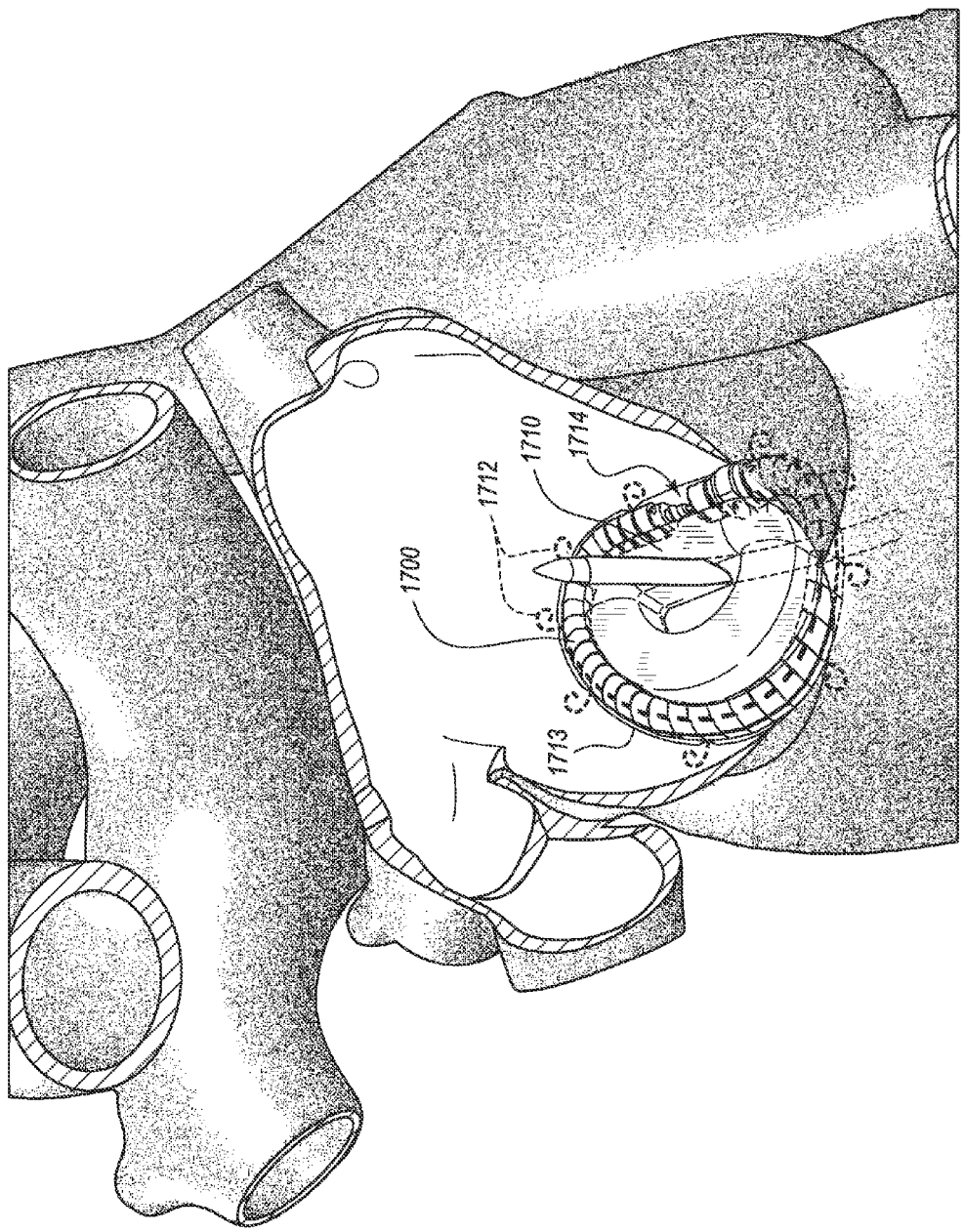
FIG. 17 is a schematic diagram illustrating a perspective, partially cross-section view of the heart during the introduction and affixation of a segmented annuloplasty ring according to another embodiment.

FIG. 17 is a schematic diagram illustrating a perspective, partially cross-section view of the heart 1100 during the introduction and affixation of a segmented annuloplasty ring 1700 according to another embodiment. In this embodiment, a balloon 1710 is inflated before anchors 1712 are deployed. The balloon 1710 in this embodiment is "donut-shaped" (i.e., it includes a central opening) to allow blood to flow through the valve during the entire procedure. With the ring 1700 pressed against the valve annulus, the anchors 1712 are deployed. As discussed above, the anchors 1712 comprises a superelastic shape memory material that assists in driving the anchors 1712 into valve annulus tissue 1713. For illustrative purposes, the anchors 1712 in FIG. 17 are shown with dashed lines to represent being embedded within the tissue 1713.

Additional Example Embodiments

Figure 18:
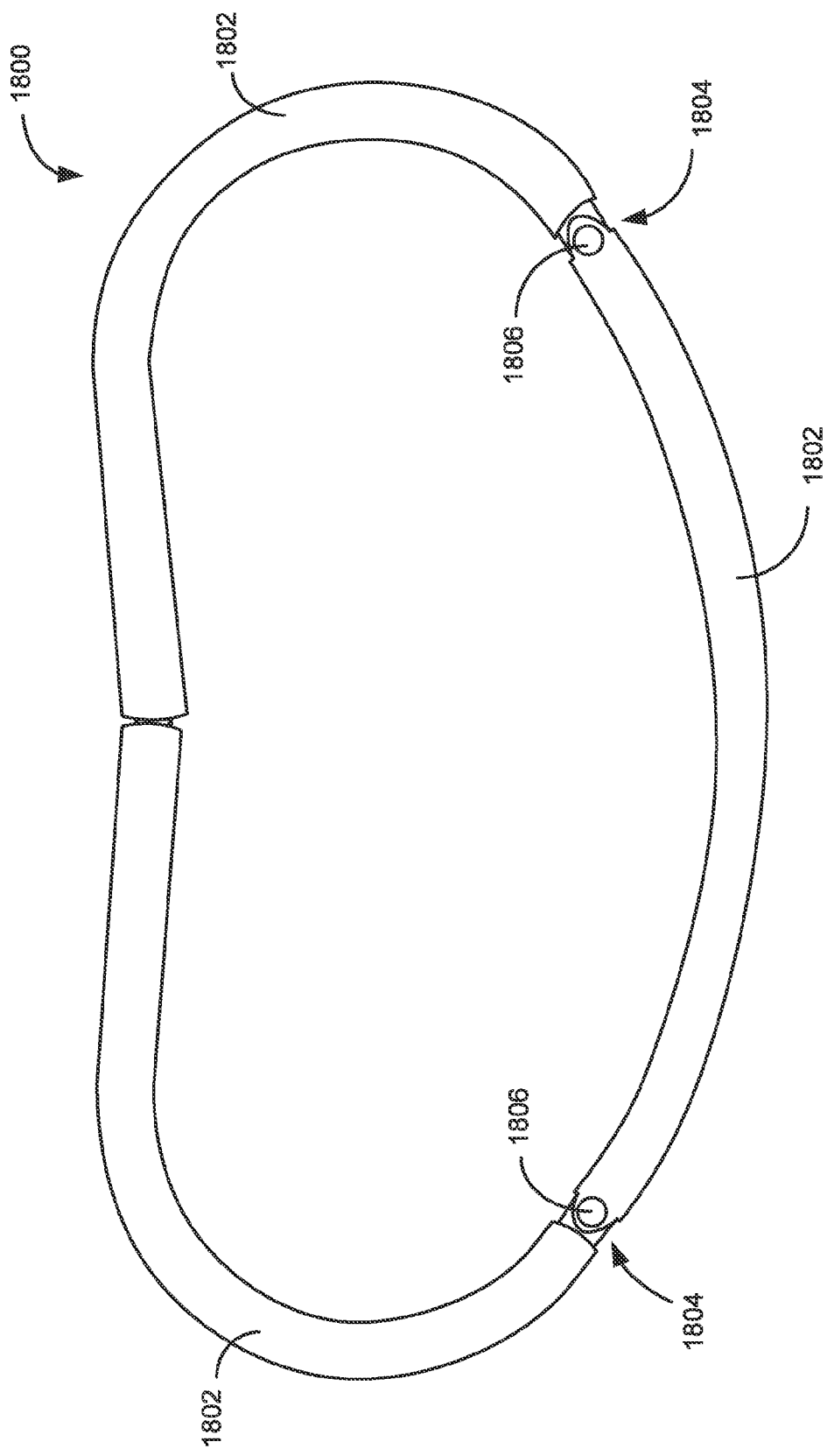
FIG. 18 is a schematic diagram of a percutaneous transcatheter annuloplasty ring in an annular operable geometry according to one embodiment.

FIG. 18 is a schematic diagram of a percutaneous transcatheter annuloplasty ring 1800 in an annular operable geometry according to one embodiment. The annuloplasty ring 1800 can be affixed to heart tissue in and/or around a defective heart valve to treat (e.g., reduce) regurgitation of blood through leaflets of the heart valve. For example, the annuloplasty ring 1800, in the operable geometry, may be affixed to the annulus of the heart valve and used to cinch the annulus to draw the opening smaller or into an improved shape that reduces regurgitation of blood back through the valve. FIG. 19A is a schematic diagram illustrating the percutaneous transcatheter annuloplasty ring 1800 of FIG. 18 in an insertion geometry according to one embodiment. FIG. 19B is a schematic diagram of the percutaneous transcatheter annuloplasty ring 1800 transitioning from the insertion geometry shown in FIG. 19A to the operable geometry shown in FIG. 18 according to one embodiment.

Referring generally and collectively to FIGS. 18, 19A, and 19B, the annuloplasty ring 1800 may include a plurality of segments 1802 flexibly coupled together. Flexible coupling of the plurality of segments 1802 may be accomplished with a plurality of hinges 1804. The annuloplasty ring 1800 may further include a securement mechanism 1806, such as a pin or clasp, to couple together ends of the annuloplasty ring 1800 to form the annular operable geometry. In the displayed example, the hinges 1804 comprise pin joints and the securement mechanisms 1806 comprise pins. The plurality of segments 1802 and plurality of hinges 1804 allow the annuloplasty ring 1800 to unfold or open from a curved and/or annular operable geometry into an elongate flexible insertion geometry as illustrated in FIG. 19A.

The plurality of segments 1802 may be arranged in a serial or linear arrangement (e.g., a chain of interconnected segments 1802) having a first end 1920 and a second end 1922. The plurality of segments 1802 may be formed of a biocompatible material, or a combination of multiple biocompatible materials, including but not limited to Nitinol and plastic. The plurality of segments 1802 may be formed to enhance flexibility when in the insertion geometry and to enhance rigidity when in the operable geometry. The plurality of segments 1802 and/or the annuloplasty ring 1800 may include shape memory material to bias or otherwise aid in transitioning the annuloplasty ring 1800 to the curved operable geometry.

The plurality of hinges 1804 couple together the plurality of segments 1802. Each segment 1802 may be coupled to an adjoining segment via a corresponding hinge 1804. The hinges 1804 may be configured to facilitate folding or closing the annuloplasty ring 1800 to transition between the insertion geometry and the operable geometry, as shown in FIG. 19B. In certain embodiments, each of the plurality of hinges 1804 is configured to lock into a secured state when the associated (adjoining) segments 1802 are in the operable geometry. Thus, a hinge 1804 may allow adjoining segments 1802 to freely rotate within a range of motion to provide flexibility, and the hinge 1804 may lock to limit rotation of the adjoining segments 1802 and provide rigidity when rotation of the adjoining segments exceeds the range of motion and the adjoining segments 1802 are in their respective positions of the operable geometry. In another embodiment, the plurality of hinges 1804 may include a flexible piece of material. For example, a hinge 1804 may be formed of a portion of the same material as the plurality of segments 1802. In still another embodiment, the plurality of hinges 1804 are integrated with, or formed integrally with, the plurality of segments 1802. For example, the plurality of segments 1802 and the plurality of hinges 1804 may be cut from a single piece of material, such as a Nitinol tube.

A ring closure lock 1910 secures the first end 1920 to the second end 1922 to form the circular or annular shape of the operable geometry. The ring closure lock 1910 of the illustrated embodiment is a snap-lock in which a ball 1912 (male snap) on the second end 1922 is received and snaps into a mating socket 1914 (female snap) on the first end 1920 when the ball 1912 is urged toward and into the socket 1914 with sufficient force. In another embodiment, the ring closure lock 1910 may include a clasp or other locking mechanism. In another embodiment, the ring closure lock 1910 may be any locking mechanism that allows a first component to easily slide past a second component in a first direction but that prevents the first component from sliding back in the opposite direction past the second component. In another embodiment, the ring closure lock 1910 may include magnets configured to attract the ends 1920, 1922 together.

A ring closing mechanism 1916, such as a suture or wire, may be mounted across the ends 1920, 1922 to facilitate bringing the ends 1920, 1922 of the annular ring 1800 together and engagement of the ring closure lock 1910. In the illustrated embodiment, the ring closing mechanism 1916 may be a suture. The suture 1916 may be configured and arranged through an eyelet 1932 or hook (or around a knob) on the second end 1922. The ends of the suture 1916 may also be threaded through an eyelet 1930 on the first end 1920 and back through the catheter out of the patient's body. The ends of the suture 1916 may be pulled or otherwise manipulated by a practitioner from external to the patient's body to draw the second end 1922 toward the first end 1920. In this manner, the ball 1912 can be forced into the socket 1914 to secure the ends 1920, 1922 together and the annuloplasty ring 1800 in the operable geometry. Once the ring lock closure is secured (e.g., locked) in place, one end of the suture 1916 can be pulled to pull the suture 1916 through the eyelets 1930, 1932 and out of the patient's body.

The operable geometry of the annuloplasty ring 1800 may be curved to align or substantially conform to the sized and/or shape of an annulus of a properly functioning heart valve of the type to be repaired. In the illustrated embodiment, the operable geometry is circular or annular, as shown in FIG. 18. The operable geometry may be designed and configured to provide structure and rigidity to properly cinch and/or support a defective valve to correct regurgitation of blood back through the valve. In one embodiment, the operable geometry provides rigidity in at least a direction transverse to a plane of the curved shape of the operable geometry. The plane of the curved shape may be defined by a longest diameter of the curved shape and a second diameter of the curved shape that is perpendicular to the first diameter. Stated differently, the operable geometry may provide rigidity along (e.g., in a direction parallel to) a circumferential axis of the curved shape. The circumferential axis may be defined through the center of the opening of the ring and extending parallel to a direction of a flow of blood through the annuloplasty ring 1800 when it is properly implanted in the heart valve. In FIG. 18, the circumferential axis may be defined by a line extending from the center of the annuloplasty ring 1800 directly out of and perpendicular to the page. The annuloplasty ring 1800 in the operable geometry may, in one embodiment, be rigid radially relative to the circumferential axis. In another embodiment, the operable geometry may be flexible radially relative to the circumferential axis.

The insertion geometry, as shown in FIG. 19A, allows the annuloplasty ring 1800 to be flexible and in an elongate and somewhat linear state to be inserted into a catheter tube. An annuloplasty ring, such as annuloplasty ring 1800, disposed in a catheter tube can be delivered and affixed to the defective heart valve via a percutaneous transcatheter delivery method. More specifically, a tip of a catheter tube of a delivery apparatus can be percutaneously inserted into a vascular structure of a vasculature of a body of a patient. The catheter tube of the delivery apparatus can be guided through the vasculature of the patient into a chamber of a heart of the patient and adjacent to the defective heart valve to be repaired. For example, delivery of the annuloplasty ring to the mitral valve may be accomplished via retrograde approach from the femoral artery, or an antegrade approach via a trans-septal entry. As another example, delivery of the annuloplasty ring into the tricuspid valve may be accomplished via an approach from the inferior or superior vena cava.

The annuloplasty ring 1800 may be configured to enable cinching of the heart tissue proximate the valve and/or cinching of the annulus of the valve, after affixation of the annuloplasty ring 1800 (e.g., postoperatively), to reduce regurgitation of blood back through leaflets of the valve.

Figure 20A:
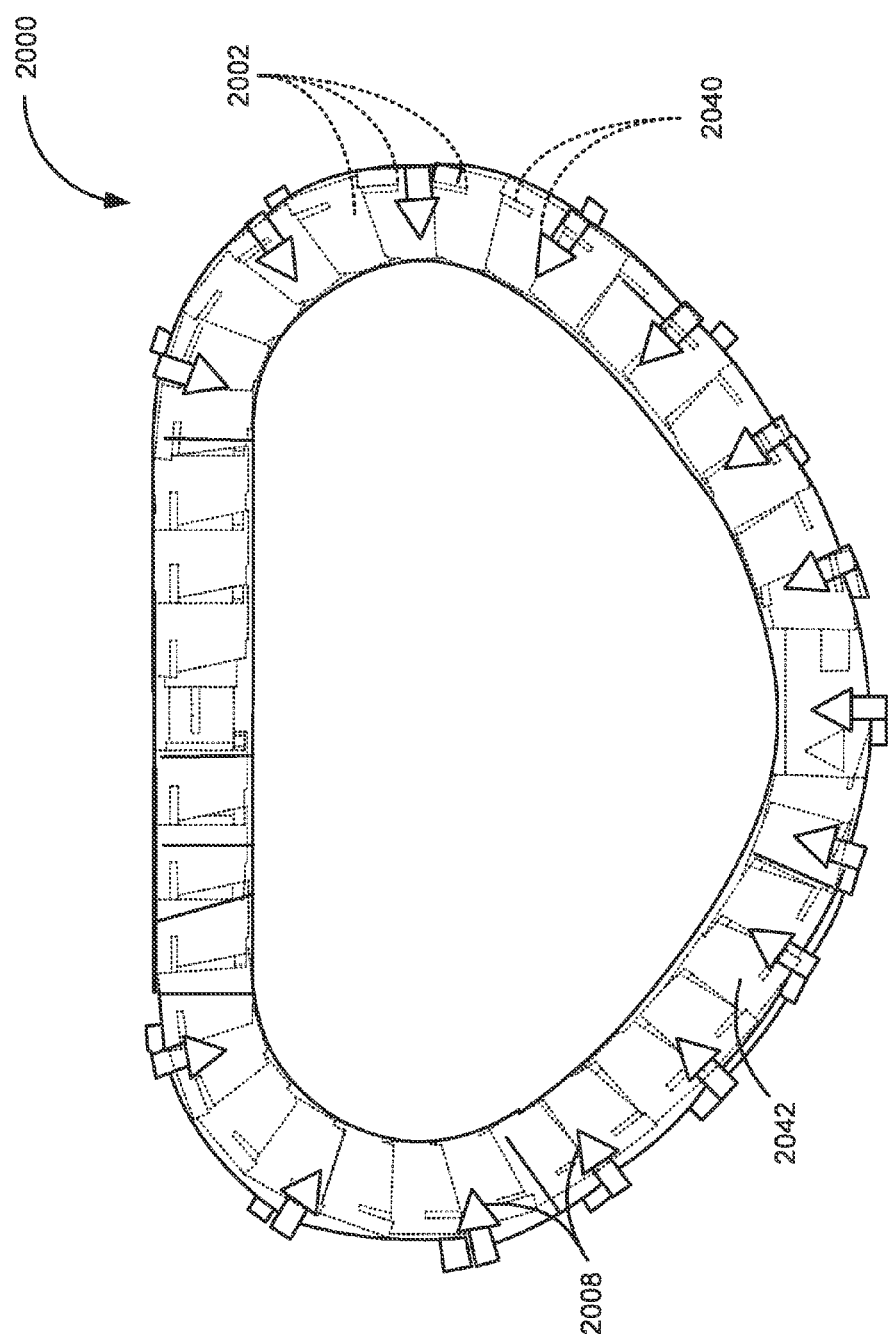
FIG. 20A is a schematic diagram illustrating a percutaneous transcatheter annuloplasty ring according to another embodiment.
Figure 20B:
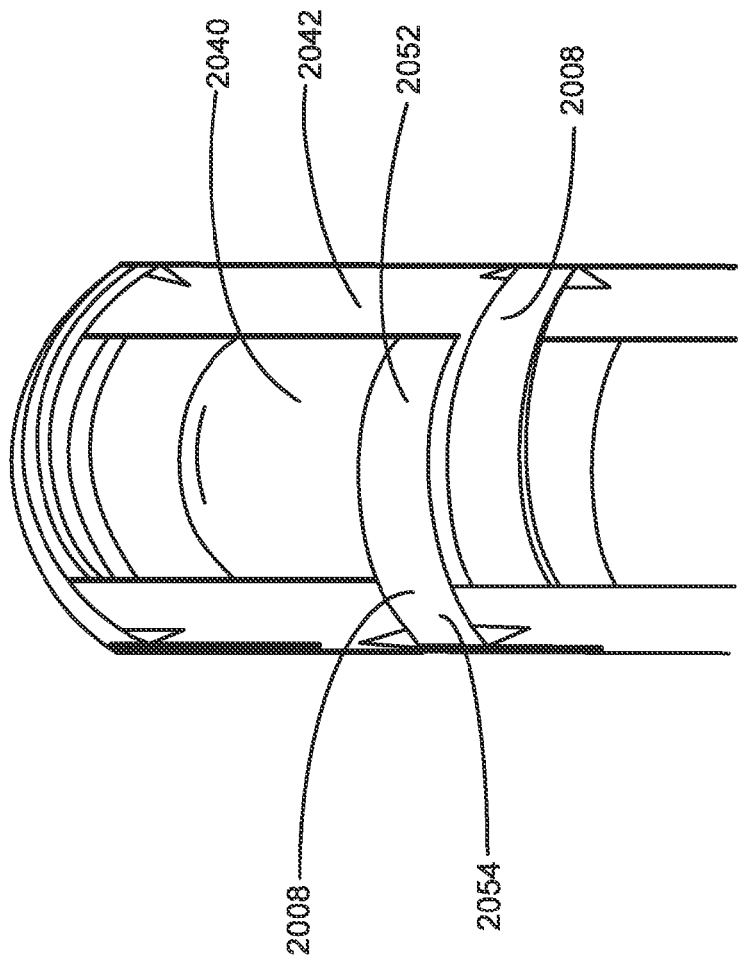
FIG. 20B is a schematic diagram illustrating an enlarged side view of the annuloplasty ring of FIG. 20A according to one embodiment.

FIG. 20A is a schematic diagram illustrating a percutaneous transcatheter annuloplasty ring 2000 according to another embodiment. The annuloplasty ring 2000 is shown in FIG. 20A in an annular operable geometry with anchors 2008 in an introduction configuration. FIG. 20B is a schematic diagram illustrating an enlarged side view of the annuloplasty 2000 ring of FIG. 20A. The annuloplasty ring 2000 may include an inner support structure 2040 and an outer shell 2042. In FIG. 20A, the inner support structure 2040 is shown in phantom lines as being hidden by the outer shell 2042. The inner support structure 2040 may be formed of a plurality of segments 2002, as shown in FIG. 1D and discussed more fully in other embodiments disclosed herein. The outer shell 2042 may be formed of a thin super-elastic material, such as Nitinol. The anchors 2008 may extend from and/or be integrated with the outer shell 2042. Superelastic shape memory material in the plurality of segments 2002 of the inner support structure 2040 and/or the outer shell 2042 enable the annuloplasty ring 2000 to transition between an insertion geometry and an operable geometry.

The anchors 2008, when in an introduction configuration, may be folded or wrapped to lie in close proximity to the outer shell 2042, as shown in FIG. 20B, so as to not protrude away from the surface of the annuloplasty ring 2000. The anchors 2008 may include a prong 2052 and a barb 2054 at an end of the prong. The barb 2054 may facilitate securement of the anchor 2008 in tissue.

FIG. 20C is a schematic diagram of the annuloplasty ring 2000 of FIG. 20A with the anchors 2008 in an affixation configuration protruding away from the annuloplasty ring 2000. An integrated diaphragm 2062 may be integrated with the outer shell 2042 and/or the inner support structure 2040. Inflation of the integrated diaphragm 2062 unfurls the anchors 2008 to expose the barbs 2054 for affixation (implantation) of the annuloplasty ring 2000 into a heart valve annulus. In another embodiment, rather than including an integrated diaphragm 2062, a balloon catheter (not shown) may be used to deploy the anchors 2008.

Those having skill in the art will understand from the disclosure herein that many changes may be made to the details of the above-described embodiments without departing from the underlying principles of the invention. The scope of the present invention should, therefore, be determined only by the following claims.

The invention claimed is:

1. An annuloplasty ring for transcatheter heart valve repair, the annuloplasty ring comprising:
   an outer hollow member comprising a plurality of segments, wherein adjacent segments cooperate with one another to change the outer hollow member from an elongate insertion geometry to an annular operable geometry; and
   an internal anchor member located at least partially within the outer hollow member, the internal anchor member comprising a plurality of anchors configured to attach the annuloplasty ring to tissue of a heart valve annulus, the internal anchor member configured to move the plurality of anchors with respect to a plurality of windows in the outer hollow member to selectively deploy the plurality of anchors through the plurality of windows, respectively,
   wherein the internal anchor member comprises a superelastic shape memory material configured to automatically transition at least a portion of the internal anchor member from the elongate insertion geometry to the annular operable geometry upon exiting a catheter within a heart chamber,
   wherein the internal anchor member comprises a first shape memory ribbon having the plurality of anchors cut therein, wherein the plurality of anchors are configured to automatically transition to a curved shape upon exiting the plurality of windows in the outer hollow member, and wherein the transition to the curved shape self-propels the plurality of anchors into the tissue of the heart valve annulus,
   wherein the internal anchor further comprising a second shape memory ribbon within the outer hollow member, the second shape memory ribbon configured to reduce friction between the first shape memory ribbon and the outer hollow member to assist in deploying the anchors.

2. The annuloplasty ring of claim 1, wherein the plurality of segments allow the outer hollow member to be flexible in a first plane so as to be transitionable between the elongate insertion geometry and the annular operable geometry, and wherein the plurality of segments in the annular insertion geometry are at least semi-rigid in a second plane that is perpendicular to the first plane.

3. The annuloplasty ring of claim 1, wherein the outer hollow member comprises a first end and a second end, and wherein the first end is configured to couple to the second end in the annular operable geometry.

4. The annuloplasty ring of claim 3, further comprising:
   a female snap-lock connector attached to the first end of the outer hollow member; and
   a male snap-lock connector attached to the second end of the outer hollow member.

5. The annuloplasty ring of claim 4, further comprising a suture or wire including a distal end configured to draw the male snap lock connector into the female snap lock connector by applying tension to a proximal end of the suture or wire.

6. The annuloplasty ring of claim 1, further comprising a pivot configured to removably couple the annuloplasty ring to a shuttle configured to pass through the catheter, the pivot further configured to automatically rotate a plane of the annuloplasty ring upon exiting the catheter within the heart chamber.

7. The annuloplasty ring of claim 1, wherein the outer hollow member comprises a superelastic shape memory material configured to automatically transition from the elongate insertion geometry to the annular operable geometry upon exiting the catheter within the heart chamber.

8. The annuloplasty ring of claim 7, wherein the outer hollow member comprises a shape memory tube cut in a pattern to form the plurality of segments in a continuous series of connected segments.

9. The annuloplasty ring of claim 8, wherein
in the elongate insertion geometry, the cut shape memory tube include gaps partially separating adjacent connected segments, and wherein
in the annular operable geometry, one or more of the gaps close.

10. The annuloplasty ring of claim 1, wherein the second shape memory ribbon is superelastic and is configured to automatically transition from the elongate insertion geometry to the annular operable geometry upon exiting the catheter within the heart chamber.

11. The annuloplasty ring of claim 1, wherein the second shape memory ribbon comprises a selectively adjustable member configured to be activated postoperatively by application of external energy to change the shape of the annuloplasty ring.

12. The annuloplasty ring of claim 1, further comprising a suture or wire including a distal end removably coupled to the internal anchor member, the suture or wire configured to slide the internal anchor member within the outer hollow member, by applying tension to a proximal end of the suture or wire, so as to deploy the plurality of anchors from the plurality of windows.

13. The annuloplasty ring of claim 1, wherein the annular operable geometry comprises a D-shape corresponding to an anatomical geometry of a human mitral valve annulus, wherein the annuloplasty ring in the annular operable geometry comprises a first dimension corresponding to an anterior-posterior dimension of the mitral valve annulus and a second dimension corresponding to a commissure-commissure dimension of the mitral valve annulus.

* * * * *